US005773613A

United States Patent [19]

Kawaguchi et al.

[11] Patent Number: 5,773,613

[45] Date of Patent: Jun. 30, 1998

[54] TRYPTOANTHRININIMINE DERIVATIVE AND ELECTROPHOTOSENSITIVE MATERIAL USING THE SAME

[75] Inventors: Hirofumi Kawaguchi; Nobuko Akiba; Yukimasa Watanabe; Hiroaki Iwasaki; Yasuyuki Hanatani; Yasufumi Mizuta; Fumio Sugai; Sakae Saito; Syunichi Matsumoto; Toshiyuki Fukami; Ichiro Yamazato; Hisakazu Uegaito; Yuji Tanaka, all of Osaka, Japan

[73] Assignee: Mita Industrial Co., Ltd., Osaka, Japan

[21] Appl. No.: 563,545

[22] Filed: Nov. 28, 1995

[30] Foreign Application Priority Data

| | | | |
|---|---|---|---|
| Nov. 29, 1994 | [JP] | Japan | 6-295382 |
| Feb. 28, 1995 | [JP] | Japan | 7-039641 |
| Feb. 28, 1995 | [JP] | Japan | 7-039644 |
| Jul. 17, 1995 | [JP] | Japan | 7-180305 |
| Jul. 17, 1995 | [JP] | Japan | 7-180306 |

[51] Int. Cl.$^{6}$ .......... C07D 487/02; G03G 5/06

[52] U.S. Cl. .......... 544/246; 430/78; 430/83

[58] Field of Search .......... 544/246

[56] References Cited

U.S. PATENT DOCUMENTS 4,666,526 5/1987 Rolf et al. .......... 106/309

5,420,259 5/1995 Guentner et al. .......... 544/246

5,616,441 4/1997 Kawaguchi et al. .......... 544/246

FOREIGN PATENT DOCUMENTS 0615165 9/1994 European Pat. Off. .

*Primary Examiner*—Emily Bernhardt

*Attorney, Agent, or Firm*—Beveridge, DeGrandi, Weilacher & Young, LLP

[57] ABSTRACT

The present invention provides a tryptoanthrinimine derivative represented by the general formula (Y):

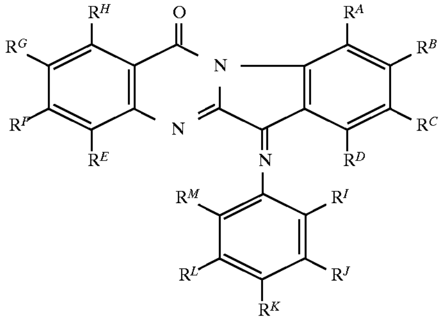

(Y)

wherein $R^A$ to $R^M$ are as defined. Such a derivative of the general formula (Y) is superior in electron transferring capability. Accordingly, an electrophotosensitive material comprising a photosensitive layer containing this derivative (Y) is superior in sensitivity.

7 Claims, 16 Drawing Sheets

TRYPTOANTHRINIMINE DERIVATIVE AND ELECTROPHOTOSENSITIVE MATERIAL USING THE SAME

BACKGROUND OF THE INVENTION

The present invention relates to a novel tryptoanthrinimine derivative, and an electrophotosensitive material using the same. More particularly, it relates to an electrophotosensitive material which is suitable for trying to speed up image forming apparatuses such as copying machine, laser printer, etc.

In the image forming apparatuses by means of electrophotographic processes, such as copying machine, laser printer, etc., a photoconductor for forming an electrostatic latent image is used. As the photoconductor, an organic photoconductor (OPC) having a sensitivity within the wavelength range of a light source of the image forming apparatus has widely been used, recently.

As the organic photoconductor, a multi-layer type (so-called function-separating type) photoconductor comprising an electric charge generating layer and an electric charge transferring layer, which are mutually laminated, has exclusively been known, but a single-layer type photoconductor wherein an electric charge generating material and an electric charge transferring material are dispersed in a photosensitive layer, has also been known. In addition, the organic photoconductor is classified into two types, i.e. so-called positive charging and negative charging types, according to the electric charge to be generated on the surface.

High carrier mobility is required for the above electric charge transferring material. However, among electric charge transferring materials which have hitherto been known, almost all of them having a high carrier mobility show hole transferring properties. Therefore, a structure of the organic photoconductor using the above electric charge transferring material is limited to a negative charging type multi-layer type one, which is provided with an electric charge transferring layer at the outermost layer, from the viewpoint of mechanical strength. However, since the negative charging type organic photoconductor utilizes negative-polarity corona discharge, problems such as large amount of ozone generated, environmental pollution, deterioration of photoconductor, etc. have arisen.

Accordingly, in order to solve the above problems, it has been studied to use an electron transferring material as the electric charge transferring material. In Japanese Laid-Open Patent Publication No. 1-206349, there is suggested that a compound having a diphenoquinone structure is used as the electron transferring material for electrophotosensitive material.

As described in the above gazette, diphenoquinones are superior in electron transferring properties and a positive charging type photoconductor having a good photosensitivity can be obtained by using these diphenoquinones.

However, conventional electron transferring materials including a diphenoquinone derivative are inferior in compatibility with binding resin, and it is difficult to cause electron transfer at low electric field because a hopping distance becomes large. Therefore, the electrophotosensitive material containing a conventional electron transferring material had a problem that a residual potential becomes considerably high, which results in low sensitivity.

In addition, the above electron transferring material causes insufficient injection of electrons from a pigment to be used as the electric charge generating material.

Furthermore, the above electron transferring material is inferior in solubility in solvent and compatibility with binding resin.

If the organic photoconductor can be used for the single-layer type, it becomes easy to produce a photoconductor, thereby affording a lot of advantages for preventing defects from generating and improving optical characteristics. However, the single-layer type photosensitive layer had a problem that an interaction between diphenoquinone and a hole transferring material inhibits electrons from transferring.

On the other hand, in Japanese Laid-Open Patent Application No. 6-130688, there is a description that an electrophotosensitive material having an excellent sensitivity can be obtained by using a hole transferring material of an alkyl-substituted N,N,N',N'-tetrakis(4-methylphenyl)-3,3'-dimethylbenzene derivative in combination with an electric charge generating material of a phthalocyanine pigment even if 3,5-dimethyl-3',5'-di-t-butyl-4,4'-diphenoquinone derivative, which is a diphenoquinone derivative, is used as the electron transferring material. However, in this case, there is a disadvantage that a wear resistance of the resulting photoconductor is insufficient.

In addition, in Japanese Patent Publication No. 5-21099, there is disclosed a 3,3'-dimethylbenzidine derivative as a compound having a high hole transferring capability. However, since this derivative generally has a low melting point (about 180° C. or less), the photosensitive layer obtained by using the derivative has a low glass transition temperature and there is a problem that the durability and heat resistance of the photoconductor becomes insufficient.

SUMMARY OF THE INVENTION

It is a main object of the present invention is to solve the above technical problems, thereby providing a novel derivative which is suitable as an electron transferring material of an electrophotosensitive material.

It is another object of the present invention is to provide an electrophotosensitive material wherein injection and transferring of electrons from an electric charge generating material are smoothly conducted and the sensitivity is improved in comparison with a conventional one.

It is still another object of the present invention to provide an electrophotosensitive material having an organic photosensitive layer which is superior in wear resistance.

It is a further object of the present invention to provide an electrophotosensitive material wherein a glass transition temperature of a photosensitive layer is sufficiently high, which is superior in durability and heat resistance.

The present inventors have studied intensively in order to accomplish the above objects. As a result, it has been found that a tryptoanthrinimine derivative represented by the general formula (Y):

(Y)

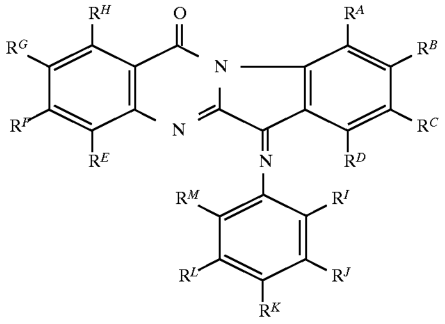

wherein $R^A$, $R^B$, $R^C$, $R^D$, $R^E$, $R^F$, $R^G$ and $R^H$ are the same or different and indicate a hydrogen atom, an alkyl group which may have a substituent, an alkoxy group which may have a substituent, or a nitro group; and $R^I$, $R^J$, $R^K$, $R^L$ and $R^M$ are the same or different and indicate a hydrogen atom, an alkyl group which may have a substituent, an aryl group which may have a substituent, an aralkyl group which may have a substituent, an alkoxy group which may have a substituent, a phenoxy group which may have a substituent, an alkyl halide group or a halogen atom, has an electron transferring capability higher than that of a conventional diphenoquinone compound.

The tryptoanthrinimine derivative represented by the above general formula (Y) of the present invention is superior in solubility in solvent and compatibility with binding resin. Furthermore, the tryptoanthrinimine derivative is superior in matching with electric charge generating material and, therefore, injection of electrons are smoothly conducted. Particularly, it is superior in electron transferring properties at low electric field. Accordingly, the tryptoanthrinimine derivative (Y) is superior in function as the electron transferring material to a conventional diphenoquinone compound.

Accordingly, the electrophotosensitive material of the present invention comprises a conductive substrate and a photosensitive layer provided on the conductive substrate, and the photosensitive layer contains the above tryptoanthrinimine derivative (Y) as the electron transferring material. Thereby, an organic photosensitive material having a high sensitivity can be obtained.

The tryptoanthrinimine derivative of the present invention contains the following compounds represented by the general formulas (1), (6) and (7).

General formula (1):

(1)

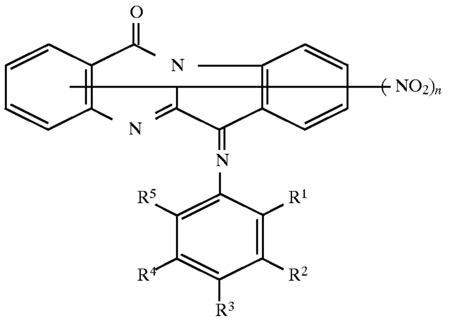

wherein $R^1$, $R^2$, $R^3$, $R^4$ and $R^5$ are the same or different and indicate a hydrogen atom, an alkyl group, an aryl group, an aralkyl group, an alkoxy group, an alkyl halide group or a halogen atom; and n is an integer of 1 to 4.

General formula (6):

(6)

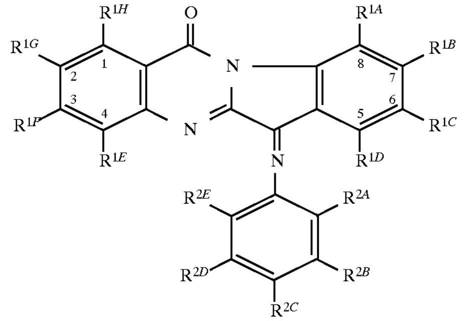

wherein $R^{1A}$, $R^{1B}$, $R^{1C}$, $R^{1D}$, $R^{1E}$, $R^{1F}$, $R^{1G}$ and $R^{1H}$ are the same or different and indicate a hydrogen atom, an alkyl group which may have a substituent, or an alkoxy group which may have a substituent; $R^{2A}$, $R^{2B}$, $R^{2C}$, $R^{2D}$ and $R^{2E}$ are the same or different and indicate a hydrogen atom, an alkyl group which may have a substituent, an alkoxy group which may have a substituent, an aryl group which may have a substituent, an aralkyl group which may have a substituent, a phenoxy group which may have a substituent, or a halogen atom.

General formula (7):

(7)

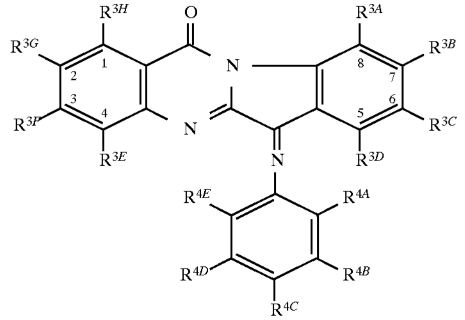

wherein at least two substituents of $R^{3A}$, $R^{3B}$, $R^{3C}$, $R^{3D}$, $R^{3E}$, $R^{3F}$, $R^{3G}$ and $R^{3H}$ indicate a nitro group, at least one substituent indicates an alkyl group or an alkoxy group, and others indicate a hydrogen atom; $R^{4A}$, $R^{4B}$, $R^{4C}$, $R^{4D}$ and $R^{4E}$ are the same or different and indicate a hydrogen atom, an alkyl group, an alkoxy group, an aryl group which may have a substituent, an aralkyl group which may have a substituent, or a halogen atom.

One preferred electrophotosensitive material of the present invention has a photosensitive layer containing the tryptoanthrinimine derivative represented by the above general formula (Y) and a phenylenediamine derivative represented by the general formula (2):

(2)

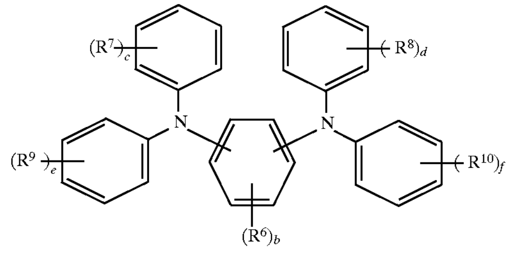

wherein $R^6$ to $R^{10}$ are the same or different and indicate an alkyl group, an aryl group, an alkoxy group or an alkoxy halide group; and b to f are the same or different and indicate an integer of 0 to 4.

That is, there can be obtained an electrophotosensitive material, which is not only high sensitivity, but also superior in wear resistance, by using the tryptoanthrinimine derivative (Y) as the electron transferring material and using a phenylenediamine derivative (2) as the hole transferring material.

Another preferred electrophotosensitive material has a photosensitive layer containing tryptoanthrinimine derivative represented by the above general formula (Y) and at least one selected from benzidine derivatives represented by the general formula (3):

(3)

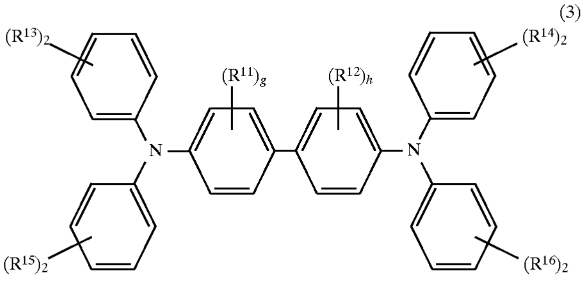

wherein $R^{11}$, $R^{12}$, $R^{13}$, $R^{14}$, $R^{15}$ and $R^{16}$ are the same or different and indicate an alkyl group; and g and h indicate an integer of 0 to 2, general formula (4):

(4)

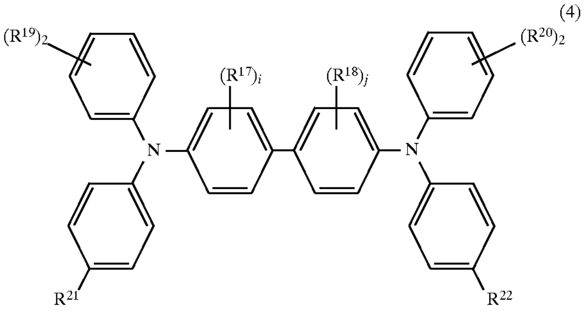

wherein $R^{17}$, $R^{18}$, $R^{19}$ and $R^{20}$ are the same or different and indicate an alkyl group; $R^{21}$ and $R^{22}$ are the same or different and indicate an alkyl or aryl group having 3 to 5 carbon atoms; and i and j indicate an integer of 0 to 2, and general formula (5):

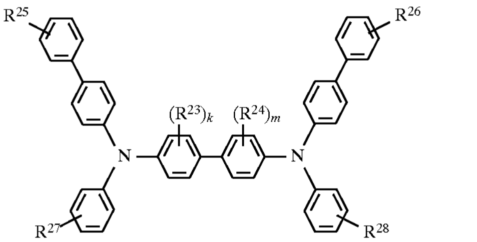

(5)

wherein $R^{23}$ and $R^{24}$ are the same or different and indicate an alkyl group; $R^{25}$ and $R^{26}$ are the same or different and indicate a hydrogen atom or an alkyl group; $R^{27}$ and $R^{28}$ are the same or different and indicate a hydrogen atom, an alkyl group or an aryl group; and k and m indicate an integer of 0 to 2.

That is, there can be obtained an electrophotosensitive material wherein a glass transition temperature of a photosensitive layer is sufficiently high, which is also superior in durability and heat resistance, in addition to high sensitivity, by using the above derivative (Y) as the electron transferring material and using a benzidine derivative (3), (4) or (5) as the hole transferring material.

Furthermore, the above derivatives (Y) can also be used for applications such as solar battery, EL device, etc. by making using of their high electron transferring capabilities.

DETAILED DESCRIPTION OF THE INVENTION

Figure 1:
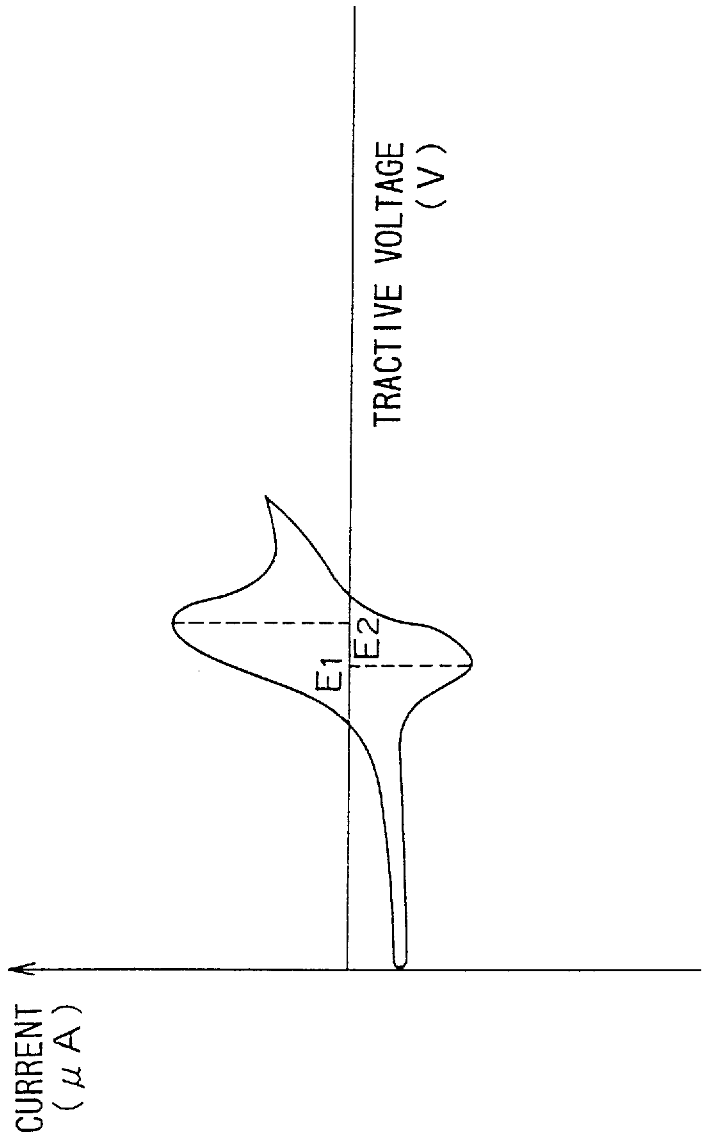
FIG. 1 is a graph showing a relation between the tractive voltage (V) and current (A) for determining the redox potential in the present invention.

In the triptoanthrinimine derivatives represented by general formula (Y), examples of the alkyl group include groups having 1 to 6 carbon atoms, such as methyl, ethyl, n-propyl, isopropyl, n-butyl, s-butyl, t-butyl, n-pentyl, n-hexyl, etc. Examples of the aryl group include phenyl, naphthyl, anthryl, phenanthryl, etc. Examples of the aralkyl group include groups of which alkyl moiety has 1 to 6 carbon atoms, such as benzyl, benzhydryl, trityl, phenethyl, etc. Examples of the alkoxy group include groups having 1 to 6 carbon atoms such as methoxy, ethoxy, n-propoxy, isopropoxy, t-butoxy, pentyloxy, hexyloxy, etc. Examples of the alkyl halide group include groups of which alkyl moiety has 1 to 6 carbon atoms, such as chloromethyl, bromomethyl, fluoromethyl, iodomethyl, dibromomethyl, trifluoromethyl, 1,2-dichloroethyl, perfluoro-t-butyl, 1-chlorohexyl, 1,2-dibromopentyl, 1,2,3,4,5,6-hexaiodohexyl, etc. Examples of the halogen atom include chlorine, bromine, fluorine, iodine, etc. In addition, the number of the nitro group defined by the symbol "n" in the general formula (1) is optionally selected within a range of 1 to 4.

One or more substituents such as alkyl group, alkoxyl group, halogen atom, etc. may be substituted on the above aryl and aralkyl groups, and the substitution position is not limited.

The tryptoanthrinimine derivative (1) of the present invention is synthesized as shown in the following reaction schemes (I) and (II). That is, a compound (1) of the present invention is obtained by nitrating tryptoanthrine (8) to synthesize a compound (9), and then reacting the compound (9) with an aniline derivative (10).

Reaction scheme (I):

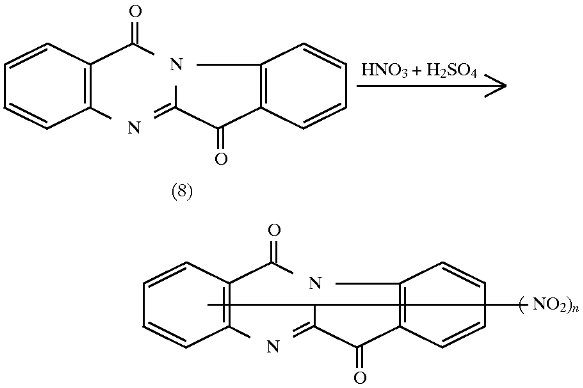

(8)

(9)

wherein n is as defined above.

As shown in the above reaction scheme, tryptoanthrine (8) is normally reacted (nitrated) in a mixed solvent of nitric acid and sulfuric acid (mixed acid) at a temperature of −20° to 80° C. for about 30 minutes to 6 hours to obtain nitrated tryptoanthrine (9).

The mixing ratio of nitric acid to sulfuric acid is 1:2 to 4:1, preferably 1:1 (weight ratio).

Reaction scheme II:

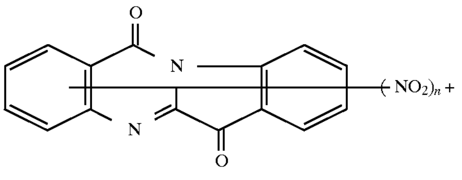
(9)

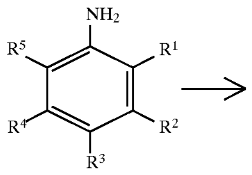
(10)

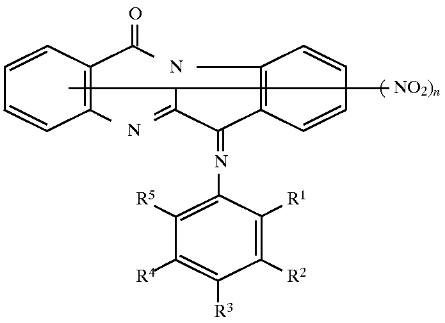
(1)

wherein $R^1$ to $R^5$ and n are as defined above.

As shown in this reaction scheme, a nitrated tryptoanthrinimine derivative (1) is obtained by reacting the above compound (9) with the aniline derivative (10) in a suitable solvent.

As the solvent in the above reaction, for example, acetic acid, propionic acid, butanoic acid, chloroform, tetrahydrofuran, dimethylformamide, dimethyl sulfoxide, etc. can be used. The reaction is normally conducted at a temperature of 30° to 170° C., preferably 70° to 110° C., for about 20 minutes to 4 hours.

Examples of the tryptoanthrinimine derivative (1) of the present invention include the compounds represented by the following formulas (1-1) to (1-11).

(1-1)
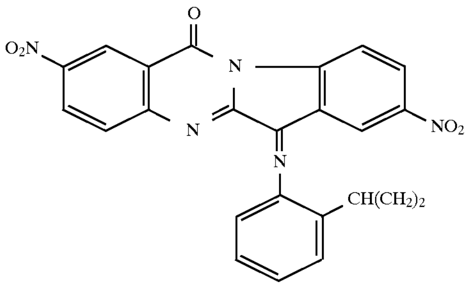

(1-2)
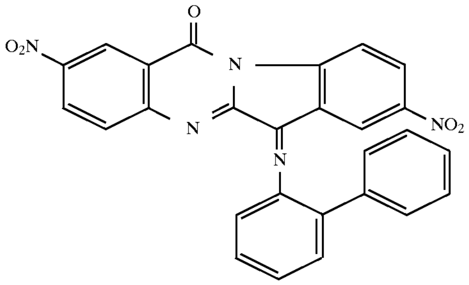

(1-3)
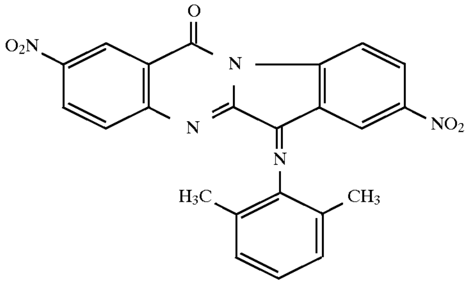

(1-4)
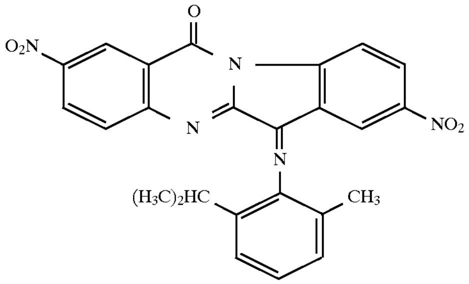

(1-5)
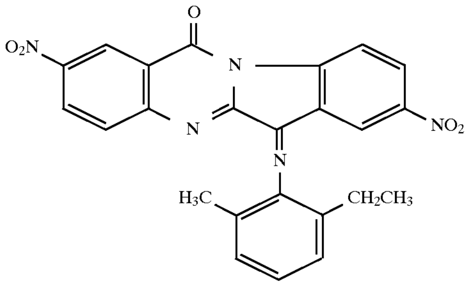

-continued (1-6)

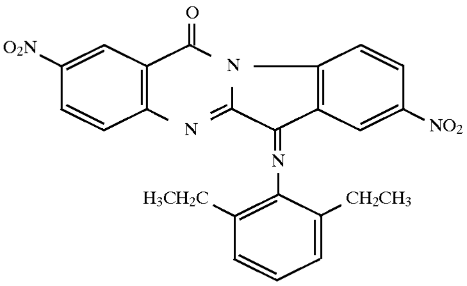

(1-7)

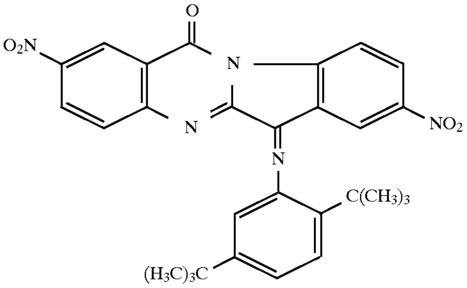

(1-8)

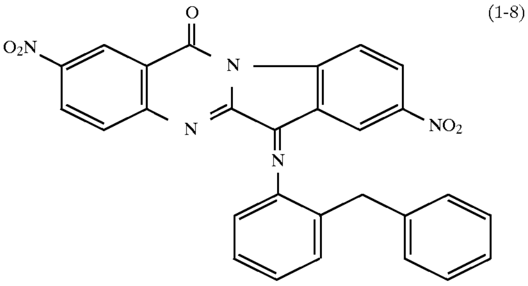

(1-9)

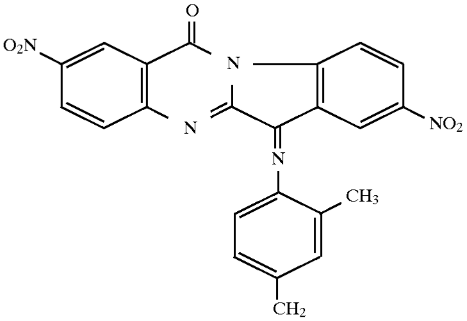

(1-10)

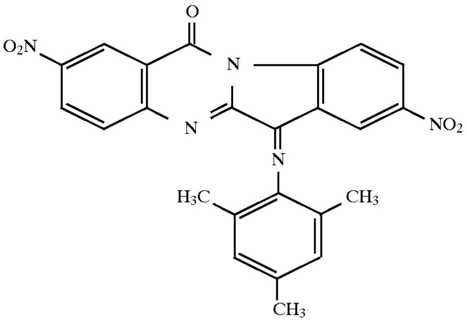

-continued (1-11)

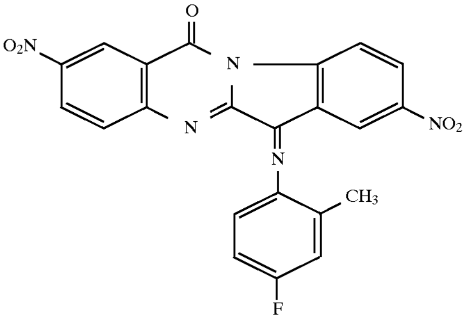

In the tryptoanthrinimine derivative of the general formula (6), it is preferred that not more than four, particularly not more than two substituents of the substituents $R^{1A}$ to $R^{1H}$ indicate an alkyl group which may have a substituent or an alkoxy group which may have a substituent, and others indicate a hydrogen atom. It is preferred that at least one, particularly at least two substituents among the substituents $R^{2A}$ to $R^{2E}$ indicate a hydrogen atom and other substituents indicate a substituent other than hydrogen atom.

Similarly, regarding the tryptoanthrinimine derivative of the general formula (7), it is preferred that not more than four, particularly not more than two substituents of the substituents $R^{3A}$ to $R^{3H}$ indicate an alkyl group which may have a substituent or an alkoxy group which may have a substituent, and others indicate a hydrogen atom. It is preferred that at least one, particularly at least two substituents among the substituents $R^{4A}$ to $R^{4E}$ indicate a hydrogen atom and other substituents indicate a substituent other than hydrogen atom.

Examples of the tryptoanthrinimine derivative (6) include the compounds represented by the following formulas (6-1) to (6-7).

(6-1)

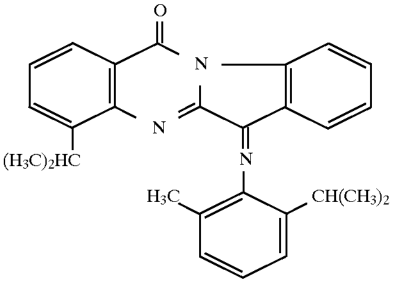

(6-2)

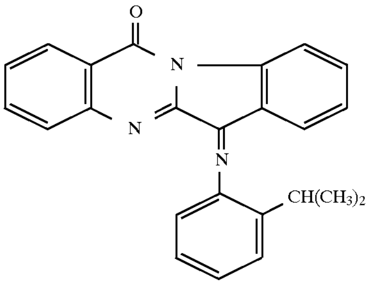

-continued
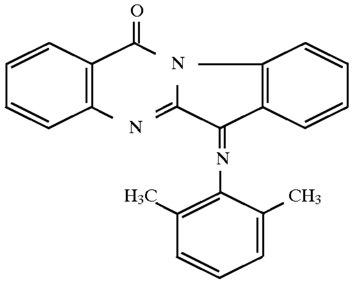
(6-3)
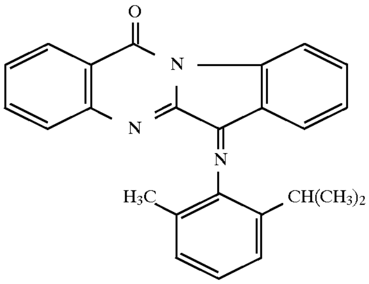
(6-4)
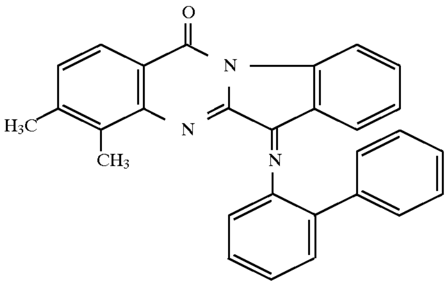
(6-5)
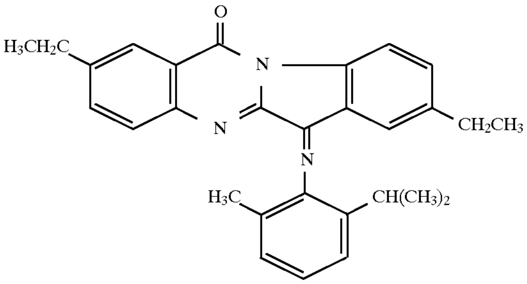
(6-6)
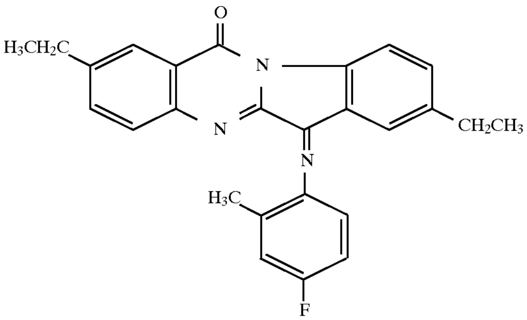
(6-7)
Examples of the tryptoanthrinimine derivative (7) of the present invention include the compounds represented by the following formulas (7-1) to (7-3).
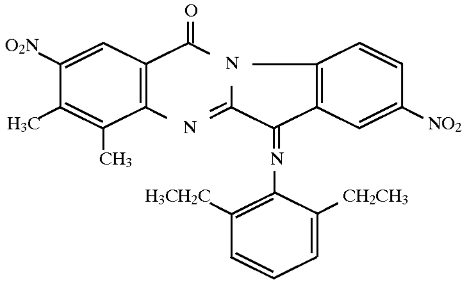
(7-1)
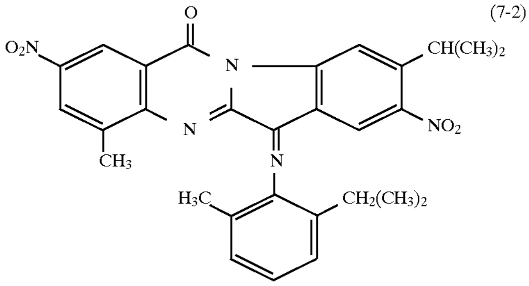
(7-2)
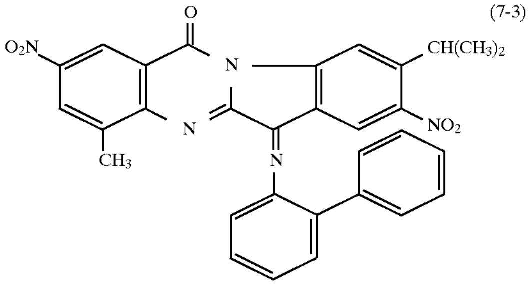
(7-3)
Next, the production process of the tryptoanthrinimine derivative (6) of the present invention will be explained.
Reaction scheme (III):
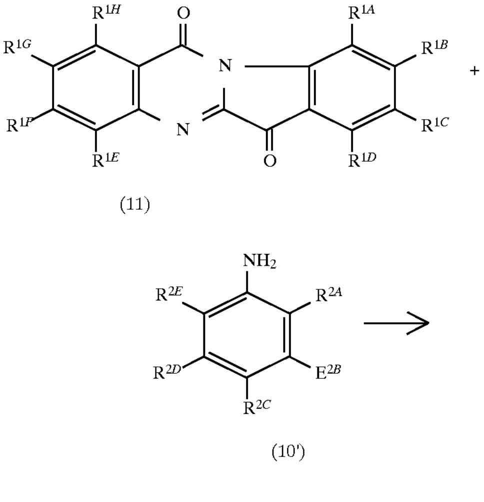
(11)
(10')

-continued

Reaction scheme (III):

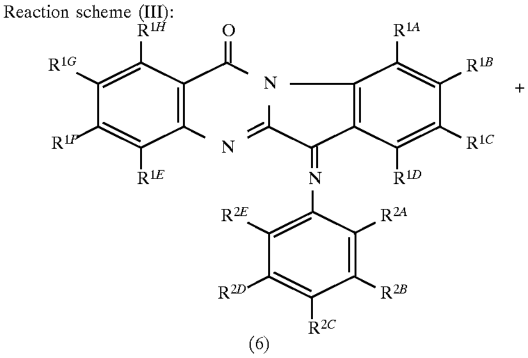

(6)

wherein $R^{1A}$ to $R^{1H}$ and $R^{2A}$ to $R^{2E}$ are as defined above.

The tryptoanthrinimine derivative (6) of the present invention is obtained by reacting a corresponding tryptoanthrine derivative (11) with an aniline derivative (12), as shown in the above reaction scheme (III). This reaction is normally conducted in a solvent such as acetic acid, propionic acid, butanoic acid, chloroform, tetrahydrofuran, dimethylformamide, dimethyl sulfoxide, etc. at a temperature of 30° to 170° C., preferably 70° to 110° C., for 20 minutes to 4 hours.

The tryptoanthrine derivative (11) as a starting material of the above reaction is obtained by reacting an isatin derivative with an anhydride of an isatoic acid derivative. The synthesis process of 4-isopropyltryptoanthrine (14) will be shown as the embodiment thereof.

Reaction scheme (IV):

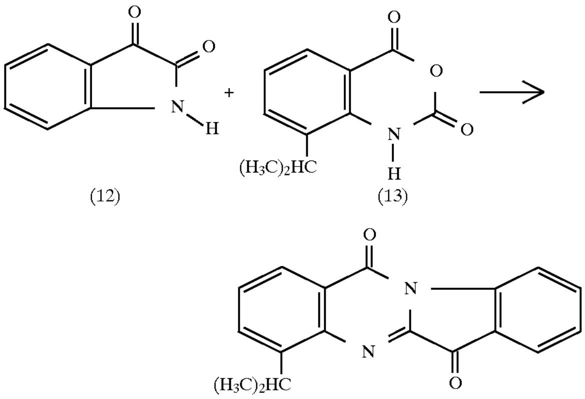

(12) (13)

(14)

As shown in the above reaction scheme (IV), 4-isopropyltryptoanthrine (14) is obtained by reacting isatin (12) with 8-isopropylisatoic anhydride (13). This reaction is normally conducted in a solvent such as dimethylformamide, dimethyl sulfoxide, pyridine, chloroform, tetrahydrofuran, etc. at a temperature of 40° to 130° C. for 1 to 8 hours.

Further, isatin (12) is obtained by reacting an aniline derivative with oxalyl chloride (15) in a solvent such as nitrobenzene, etc. in the presence of a catalyst such as aluminum chloride, etc. at a temperature of about 70° C. for about 5 hours, as shown in the following reaction scheme (V).

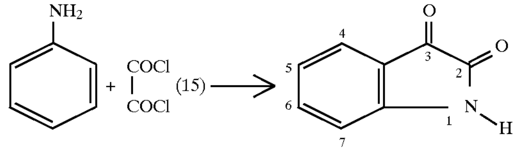

(12)

In addition, isatoic anhydride (13) represented by the formula:

(13)

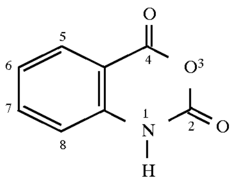

is obtained by reacting isatin in a solvent such as acetic acid, etc. in the presence of hydrogen peroxide and a catalytic amount of sulfuric acid at a temperature of 60° to 70° C. for about 3 hours.

The tryptoanthrinimine derivative of the general formula (7) is obtained by reacting a corresponding tryptoanthrine derivative with an aniline derivative according to the same manner as the production process of the derivative of the general formula (6).

In the electrophotosensitive material of the present invention, a binding resin constituting a photosensitive layer contains the tryptoanthrinimine derivative represented by the above general formula (1), (6) or (7) as the electron transferring material.

The tryptoanthrinimine derivative (1), (6) or (7) of the present invention has a more extended π-electron conjugate system in comparison with a diphenoquinone derivative which has hitherto been used as the electron transferring material, and exhibits a high electron transferring capability. In addition, it is superior in solubility in solvent, compatibility with binding resin and matching with electric charge generating material. Matching with the electric charge generating material becomes excellent by introducing a substituent into a tryptoanthrine skeleton.

Accordingly, when using the above tryptoanthrinimine derivative (1), (6) or (7) as the electron transferring material in the electrophotosensitive material, injection of electrons from the electric charge generating material is conducted smoothly to improve electron transferring properties at low electric field. At the same time, the proportion of recombination between electron and hole is decreased and an apparent electric charge generating efficiency approaches to an actual value. As a result, the sensitivity of the photosensitive material is improved. In addition, the residual potential of the photosensitive material is also decreased and the stability and durability at the time of repeat exposing are also improved.

The above photosensitive layer may be classified into two types, i.e. single-layer type containing a hole transferring material and an electric charge generating material together with an electron transferring material, and a multi-layer type comprising an electric charge transferring layer and an electric charge generating layer. It may be both types, but the effect of the use of the above electron transferring material develops drastically in the single-layer type photosensitive material.

In addition, the photosensitive material of the present invention can be positive and negative charging types. It is particularly preferred to use the positive charging type.

In the positive charging type photosensitive material, electrons emitted from the electric charge generating material in the exposure process are smoothly injected into the electron transferring material represented by the above general formula (1), (6) or (7), and then transferred to the surface of the photosensitive layer by means of the giving and receiving of electrons between electron transferring materials to cancel the positive electric charge (+) which has previously been charged on the surface of the photosensitive layer. On the other hand, holes (+) are injected into the hole transferring material and transferred to the surface of the conductive substrate without being trapped on the way, and then holes are canceled by the negative charge (−) which has previously been charged on the surface of the conductive substrate. It is considered that the sensitivity of the positive charging type photosensitive material using the compound (1), (6) or (7) can be improved in this manner.

As the hole transferring material in the electrophotosensitive material of the present invention, there can be used hole transferring substances which have hitherto been known, such as diamine compounds such as N,N,N',N'-tetrakis(p-methylphenyl)-3,3'-dimethylbenzidine, etc.; oxadiazole compounds such as 2,5-di(4-methylaminophenyl)-1,3,4-oxadiazole, etc.; styryl compounds such as 9-(4-diethylaminostyryl)anthracene, etc.; carbazole compounds such as polyvinyl carbazole, etc.; organosilicone compounds; pyrazoline compounds such as 1-phenyl-3-(p-dimethylaminophenyl)pyrazoline, etc.; hydrazone compounds; triphenylamine compounds; imidazole compounds; pyrazole compounds; triazole compounds; indol compounds; oxazole compounds; isoxazole compounds, thiazole compounds; thiadiazole compounds, etc.

As the hole transferring substance, for example, there are N,N,N',N'-tetrakis(p-methylphenyl)-3,3'-dimethylbenzidine, 1,1-bis(4-diethylaminophenyl)-4,4-diphenyl-1,3-butadiene, N-ethyl-3-carbazolylaldehyde diphenylhydrazone, p-N,N-diethylbenzaldehyde diphenylhydrazone, 4-[N,N-bis(p-toluyl)amino]-β-phenylstilbene, etc., but is not limited thereto.

Examples of the hole transferring material include the compounds represented by the following general formulas (HT1) to (HT13):

(HT1)

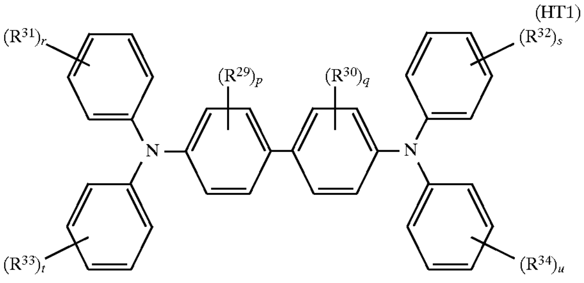

wherein $R^{29}$, $R^{30}$, $R^{31}$, $R^{32}$, $R^{33}$ and $R^{34}$ are the same or different and indicate a hydrogen atom, a halogen atom, an alkyl group which may have a substituent, an alkoxy group which may have a substituent or an aryl group which may have a substituent; p and q are the same or different and indicate an integer of 1 to 4; and r, s, t and u are the same or different and indicate an integer of 1 to 5; $R^{29}$, $R^{30}$, $R^{31}$, $R^{32}$, $R^{33}$ and $R^{34}$ may be different when p, q, r, s, t or u is not less than 2, (HT2)

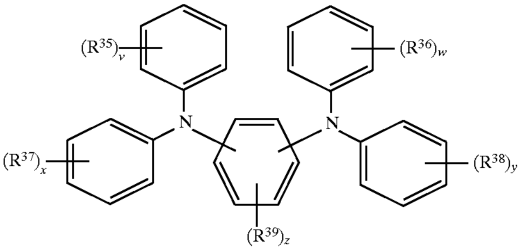

wherein $R^{35}$, $R^{36}$, $R^{37}$, $R^{38}$ and $R^{39}$ are the same or different and indicate a hydrogen atom, a halogen atom, an alkyl group which may have a substituent, an alkoxy group which may have a substituent or an aryl group which may have a substituent; v, w, x and y are the same or different and indicate an integer of 1 to 5; and z is an integer of 1 to 4; $R^{35}$, $R^{36}$, $R^{37}$, $R^{38}$ and $R^{39}$ may be different when v, w, x, y, and z is not less than 2, (HT3)

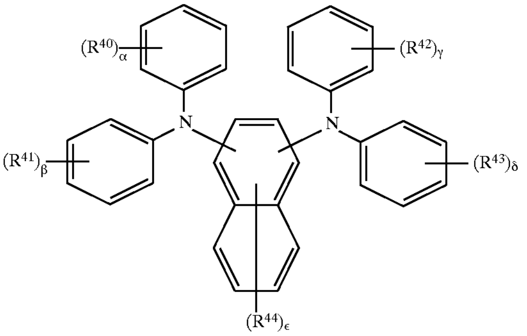

wherein $R^{40}$, $R^{41}$, $R^{42}$ and $R^{43}$ are the same or different and indicate a hydrogen atom, a halogen atom, an alkyl group which may have a substituent, an alkoxy group which may have a substituent or an aryl group which may have a substituent; $R^{44}$ is a hydrogen atom, a halogen atom, a cyano group, a nitro group, an alkyl group which may have a substituent, an alkoxy which may have a substituent or an aryl group which may have a substituent; α, β, γ and δ are the same or different and indicate an integer of 1 to 5; and ε is an integer of 1 to 6; $R^{40}$, $R^{41}$, $R^{42}$, $R^{43}$ and $R^{44}$ may be different when α, β, γ or δ is not less than 2, (HT4)

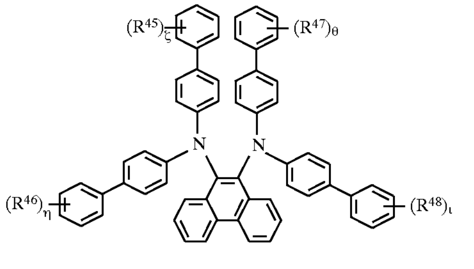

wherein $R^{45}$, $R^{46}$, $R^{47}$ and $R^{48}$ are the same or different and indicate a hydrogen atom, a halogen atom, an alkyl group which may have a substituent, an alkoxy group which may have a substituent or an aryl group which may have a substituent; and ζ, η, θ and ι are the same or different and indicate an integer of 1 to 5; $R^{45}$, $R^{46}$, $R^{47}$ and $R^{48}$ may be different when ζ, η, θ or ι is not less than 2, (HT5)

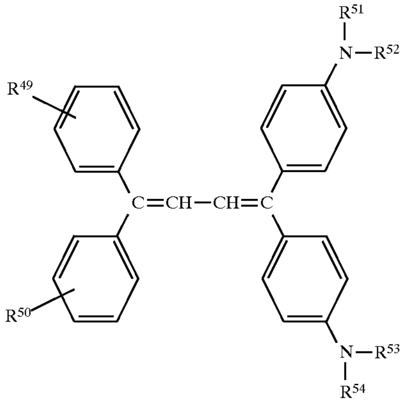

wherein $R^{49}$ and $R^{50}$ are the same or different and indicate a hydrogen atom, a halogen atom, an alkyl group or an alkoxy group; and $R^{51}$, $R^{52}$, $R^{53}$ and $R^{54}$ may be same or different and indicate a hydrogen atom, an alkyl group or an aryl group, (HT6)

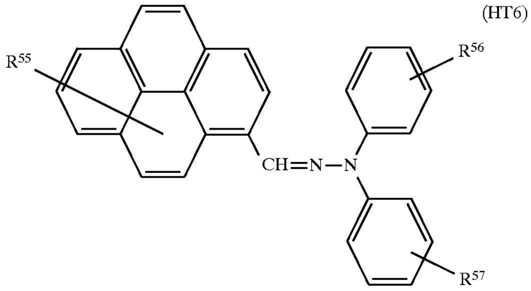

wherein $R^{55}$, $R^{56}$ and $R^{57}$ are the same or different and indicate a hydrogen atom, a halogen atom, an alkyl group or an alkoxy group, (HT7)

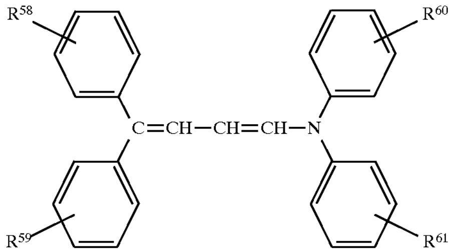

wherein $R^{58}$, $R^{59}$, $R^{60}$ and $R^{61}$ may be same or different and indicate a hydrogen atom, a halogen atom, an alkyl group or an alkoxy group, (HT8)

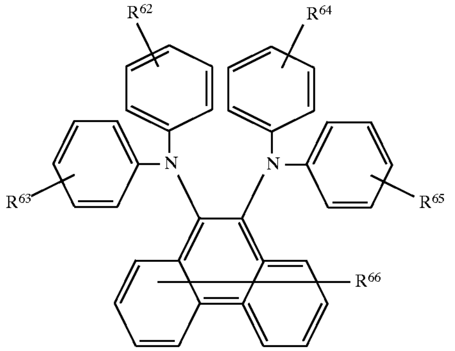

wherein $R^{62}$, $R^{63}$, $R^{64}$, $R^{65}$ and $R^{66}$ may be same or different and indicate a hydrogen atom, a halogen atom, an alkyl group or an alkoxy group, (HT9)

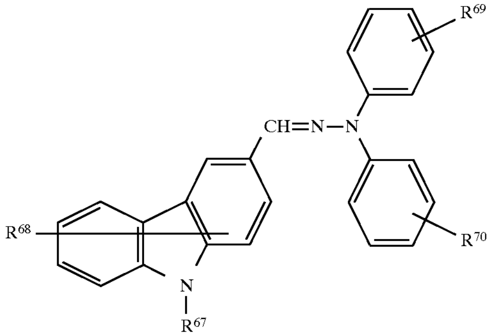

wherein $R^{67}$ is a hydrogen atom or an alkyl group; and $R^{68}$, $R^{69}$ and $R^{70}$ may be same or different and indicate a hydrogen atom, a halogen atom, an alkyl group or an alkoxy group, (HT10)

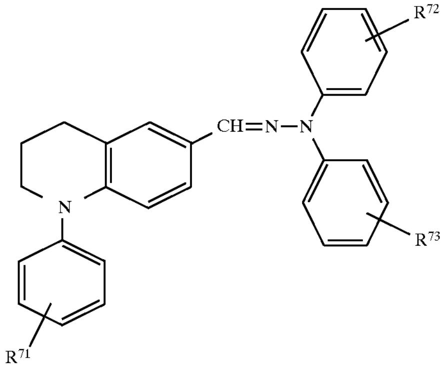

wherein $R^{71}$, $R^{72}$ and $R^{73}$ may be same or different and indicate a hydrogen atom, a halogen atom, an alkyl group or an alkoxy group, (HT11)

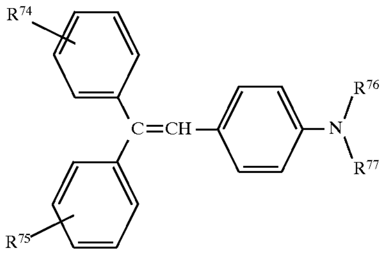

wherein $R^{74}$ and $R^{75}$ are the same or different and indicate a hydrogen atom, a halogen atom, an alkyl group which may have a substituent or an alkoxy group which may have a substituent; and $R^{76}$ and $R^{77}$ are the same or different and indicate a hydrogen atom, an alkyl group which may have a substituent or an aryl group which may have a substituent,

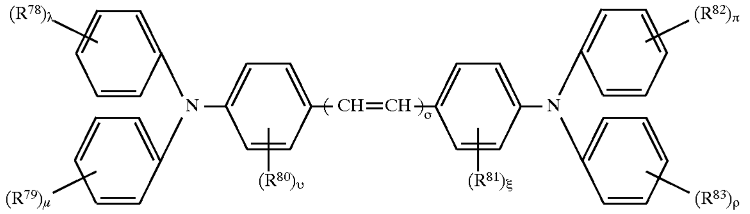

(HT12)

wherein $R^{78}$, $R^{79}$, $R^{80}$, $R^{81}$, $R^{82}$ and $R^{83}$ are the same or different and indicate a hydrogen atom, an alkyl group which may have a substituent, an alkoxy group which may have a substituent or an aryl group which may have a substituent; $\sigma$ is an integer of 1 to 10; $\lambda$, $\mu$, $\upsilon$, $\xi$, $\pi$ and $\rho$ are the same or different and indicate 1 or 2; $R^{78}$, $R^{79}$, $R^{80}$, $R^{81}$, $R^{82}$ and $R^{83}$ may be different when $\lambda$, $\mu$, $\upsilon$, $\xi$, $\pi$ or $\rho$ is 2, and (HT13)

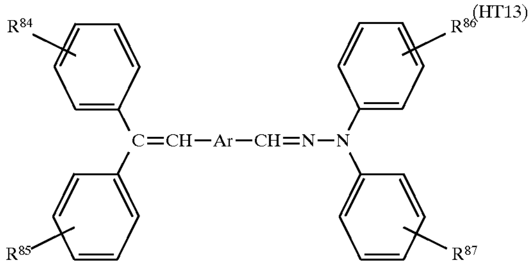

wherein $R^{84}$, $R^{85}$, $R^{86}$ and $R^{87}$ may be same or different and indicate a hydrogen atom, a halogen atom, an alkyl group or an alkoxy group; and Ar indicate a group (Ar1), (Ar2) or (Ar3) represented by the formulas:

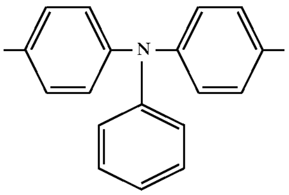

(Ar1)

-continued

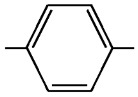

(Ar2)

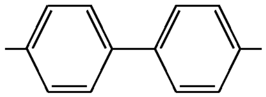

(Ar3)

In the hole transferring material as described above, examples of the alkyl, alkoxy and aryl group include the same groups as those described above.

Examples of the substituent which may be substituted on the above group include halogen atom, amino group, hydroxyl group, optionally esterified carboxyl group, cyano group, alkyl group having 1 to 6 carbon atoms, alkoxy group having 1 to 6 carbon atoms, alkenyl group having 2 to 6 carbon atoms which may have an aryl group, etc. In addition, the substitution position of the above substituent is not specifically limited.

These hole transferring materials are used alone or in combination thereof. In addition, a binding resin is not required necessarily when using a hole transferring material having film-forming properties, such as vinylcarbazole.

Examples of the hole transferring material which can be used for the present invention include benzidine derivatives represented by the formulas (16-1) to (16-5):

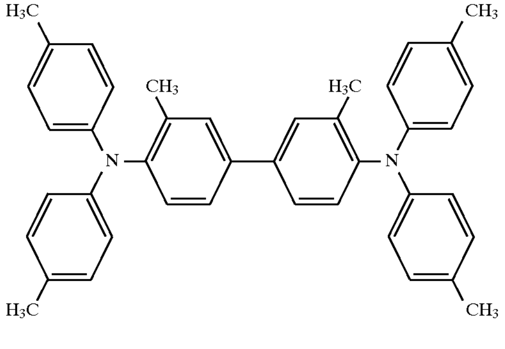

(16-1)

-continued
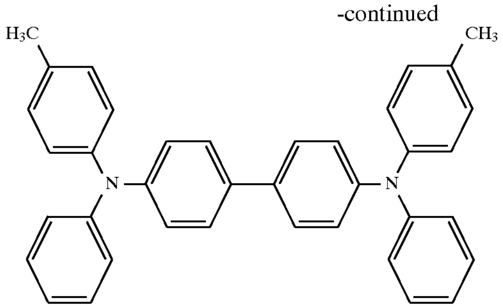
(16-2)
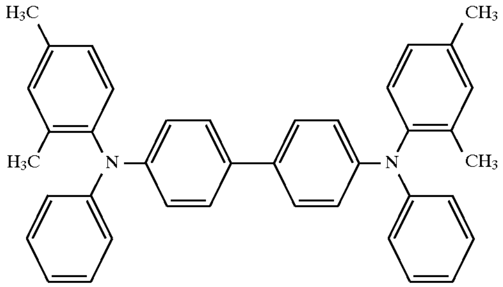
(16-3)
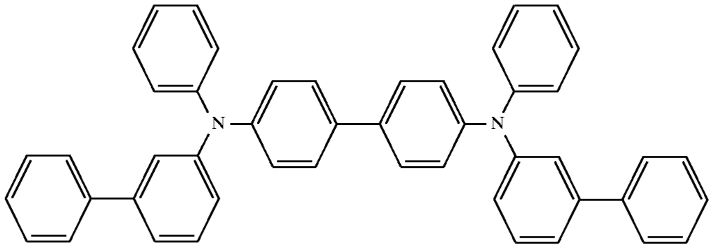
(16-4)
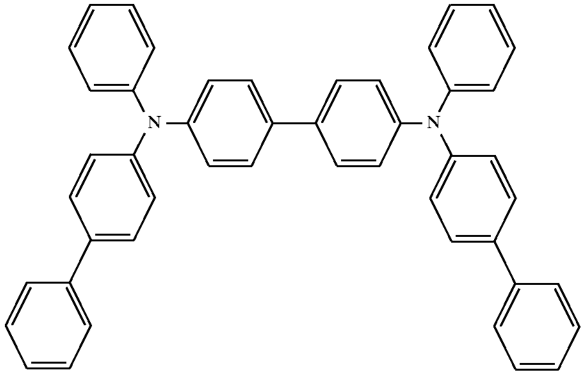
(16-5)
phenylenediamine derivatives represented by the formulas (17-1) to (17-4):
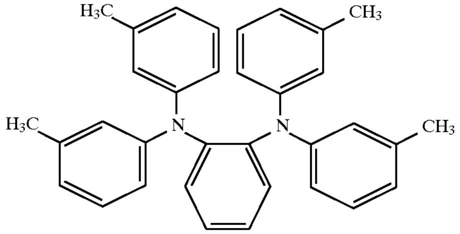
(17-1)
-continued
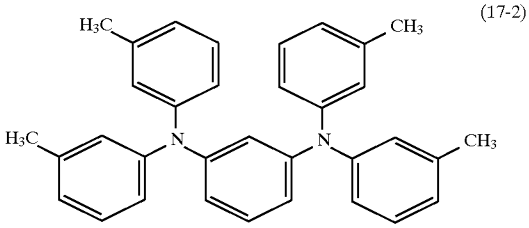
(17-2)

-continued
(17-3)
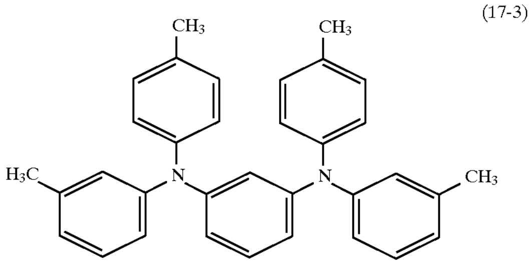
(17-4)
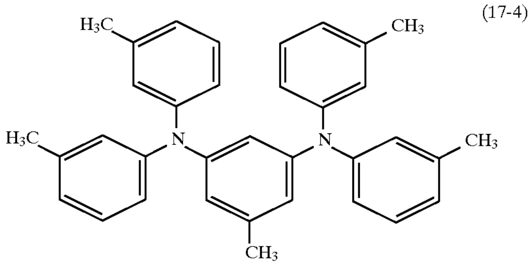
and naphthylenediamine derivatives represented by the formulas (18-1) to (18-9):
(18-1)
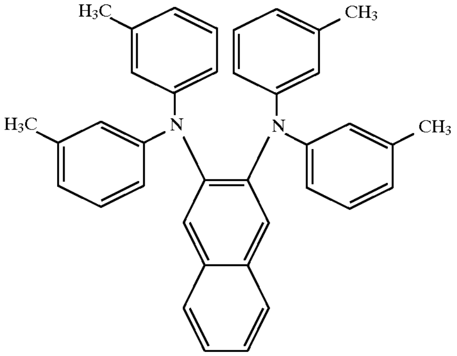
(18-2)
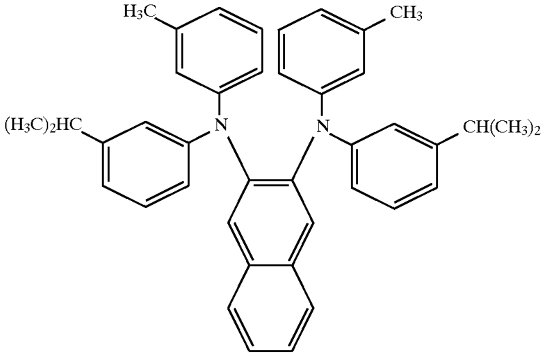

-continued
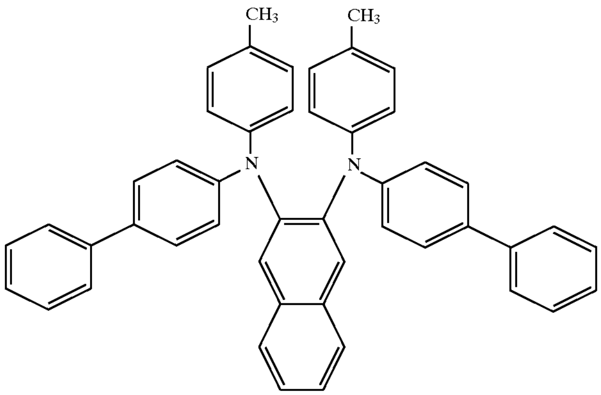
(18-3)
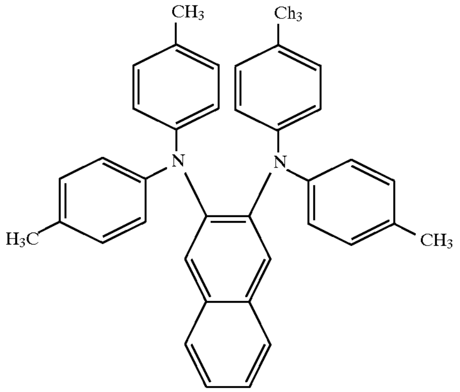
(18-4)
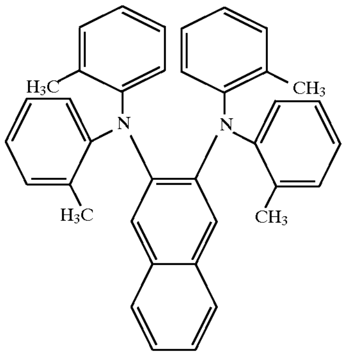
(18-5)
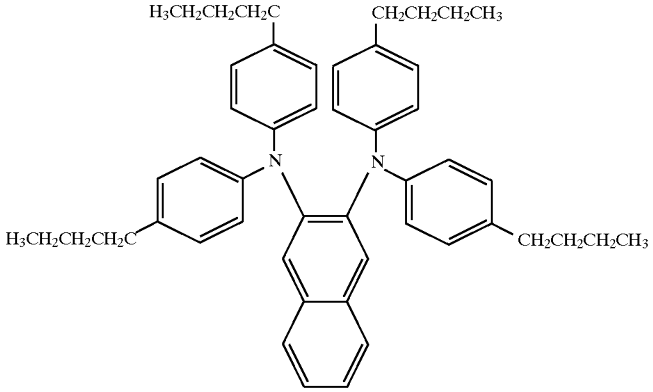
(18-6)

-continued

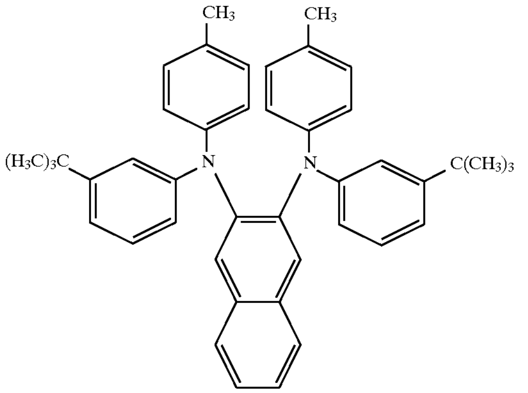

(18-7)

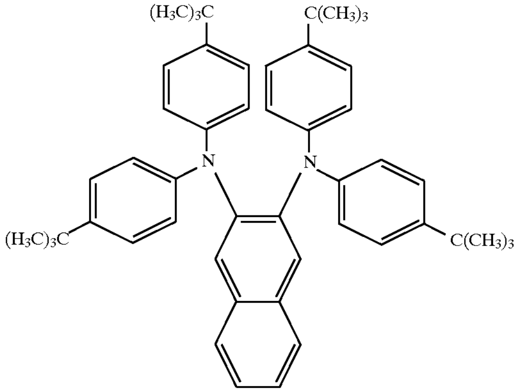

(18-8)

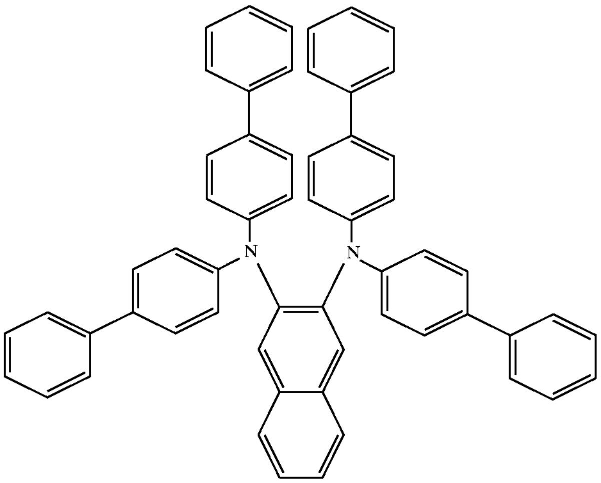

(18-9)

In the present invention, a particularly preferred hole transferring material is a phenylenediamine derivative represented by the above general formula (2).

In the above general formula (2), examples of the alkyl group and aryl group, which correspond to the substituent $R^6$ to $R^{10}$, include the same groups as those described above. Examples of the alkoxy group include methoxy, ethoxy, n-propoxy, isopropoxy, n-butoxy, s-butoxy, t-butoxy, n-pentyloxy, n-hexyloxy, etc. The alkoxy halide group is that in which the above alkoxy group is substituted with halogen atoms such as fluorine, chlorine, bromine, iodine, etc., and the substitution position and number of the halogen atom substituted are not specifically limited. In addition, in the general formula (2), the number of the substituents $R^6$ to $R^{10}$ defined by the symbols b to f is optionally selected within a range of 0 to 4. Preferably, it is selected so that c to f indicate 0, simultaneously.

Examples of the above phenylenediamine derivative (2) include the compounds represented by the following formulas (2-1) to (2-6):

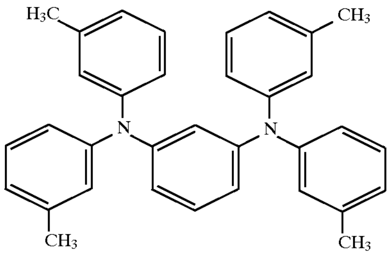
(2-1)
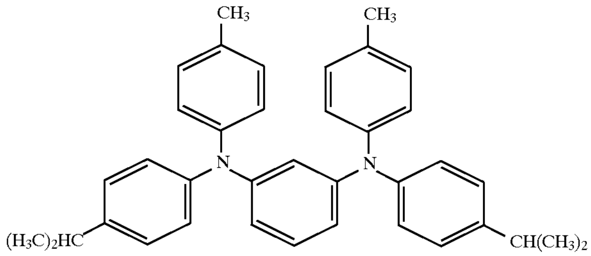
(2-2)
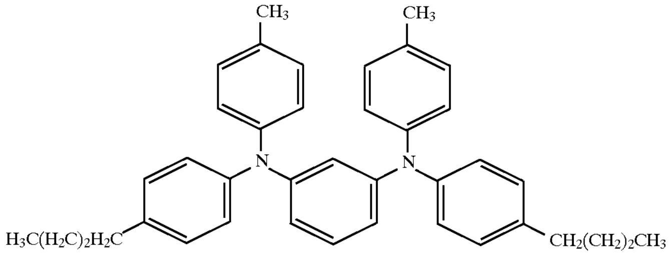
(2-3)
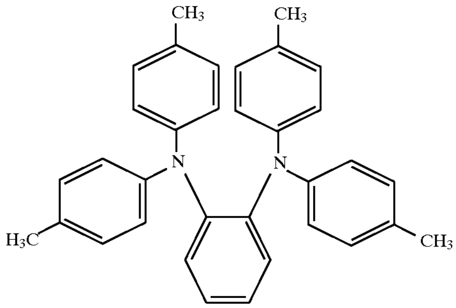
(2-4)
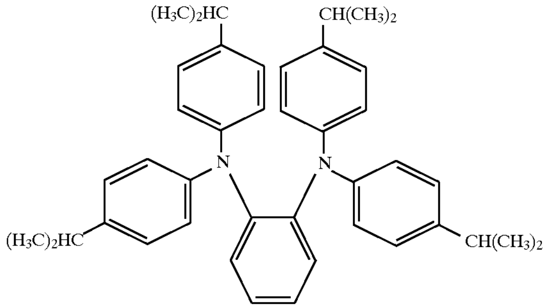
(2-5)

-continued

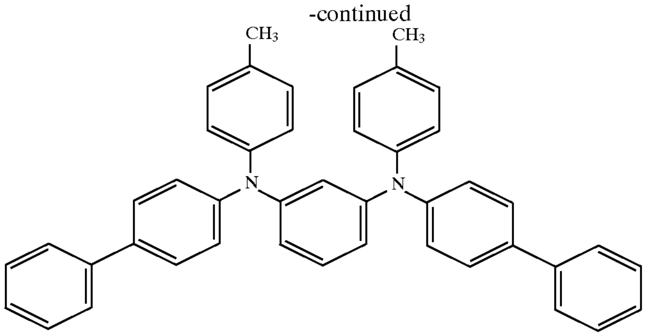

(2-6)

The phenylenediamine derivative (2) can be synthesized by various methods. For example, the phenylenediamine derivative represented by the above formula (2-2) is synthesized by mixing N,N'-diacetyl-1,3-phenylenediamine (19) with p-iodotoluene (20) in a proportion of 1:2 (molar ratio), together with copper powders, copper oxide or copper halide, reacting the mixture in the presence of a basic substance to synthesize a compound (21), as shown in the following reaction scheme (VI). Next, the compound (21) to deacetylation reaction to obtain a compound (22), and then reacting the compound (22) with 4-isopropyliodobenzene (23) in a proportion of 1:2 (molar ratio) according to the same manner as that described above, as shown in the following reaction scheme (VII).

Reaction scheme (VI):

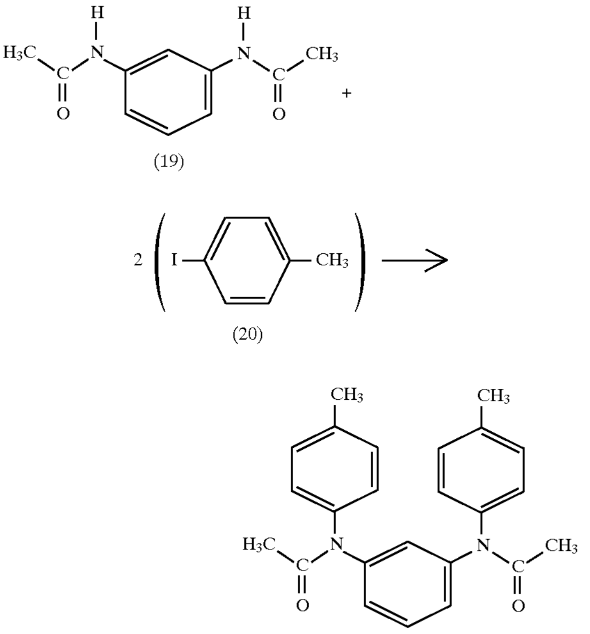

(19) (20) (21)

Reaction scheme (VII):

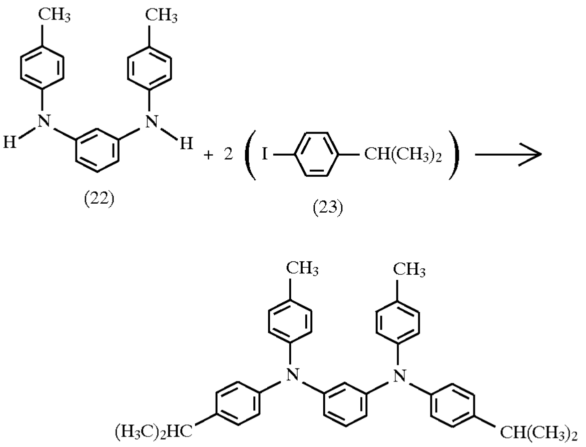

(22) (23) (2-2)

It is considered that the above-described phenylenediamine derivative (2) has a large free volume of the molecule because of it's stereostructure and has an elasticity against strain. When using this phenylenediamine derivative (2) as the hole transferring material in the electrophotosensitive material, a photosensitive layer having an excellent wear resistance can be obtained.

As the other preferred hole transferring material of the present invention, there are benzidine derivatives represented by the above general formulas (3) to (5). These may be used alone or in combination thereof.

In the general formulas (3) to (5), examples of the alkyl group corresponding to the substituents $R^{11}$ to $R^{20}$ and $R^{23}$ to $R^{28}$ include the same groups as those described above. Examples of the alkyl group corresponding to $R^{21}$ and $R^{22}$ include those having 3 to 5 carbon atoms among them. Examples of the aryl group corresponding to $R^{21}$, $R^{22}$, $R^{27}$ and $R^{28}$ include phenyl, naphthyl, anthryl, phenanthryl, etc. In addition, in the general formulas (3) to (5), the number of the substituents to be defined by the symbols g to m is optionally selected within a range of 0 to 2.

Examples of the above benzidine derivative (3) include the compounds represented by the following formulas (3-1) to (3-2):

(3-1)

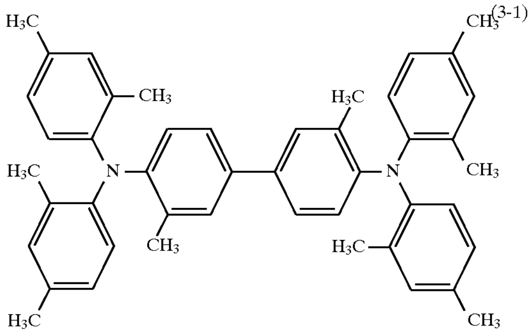

(3-2)

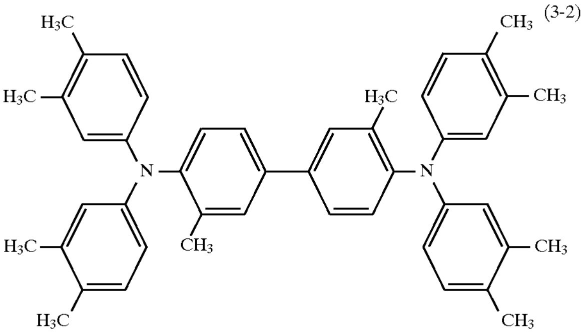

Examples of the above benzidine derivative (4) include the compounds represented by the following formulas (4-1) to (4-5):

(4-1)

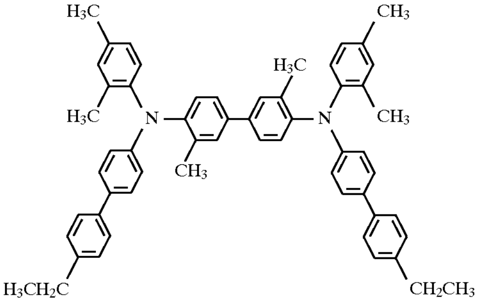

(4-2)

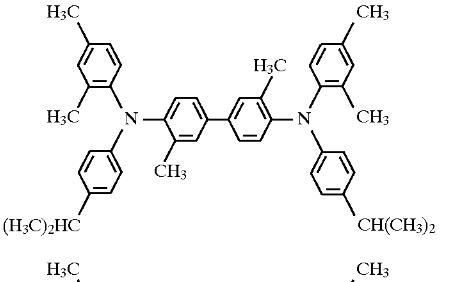

(4-3)

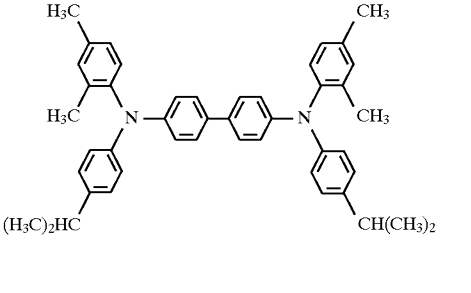

-continued (4-4)

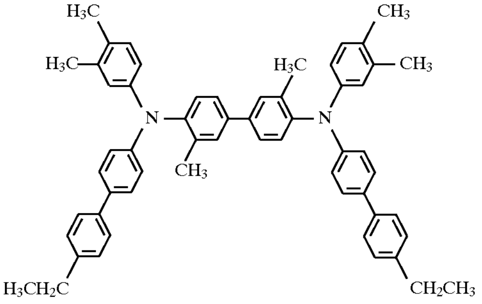

(4-5)

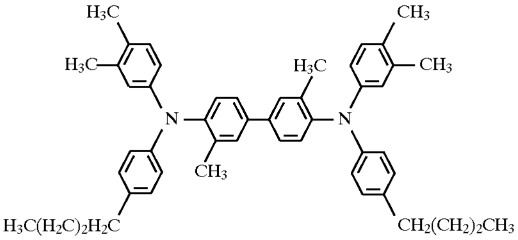

Examples of the above benzidine derivative (5) include the compounds represented by the following formulas (5-1) to (5-3):

(5-1)

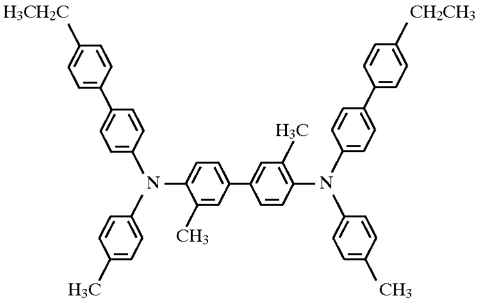

(5-2)

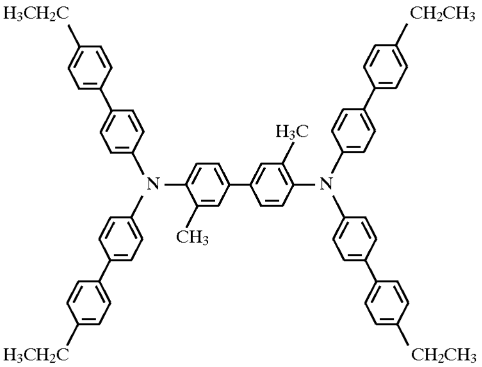

(5-3)

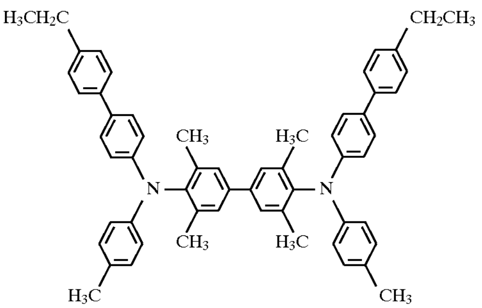

The benzidine derivative (3), (4) or (5) can be synthesized by various methods. For example, the benzidine derivative represented by the above formula (4-1) is synthesized, as shown in the following reaction scheme (VIII) and (IX). That is, N,N'-diacetyl-3,3'-dimethylbenzidine (24) is firstly mixed with 2,4-dimethyliodobenzene (25) in a proportion of 1:2 (molar ratio), together with copper powders, copper oxide or copper halide, in the presence of a basic substance to synthesize a compound (26). Then, the compound (26) is subjected to a deacetylation reaction to obtain a compound (27). Furthermore, as shown in the following reaction scheme (IX), the compound (27) is mixed with 4-ethyl-4'-iodobiphenyl (28) in a proportion of 1:2 (molar ratio) and then the mixture is reacted according to the same manner as that described above to synthesize a benzidine derivative represented by the formula (4-1).

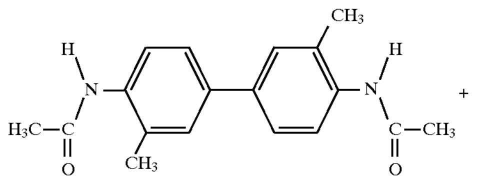

(24)

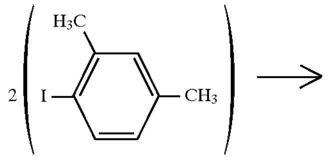

(25)

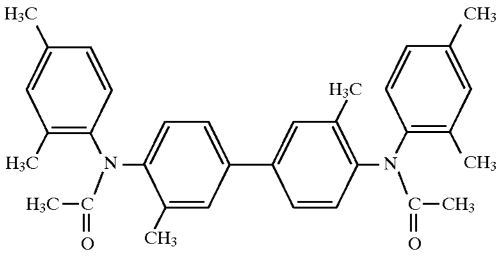

(26)

Reaction scheme (IX):

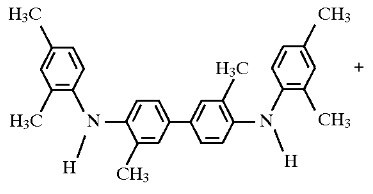

(27)

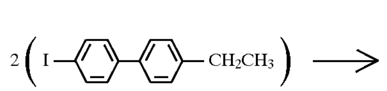

(28)

-continued

Reaction scheme (IX):

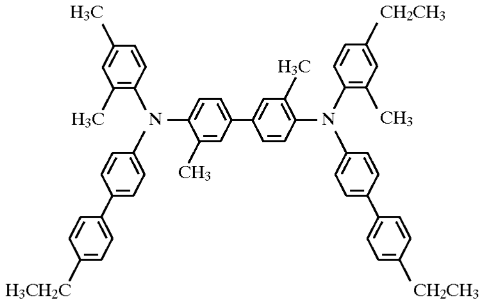

The above benzidine derivatives (3) to (5) have a high melting point. Accordingly, an electrophotosensitive material having sufficiently high glass transition temperature can be obtained by using at least one of these benzidine derivatives (3) to (5) as the hole transferring material.

In addition, as the hole transferring material in the present invention, those having an ionization potential of 4.8 to 5.8 eV are preferred. Particularly, those having a mobility of not less than $1\times10^{-6}$ $cm^2/V.s$ at an electric field strength of $3\times10^5$ V/cm are more preferred.

In the electrophotosensitive material of the present invention, the residual potential can be further lowered to improve the sensitivity by using a hole transferring material having the ionization potential within the above range. The reason is not clear necessarily, but is considered as follows.

That is, an ease of injecting electric charges from the electric charge generating material into the hole transferring material has a close relation with the ionization potential of the hole transferring material. When the ionization potential of the hole transferring material is larger than the above range, the degree of injection of electric charges from the electric charge generating material into the hole transferring material becomes low, or the degree of the giving and receiving of holes between hole transferring materials becomes low, which results in deterioration of the sensitivity.

On the other hand, in the system wherein the hole transferring material and electron transferring material coexist, it is necessary to pay attention to an interaction between them, more particularly formation of a charge transfer complex. When such a complex is formed between them, a recombination arises between holes and electron, which results in deterioration of the mobility of electric charges on the whole. When the ionization potential of the hole transferring material is smaller than the above range, a tendency to form a complex between the hole transferring material and electron transferring material becomes large and a recombination between electrons and holes arises. Therefore, an apparent yield of quantums is lowered, which results in deterioration of the sensitivity. In such a system, it is preferred to use a compound, wherein a bulky substituent is introduced, as the electron transferring material to inhibit a complex from forming between the electron transferring material and hole transferring material due to the substituent's steric hindrance. Therefore, it can be said to be preferred to use the compound (1) of the present invention, which is bulky in comparison with diphenoquinones.

When using the above compound of the general formula (2) as a hole transferring material in combination with the compound of the general formula (1) as an electron transferring material, there is a considerably little fear that a charge transfer complex is formed between them. However, it is possible to sufficiently exclude a fear of forming a complex by introducing a substituent, which is as bulky as possible, into the compound of the above general formula (1) and/or compound of the general formula (2).

The electrophotosensitive material, wherein a binding resin in the photosensitive layer contains at least an electric charge generating material, an electron transferring material of the nitrated tryptoanthrinimine derivative (1) and a hole transferring material of the phenylenediamine derivative (2), of the present invention has an excellent sensitivity and is also superior in wear resistance of the surface of the photosensitive layer.

When the electron acceptive compound having a redox potential of −0.8 to −1.4 V is contained in the photosensitive layer of the present invention, electrons are efficiently drawn from the electric charge generating material, thereby further improving the sensitivity of the photosensitive material.

In the single-layer type and multi-layer type electrophotosensitive materials, the sensitivity of the photosensitive material is improved by containing the electron acceptive compound having a redox potential of −0.8 to −1.4 V. The reason is considered as follows.

The electric charge generating material, which absorbed light in the exposure process, forms an ion pair, i.e. holes (+) and electrons (−). In order that this formed ion pair becomes a free carrier to cancel a surface electric charge effectively, it is preferred that there is not much possibility that the ion pair will recombine to disappear. In this case, when the electron acceptive compound having a redox potential of −0.8 to −1.4 V exists, the energy level of LUMO (which means the orbital of which energy level is most low in molecular orbitals containing no electrons, and the excited electrons normally transfer to this orbital) in the electron acceptive compound is lower than that of the electric charge generating material. Therefore, electrons transfer to the electron acceptive compound when the ion pair is formed, and the ion pair is liable to separate into the carrier. That is, the electron acceptive compound acts on the generation of electric charges to improve the generation efficiency.

Furthermore, it is also necessary to cause no carrier trapping due to impurities at the time of transferring of the free carrier so that the photosensitive material may have a high sensitivity. Normally, a trapping due to a small amount of impurities exist in the transfer process of the free carrier, and the free carrier transfers while causing trapping-detrapping repeatedly. Accordingly, when the free carrier is fallen into the level where detrapping can not be effected, carrier trapping arises and it's transfer is stopped.

When using the electron acceptive compound having a redox potential of more than −0.8 V (i.e. having a large electron affinity), the separated free carrier is fallen into the level where detrapping can not be effected to cause carrier trapping. To the contrary, in case of the electron acceptive compound having a redox potential of less than −1.4 V, the energy level of LUMO becomes higher than that of the electric charge generating material. When the ion pair is formed, no electrons are transferred to the electron acceptive compound, which fails to improve the electric charge-generating efficiency.

The above redox potential will be measured by means of a three-electrode system cyclic voltametry using the following materials.

Electrode: Work electrode (glassy carbon electrode),

Counter electrode (platinum electrode)

Reference electrode: silver nitrate electrode (0.1N $AgNO_3$—$CH_3CN$ solution)

Measuring solution:

Solvent: $CH_2Cl_2$ (1 litter)

Measuring substance: electron acceptive compound (0.001 mol)

Electrolyte: tetra-n-butylammonium perchlorate (0.1 mol)

The above materials are mixed to prepare a measuring solution.

Calculation of redox potential: As shown in FIG. 1, a relation between the tractive voltage (V) and current (μA) is determined to measure $E_1$ and $E_2$ shown in the same figure, then the redox potential is determined according to the following calculation formula:

$$\text{Redox potential}=(E_1+E_2)/2 \text{ (V)}$$

The electron acceptive compound which can be used in the present invention may be a compound which has electron acceptive properties and a redox potential of −0.8 to −1.4 V, but otherwise is not specifically limited. Examples thereof include benzoquinone compounds, naphthoquinone compounds, anthraquinone compounds (e.g. nitroanthraquinone, dinitroanthraquinone, etc.), diphenoquinone compounds, thiopyran compounds, fluorenone compounds (e.g. 3,4,5,7-tetranitro-9-fluorenone, etc.), xanthene compounds (e.g. 2,4,8-trinitrothioxanthene, etc.), dinitroanthracene, dinitroacridine, malononitrile, etc. Among them, the diphenoquinoine compounds are particularly preferred because a quinone oxygen atom having excellent electron attractive properties is bonded to the molecular chain terminal end and a conjugate double bond exists along with the whole long molecular chain, thereby facilitating electron transfer in the molecule as well as giving and receiving of electrons between molecules. In addition, the above respective electron acceptive compounds also contribute to the generation of electric charges.

Examples of the above benzoquinone compound include p-benzoquinone, 2,6-dimethyl-p-benzoquinone, 2,6-di-t-butyl-p-benzoquinone (Bu-BQ), etc. In addition, the diphenoquinone compound is represented by the general formula (29):

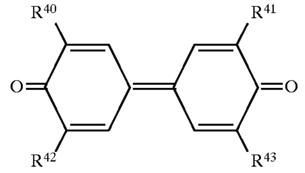

(29)

wherein $R^{40}$, $R^{41}$, $R^{42}$ and $R^{43}$ are the same or different and indicate a hydrogen atom, an alkyl group which may have a substituent, an alkoxy group which may have a substituent, an aryl group which may have a substituent, an aralkyl group which may have a substituent, a cycloalkyl group which may have a substituent or an amino group which may have a substituent, provided that two substituents of $R^{40}$, $R^{41}$, $R^{42}$ and $R^{43}$ are the same groups, and examples thereof include 3,3',5,5'-tetramethyl-4,4'-diphenoquinone, 3,3',5,5'-tetraethyl-4,4'-diphenoquinone, 3,3',5,5'-tetra-t-butyl-4,4'-diphenoquinone (Bu-DPQ), 3,5-dimethyl-3',5'-di-t-butyl-4,4'-diphenoquinone (MeBu-DPQ), 3,3'-dimethyl-5,5'-di-t-butyl-4,4'-diphenoquinone, 3,5'-dimethyl-3',5-di-t-butyl-4,4'-diphenoquinone, etc. These diphenoquinone compounds can be used alone or in combination thereof.

Examples of the electric charge generating material in the present invention include phthalocyanine pigments, naphthalocyanine pigments, azo pigments, bisazo pigments, anthanthrone pigments, indigo pigments, triphenylmethane pigments, threne pigments, toluidine pigments, pyrazoline pigments, quinacridone pigments, dithioketopyrrolopyrrole pigments, selenium, selenium-tellurium, amorphous silicon, pyrilium salt, perylene pigments, etc.

Examples of the electric charge generating material include the compounds represented by the following general formulas (CG1) to (CG12):

(CG1) Metal-free phthalocyanine ($PcH_2$), (CG1)

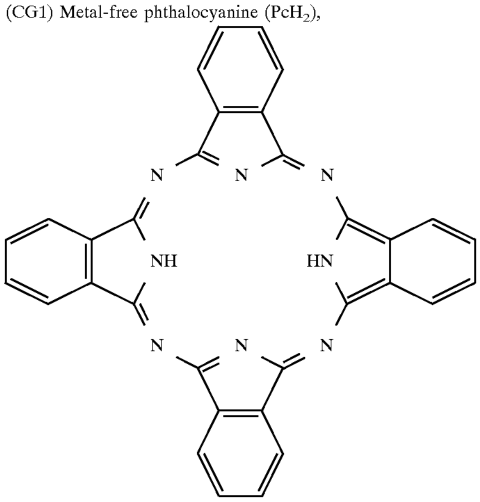

(CG2) Titanyl phthalocyanine (PcTiO), (CG2)

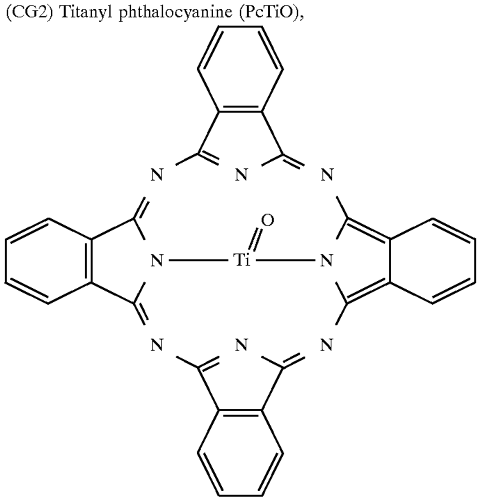

(CG3) Perylene pigment, (CG3)

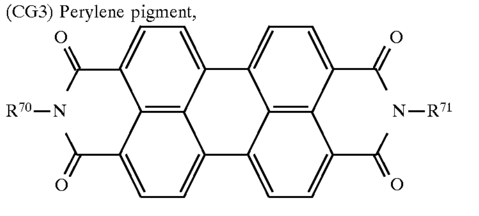

wherein $R^{70}$ and $R^{71}$ are the same or different and indicate a substituted or non-substituted alkyl, cycloalkyl, aryl, alkanoyl or aralkyl group having carbon atoms of not more than 18, (CG4) Bisazo pigment $$A^1—N=N—X—N=N—A^2 \qquad (CG4)$$

wherein $A^1$ and $A^2$ are the same or different and indicate a coupler residue; X indicates

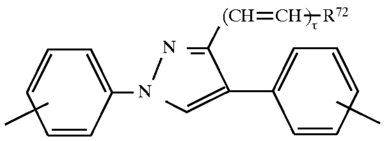

(wherein $R^{72}$ is a hydrogen atom, an alkyl group, an aryl group or a heterocyclic group, and the alkyl group, aryl group or heterocyclic group may have a substituent; and τ is 0 or 1),

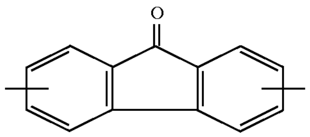

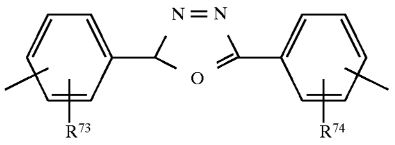

(wherein $R^{73}$ and $R^{74}$ are the same or different and indicate a hydrogen atom, an alkyl group having 1 to 5 carbon atoms, a halogen atom, an alkoxy group, an aryl group or an aralkyl group),

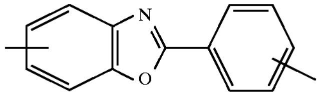

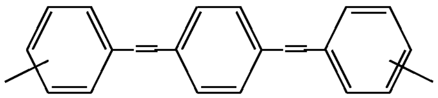

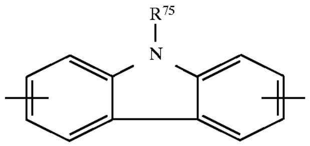

(wherein $R^{75}$ is a hydrogen atom, an ethyl group, a chloroethyl group or a hydroxyethyl group),

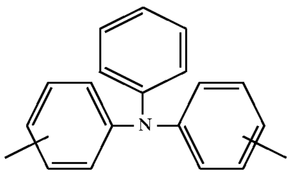

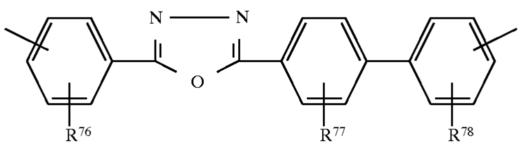

(wherein $R^{76}$, $R^{77}$ and $R^{78}$ are the same or different and indicate a hydrogen atom, an alkyl group having 1 to 5 carbon atoms, a halogen atom, an alkoxy group, an aryl group or an aralkyl group, (CG5)

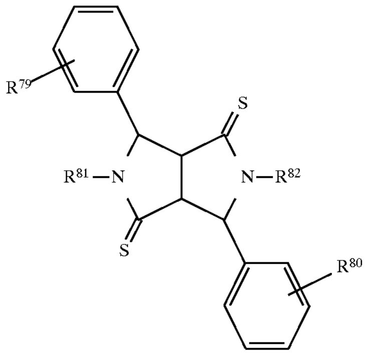

wherein $R^{79}$ and $R^{80}$ are the same or different and indicate a hydrogen atom, an alkyl group, an alkoxy group or a halogen atom; and $R^{81}$ and $R^{82}$ are the same or different and indicate a hydrogen atom, an alkyl group or an aryl group, (CG6) Metal-free naphthalocyanine pigment (CG6)

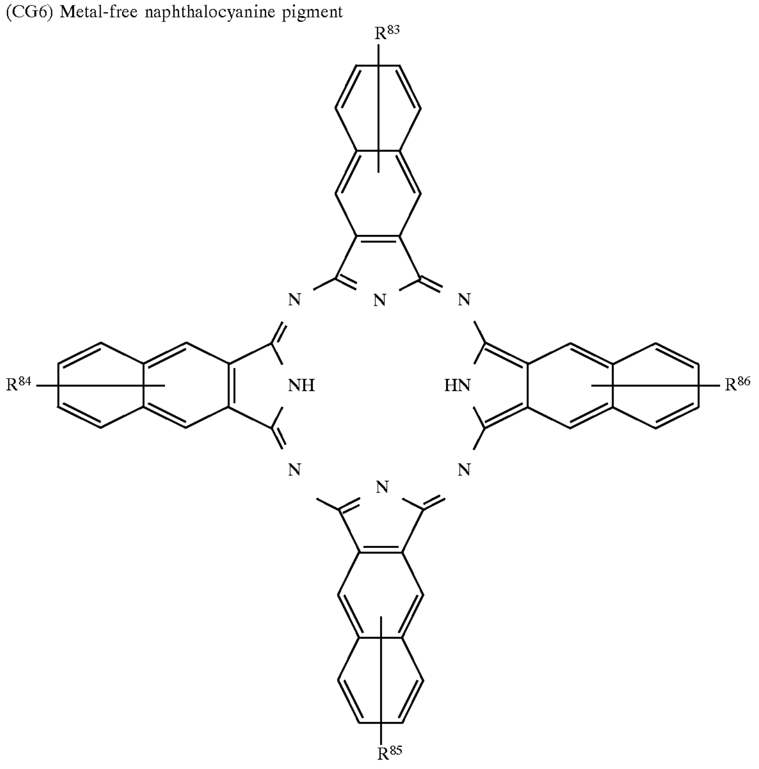

wherein $R^{83}$, $R^{84}$, $R^{85}$ and $R^{86}$ are the same or different and indicate a hydrogen atom, an alkyl group, an alkoxy group or a halogen atom, (CG7) Metal naphthalocyanine pigment (CG7)

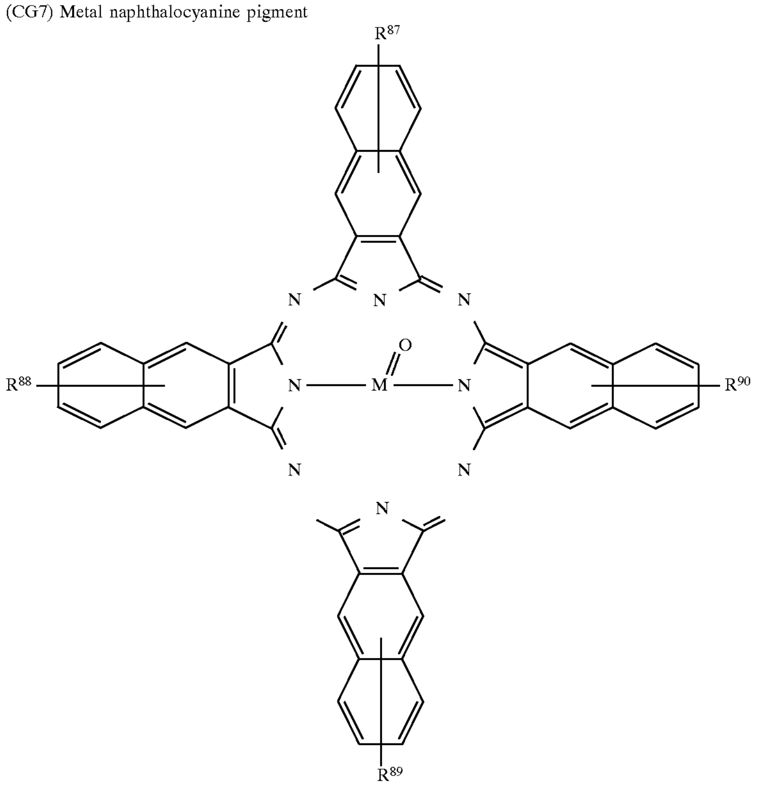

wherein $R^{87}$, $R^{88}$, $R^{89}$ and $R^{90}$ are the same or different and indicate a hydrogen atom, an alkyl group, an alkoxy group or a halogen atom; and M is Ti or V, (CG8) Squaraine pigment (CG8)

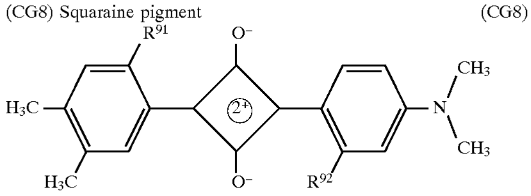

wherein $R^{91}$ and $R^{92}$ are the same or different and indicate a hydrogen atom, an alkyl group, an alkoxy group or a halogen atom, (CG9) Trisazo pigment (CG9)

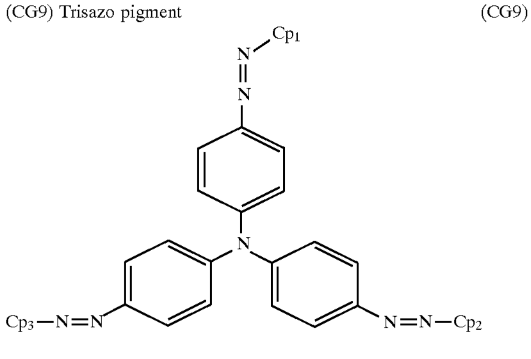

wherein $Cp_1$, $Cp_2$ and $Cp_3$ are the same or different and indicate a coupler residue, (CG10) Indigo pigment (CG10)

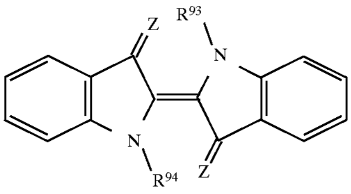

wherein $R^{93}$ and $R^{94}$ are the same or different and indicate a hydrogen atom, an alkyl group or an aryl group; and Z is an oxygen atom or a sulfur atom, (CG11)

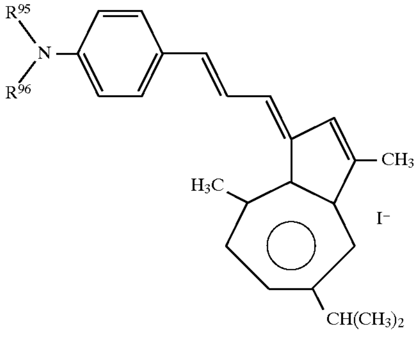

wherein $R^{95}$ and $R^{96}$ are the same or different and indicate a hydrogen atom, an alkyl group or an aryl group, and

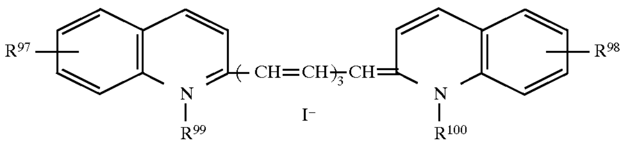
(CG12)

wherein $R^{97}$ and $R^{98}$ are the same or different and indicate a hydrogen atom, an alkyl group, an alkoxy group or a halogen atom; and $R^{99}$ and $R^{100}$ are the same or different and indicate a hydrogen atom, an alkyl group or an aryl group.

In the above electric charge generating material, examples of the alkyl group include the same groups as those described above. The alkyl group having 1 to 5 carbon atoms is that in which a hexyl group is excluded from the above alkyl group having 1 to 6 carbon atoms. The substituted or non-substituted alkyl group having carbon atoms of not more than 18 is a group including octyl, nonyl, decyl, dodecyl, tridecyl, pentadecyl, octadecyl, etc., in addition to the above alkyl group having 1 to 6 carbon atoms. Examples of the cycloalkyl group include groups having 3 to 8 carbon atoms, such as cyclopropyl group, cyclobutyl group, cyclopentyl, cyclohexyl, cycloheptyl, cyclooctyl, etc. Examples of the alkoxy group, aryl group and aralkyl group include the same group as those described above. Examples of the alkanoyl group include formyl, acetyl, propionyl, butyryl, pentanoyl, hexanoyl, etc.

Examples of the heterocyclic group include thienyl, pyrrolyl, pyrrolidinyl, oxazolyl, isoxazolyl, thiazolyl, isothiazolyl, imidazolyl, 2H-imidazolyl, pyrazolyl, triazolyl, tetrazolyl, pyranyl, pyridyl, piperidyl, piperidino, 3-morpholinyl, morpholino, thiazolyl, etc. In addition, it may be a heterocyclic group condensed with an aromatic ring.

Examples of the substituent which may be substituted on the above group include halogen atom, amino group, hydroxyl group, optionally esterified carboxyl group, cyano group, alkyl group having 1 to 6 carbon atoms, alkoxy group having 1 to 6 carbon atoms, alkenyl group having 2 to 6 carbon atoms which may have an aryl group, etc.

Examples of the coupler residue represented by $A^1$, $A^2$, $Cp_1$, $Cp_2$ and $Cp_3$ include the groups shown in the following formulas (121) to (127):

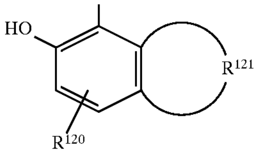
(121)

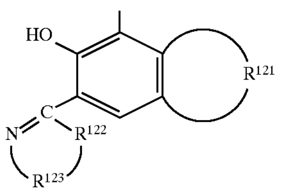
(122)

-continued

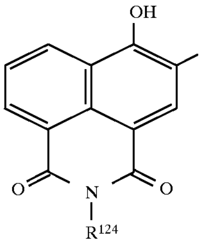
(123)

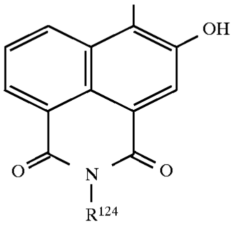
(124)

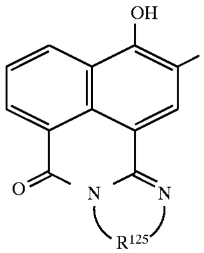
(125)

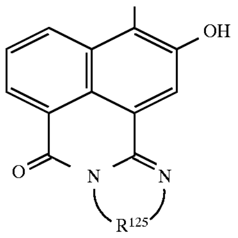
(126)

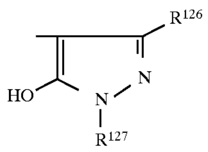
(127)

In the respective formulas, $R^{120}$ is a carbamoyl group, a sulfamoyl group, an allophanoyl group, oxamoyl group, anthraninoyl group, carbazoyl group, glycyl group, hydantoyl group, phthalamoyl group or a succinamoyl group. These groups may have substituents such as halogen atom, phenyl group which may have a substituent, naphthyl group which may have a substituent, nitro group, cyano group, alkyl group, alkenyl group, carbonyl group, carboxyl group, etc.

$R^{121}$ is an atomic group which is required to form an aromatic ring, a polycyclic hydrocarbon or a heterocycle by condensing with a benzene ring, and these rings may have the same substituent as that described above.

$R^{122}$ is an oxygen atom, a sulfur atom or an imino group.

$R^{123}$ is a divalent chain hydrocarbon or aromatic hydrocarbon group, and these groups may have the same substituent as that described above.

$R^{124}$ is an alkyl group, an aralkyl group, an aryl group or a heterocyclic group, and these groups may have the same substituent as that described above.

$R^{125}$ is a divalent chain hydrocarbon or aromatic hydrocarbon group, or an atomic group which is required to form a heterocycle, together with a moiety represented by the following formula:

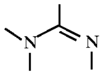
(30)

in the above general formulas (125) and (126), and these rings may have the same substituent as that described above.

$R^{126}$ is a hydrogen atom, an alkyl group, an amino group, a carbamoyl group, a sulfamoyl group, an allophanoyl group, a carboxyl group, an alkoxycarbonyl group, an aryl group or a cyano group, and the groups other than a hydrogen atom may have the same substituent as that described above.

$R^{127}$ is an alkyl or an aryl group, and these groups may have the same substituent as that described above.

Examples of the alkenyl group include alkenyl groups having 2 to 6 carbon atoms, such as vinyl, allyl, 2-butenyl, 3-butenyl, 1-methylallyl, 2-pentenyl, 2-hexenyl, etc.

In the above $R^{121}$, examples of the atomic group which is required to form an aromatic ring by condensing with a benzene ring include alkylene groups such as methylene, ethylene, trimethylene, tetramethylene, etc.

Examples of the aromatic ring to be formed by condensing the above $R^{121}$ with a benzene ring include naphthalene, anthracene, phenanthrene, pyrene, chrysene, naphthacene, etc.

In the above $R^{121}$, examples of the atomic group which is required to form a polycyclic hydrocarbon by condensing with a benzene ring include alkylene groups having 1 to 4 carbon atoms, such as methylene, ethylene, propylene, butyrene, etc.

In the above $R^{121}$, examples of the polycyclic hydrocarbon to be formed by condensing with a benzene ring include carbazole ring, benzocarbazole ring, dibenzofuran ring, etc.

In the above $R^{121}$, examples of the atomic group which is required to form a heterocycle by condensing with a benzene ring include benzofuryl, benzothiophenyl, indolyl, 1H-indolyl, benzoxazolyl, benzothiazolyl, 1H-indadolyl, benzoimidazolyl, chromenyl, chromanyl, isochromanyl, quinolyl, isoquinolyl, cinnolinyl, phthalazinyl, quinazolinyl, quinoxalinyl, dibenzofryl, carbazolyl, xanthenyl, acridinyl, phenanthridinyl, phenazinyl, phneoxazinyl, thianthrenyl, etc.

Examples of the aromatic heterocyclic group to be formed by condensing the above $R^{121}$ and the benzene ring include thienyl, furyl, pyrrolyl, oxazolyl, isoxazolyl, thiazolyl, isothiazolyl, imidazolyl, pyrazolyl, triazolyl, tetrazolyl, pyridyl, thiazolyl, etc. In addition, it may also be a heterocyclic group condensed with the other aromatic ring (e.g. benzofuryl, benzoimidazolyl, benzoxazolyl, benzothiazolyl, quinolyl, etc.).

In the above $R^{123}$ and $R^{125}$, examples of the divalent chain hydrocarbon include ethylene, propylene, tetramethylene, etc. Examples of the divalent aromatic hydrocarbon include phenylene, naphthylene, phenanthrylene group, etc.

In the above $R^{124}$, examples of the heterocyclic group include pyridyl group, pyrazinyl group, thienyl group, pyranyl group, indolyl group, etc.

In the above $R^{125}$, examples of the atomic group which is required to form a heterocycle, together with the moiety represented by the above formula (30), include phenylene, naphthylene, phenanthrylene, ethylene, propylene, tetramethylene group, etc.

Examples of the aromatic heterocyclic group to be formed by the above $R^{125}$ and moiety represented by the above formula (30) include benzoimidazole, benzo[f]benzoimidazole, dibenzo[e,g]benzoimidazole, benzopyrimidine, etc. These groups may have the same group as that described above.

In the above $R^{126}$, examples of the alkoxycarbonyl group include methoxycarbonyl, ethoxycarbonyl, propoxycarbonyl, butoxycarbonyl, etc.

In the present invention, there can be used electric charge generating material which have hitherto been known, such as selenium, selenium-tellurium, amorphous silicon, pyrilium salt, anthanthrone pigments, triphenylmethane pigments, threne pigments, toluidine pigments, pyrazoline pigments, quinacridone pigments, etc., in addition to the above electric charge generating materials.

The above electric charge generating materials can be used alone or in combination thereof to present an absorption wavelength within a desired range. In that case, it is preferred to use a charge generating material (CGM) having the ionization potential which is balanced with that of the hole transferring material (HTM) in connection with using the HTM having the ionization potential of 4.8 to 5.8 eV, for example, the CGM having the ionization potential of 4.8 to 5.8 eV, particularly 5.0 to 5.8 eV, in view of a decrease in residual potential and an improvement of the sensitivity.

Among the above electric charge generating materials, X-type metal-free phthalocyanine, oxotitanyl phthalocyanine, perylene pigment, etc. are superior in matching with the compound (electron transferring material) represented by the general formula (1), (6) or (7) of the present invention. Therefore, an electrophotosensitive material using both in combination is superior in sensitivity.

The phthalocyanine pigments such as X-type metal-free phthalocyanine, oxotitanyl phthalocyanine, etc. are particularly suitable for a digital-optical image forming apparatus using a light source having a wavelength of 700 nm or more. In addition, the above perylene pigment is suitable for an analog-optical image forming apparatus using a light source having a wavelength of a visible range.

Among the perylene pigments of the above general formula (CG3), a perylene pigment represented by the general formula (31):

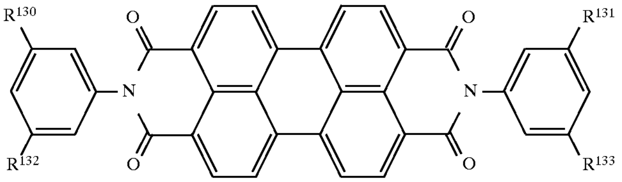
(31)

wherein $R^{130}$, $R^{131}$, $R^{132}$ and $R^{133}$ are the same or different and indicate a hydrogen atom, an alkyl group, an alkoxy group or an aryl group is suitably used.

In the above general formula (31), examples of the alkyl, alkoxy and aryl group, which correspond to the substituents $R^{130}$ to $R^{133}$ include the same groups as those described above.

This perylene pigment is suitable as the electric charge generating material of the photosensitive material having a sensitivity at the visible range. That is, the above perylene pigment (31) is superior in matching with the compound (electron transferring material) represented by the general formula (1). Therefore, the electrophotosensitive material using both in combination has a high sensitivity at the visible range and it can be suitably used for an analog-optical image forming apparatus using a light source having a wavelength of the visible range.

Examples of the electric charge generating material which can be used in the present invention include the compounds represented by the following formulas (12-1) to (12-7), in addition to the compounds represented by the above formulas (CG1), (CG2) and (31).

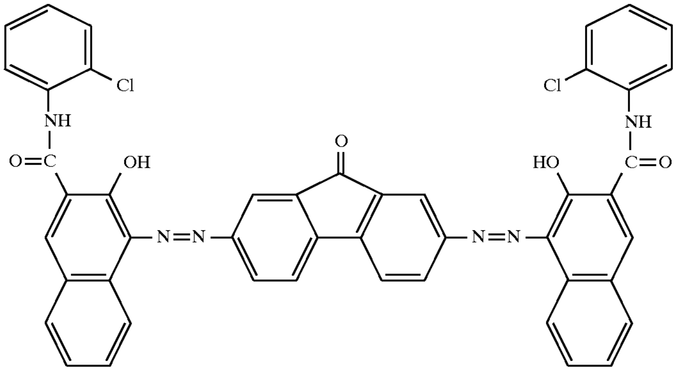
(12-1)

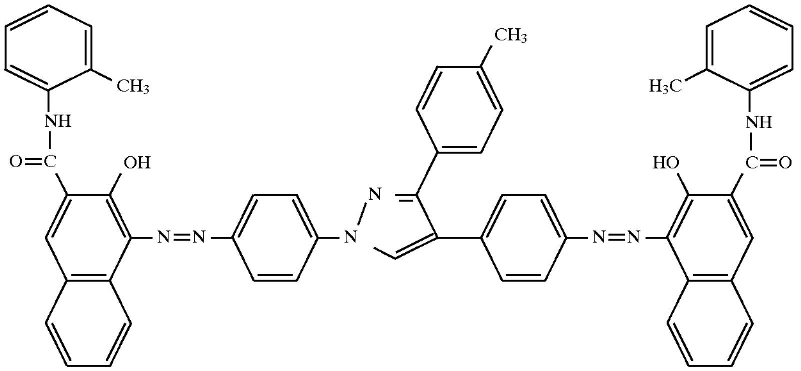
(12-2)

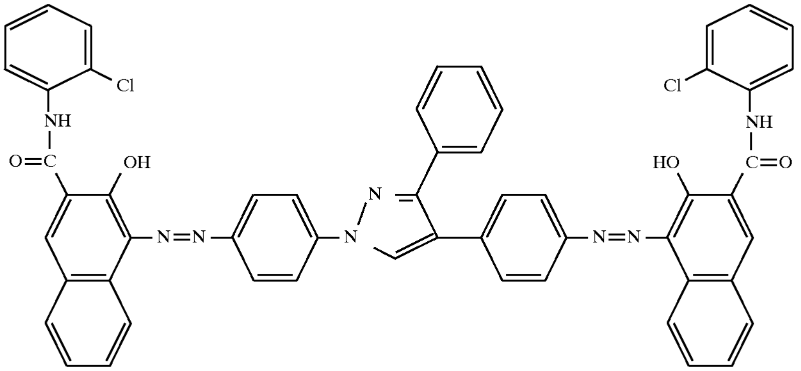
(12-3)

-continued

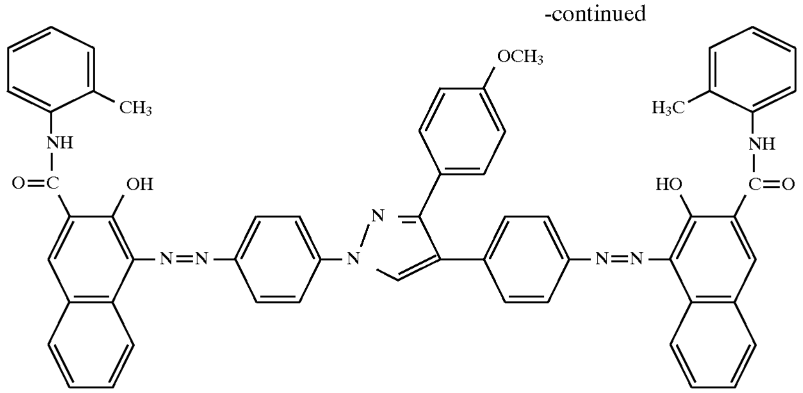

(12-4)

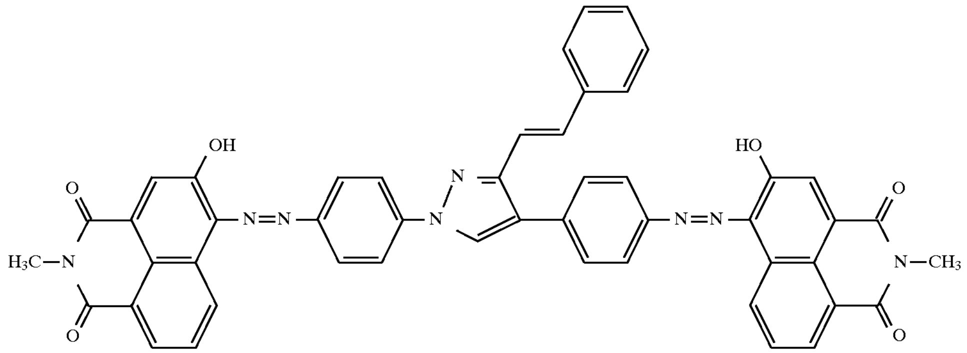

(12-5)

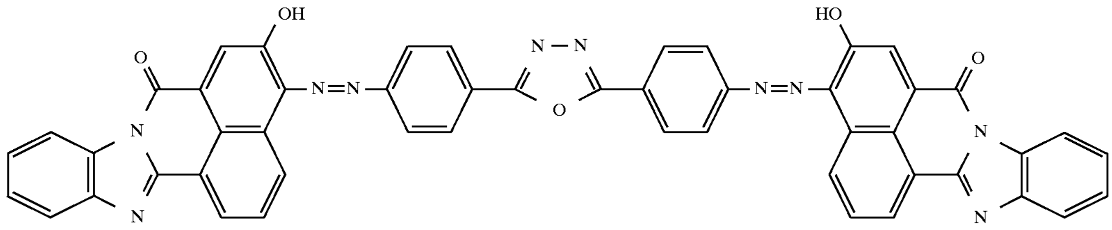

(12-6)

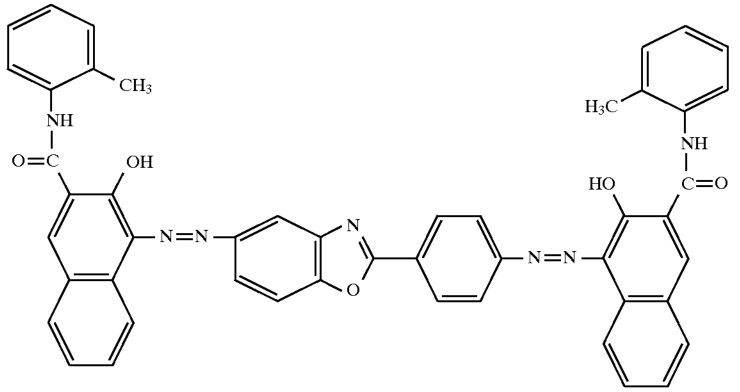

(12-7)

As the binding resin for dispersing the above respective components, there can be used various resins which have hitherto been used for the organic photosensitive layer, and examples thereof include thermoplastic resins such as styrene polymer, styrene-butadiene copolymer, styrene-acrylonitrile copolymer, styrene-maleic acid copolymer, acrylic copolymer, styrene-acrylic acid copolymer, polyethylene, ethylene-vinyl acetate copolymer, chlorinated polyethylene, polyvinyl chloride, polypropylene, ionomer, vinyl chloride-vinyl acetate copolymer, polyester, alkyd resin, polyamide, polyurethane, polycarbonate, polyarylate, polysulfon, diaryl phthalate resin, ketone resin, polyvinyl butyral resin, polyether resin, polyester resin, etc.; crosslinking thermosetting resins such as silicone resin, epoxy resin, phenol resin, urea resin, melamine resin, etc.; photosetting resins such as epoxy acrylate, urethane acrylate, etc. These binding resins can be used alone or in combination thereof. Among the above resins, styrene polymer, acrylic polymer, styrene-acrylic copolymer, polyester, alkyd resin, polycarbonate, polyarylate, etc. are suitably used.

Further, various electron transferring materials having a high electron transferring capability may be contained in the photosensitive layer, together with the compounds represented by the above general formulas (1), (6) and (7).

In addition to the above diphenoquinone compound and benzoquinone compound, examples of the electron transferring material include the compounds represented by the following general formulas (ET1) to (ET12):

(ET1)

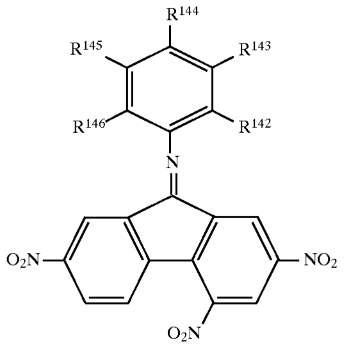

wherein $R^{142}$, $R^{143}$, $R^{144}$, $R^{145}$ and $R^{146}$ are the same or different and indicate a hydrogen atom, an alkyl group which may have a substituent, an alkoxy group which may have a substituent, an aryl group which may have a substituent, an aralkyl group which may have a substituent, or a halogen atom, (ET2)

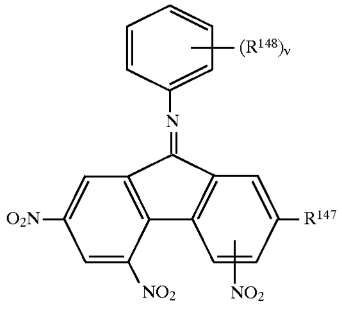

wherein $R^{147}$ is an alkyl group; $R^{148}$ is an alkyl group which may have a substituent, an alkoxy group which may have a substituent, an aryl group which may have a substituent, an aralkyl group which may have a substituent, a halogen atom or an alkyl halide group; and $\upsilon$ is an integer of 0 to 5; each $R^{148}$ may be different when $\upsilon$ is not less than 2, (ET3)

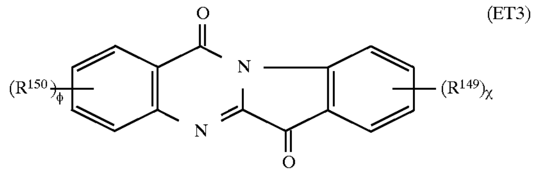

wherein $R^{149}$ and $R^{150}$ are the same or different and indicate an alkyl group; $\chi$ is an integer of 1 to 4; and $\phi$ is an integer of 0 to 4; $R^{149}$ and $R^{150}$ may be different when $\chi$ or $\phi$ are not less than 2, (ET4)

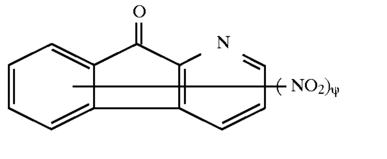

wherein $\phi$ is an integer of 1 to 2, (ET5)

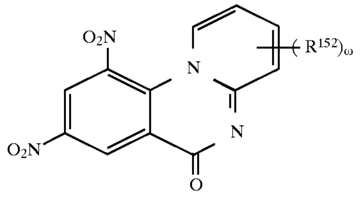

wherein $R^{152}$ is an alkyl group; and $\omega$ is an integer of 1 to 4; each $R^{152}$ may be different when $\omega$ is not less than 2, (ET6)

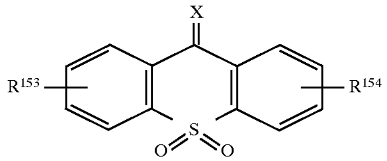

wherein $R^{153}$ and $R^{154}$ are the same or different and indicate a hydrogen atom, a halogen atom, an alkyl group, an aryl group, an aralkyloxycarbonyl group, an alkoxy group, a hydroxyl group, a nitro group or a cyano group; and X is a group of O, —N—CN or—C(CN)$_2$, (ET7)

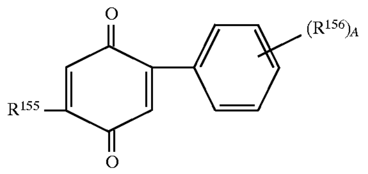

wherein $R^{155}$ is a hydrogen atom, a halogen atom, an alkyl group, or a phenyl group which may have a substituent; $R^{156}$ is a hydrogen atom, a halogen atom, an alkyl group which may have a substituent, a phenyl group which may have a substituent, an alkoxycarbonyl group, a N-alkylcarbamoyl group, a cyano group or a nitro group; and A is an integer of 1 to 3; each $R^{156}$ may be different when A is not less than 2, (ET8)

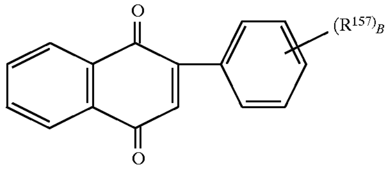

wherein $R^{157}$ is a hydrogen atom, an alkyl group which may have a substituent, a phenyl group which may have a substituent, a halogen atom, an alkoxycarbonyl group, a N-alkylcarbamoyl group, a cyano group or a nitro group; and B is an integer of 1 to 3; each $R^{157}$ may be different when B is not less than 2, (ET9)

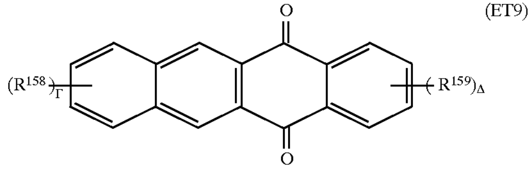

wherein $R^{158}$ and $R^{159}$ are the same or different and indicate a hydrogen atom, a halogen atom, an alkyl group which may have a substituent, a cyano group, a nitro group or an alkoxycarbonyl group; and $\Gamma$ and $\Delta$ indicate an integer of 1 to 3; $R^{158}$ and $R^{159}$ may be different when Γ or Δ is not less than 2,

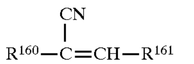

(ET10)

wherein $R^{160}$ and $R^{161}$ are the same or different and indicate a phenyl group, a polycyclic aromatic group or a heterocyclic group, and these groups may have a substituent,

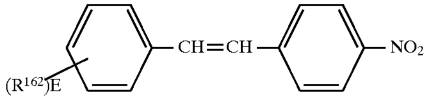

(ET11)

wherein $R^{162}$ is an amino group, a dialkylamino group, an alkoxy group, an alkyl group or a phenyl group; and E is an integer of 1 to 2; each $R^{162}$ may be different when E is 2, and

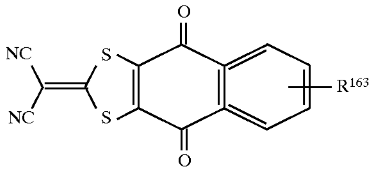

(ET12)

wherein $R^{163}$ is a hydrogen atom, an alkyl group, an aryl group, an alkoxy group or an aralkyl group. Additional examples thereof include malononitrile, thiopyran compound, tetracyanoetylene, 2,4,8-trinitrothioxanthene, dinitrobenzene, dinitroanthracene, dinitroacridine, nitroanthraquinone, dinitroanthraquinone, succinic anhydride, maleic anhydride, dibromomaleic anhydride, etc.

Examples of the polycyclic aromatic groups include napthyl, phenanthryl, anthryl, etc.

Examples of the heterocyclic group include thienyl, pyrrolyl, pyrrolidinyl, oxazolyl, isoxazolyl, thiazolyl, isothiazolyl, imidazolyl, 2H-imidazolyl, pyrazolyl, triazolyl, tetrazolyl, pyranyl, pyridyl, piperidyl, piperidino, 3-morpholinyl, morpholino, thiazolyl, etc. In addition, it may be a heterocyclic group condensed with an aromatic ring.

Examples of the substituent which may be substituted on the above group include halogen atom, amino group, hydroxyl group, optionally esterified carboxyl group, cyano group, alkyl group having 1 to 6 carbon atoms, alkoxy group having 1 to 6 carbon atoms, alkenyl group having 2 to 6 carbon atoms which may have an aryl group, etc.

In order to obtain a single-layer type electrophotosensitive material, an electric charge generating material, a hole transferring material and a binding resin etc., and further a predetermined electron transferring material may be dissolved or dispersed in a suitable solvent, and the resulting coating solution is applied on a conductive substrate using means such as application, followed by drying.

In the single-layer type photosensitive material, the electric charge generating material is blended in the amount of 0.1 to 50 parts by weight, preferably 0.5 to 30 parts by weight, based on 100 parts by weight of the binding resin. The electron transferring material is blended in the amount of 5 to 100 parts by weight, preferably 10 to 80 parts by weight, based on 100 parts by weight of the binding resin. In addition, the hole transferring material is blended in the amount of 5 to 500 parts by weight, preferably 25 to 200 parts by weight, based on 100 parts by weight of the binding resin. Furthermore, it is suitable that the total amount of the hole transferring material and electron transferring material is 10 to 500 parts by weight, preferably 30 to 200 parts by weight, based on 100 parts by weight of the binding resin. When the electron acceptive compound is contained, the amount is 0.1 to 40 parts by weight, preferably 0.5 to 20 parts by weight, based on 100 parts by weight of the binding resin.

The thickness of the single-layer type photosensitive layer is 5 to 100 μm, preferably 10 to 50 μm.

In order to obtain the multi-layer type electrophotosensitive material, an electric charge generating layer containing an electric charge generating material may be formed on a conductive substrate using means such as deposition, application, etc., and then a coating solution containing an electron transferring material and a binding resin is applied on the electric charge generating layer using means such as application, followed by drying, to form an electric charge transferring layer.

In the multi-layer photosensitive material, the electric charge generating material and binding resin, which constitute the electric charge generating layer, may be used in various proportions. It is suitable that the electric charge generating material is blended in the amount of 5 to 1,000 parts by weight, preferably 30 to 500 parts by weight, based on 100 parts by weight of the binding resin. In addition, when a tryptoanthrinimine derivative (1) is contained in the electric charge generating layer, it is suitable that this derivative (1) is blended in the amount of 0.5 to 50 parts by weight, preferably 1 to 40 parts by weight, based on 100 parts by weight of the binding resin.

The electron transferring material and binding resin, which constitute the electric charge transferring layer, can be used in various proportions within such a range as not to prevent the transfer of electrons and not to prevent the crystallization. It is suitable that the electron transferring material is used in the amount of 10 to 200 parts by weight, preferably 20 to 100 parts by weight, based on 100 parts by weight of the binding resin so as to easily transfer electrons generated by light irradiation in the electric charge generating layer.

Regarding the thickness of the multi-layer type photosensitive layer, the thickness of the electric charge generating layer is about 0.01 to 5 μm, preferably about 0.1 to 3 μm, and that of the electric charge transferring layer is 2 to 100 μm, preferably about 5 to 50 μm.

A barrier layer may be formed, in such a range as not to injure the characteristics of the photosensitive material, between the conductive substrate and photosensitive layer in the single-layer type photosensitive material, or between the conductive substrate and electric charge generating layer or between the conductive substrate layer and electric charge transferring layer in the multi-layer type photosensitive material. Further, a protective layer may be formed on the surface of the photosensitive layer.

In addition, various additives which have hitherto been known, such as deterioration inhibitors (e.g. antioxidants, radical scavengers, singlet quenchers, ultraviolet absorbers, etc.), softeners, plasticizers, surface modifiers, bulking agents, thickening agents, dispersion stabilizers, wax, acceptors, donors, etc. can be formulated in the single-layer type or multi-layer type photosensitive layer without injury to the electrophotographic characteristics. The amount of these additives to be added may be the same as that of a conventional one. For example, it is preferred that a steric hindered phenolic antioxidant is formulated in the amount of about 0.1 to 50 parts by weight, based on 100 parts by weight of the binding resin.

In order to improve the sensitivity of the photosensitive layer, known sensitizers such as terphenyl, halonaphthoquinones, acenaphthylene, etc. may be used in combination with the electric charge generating material.

In addition, other electron transferring materials which have hitherto been known can be used in combination with the compound represented by the above general formula (1). Examples of the electron transferring material include benzoquinone compounds, diphenoquinone compounds, malononitrile compounds, thiopyran compounds, tetracyanoethylene, 2,4,8-trinitrothioxanthone, fluorenone compounds (e.g. 3,4,5,7-tetranitro-9-fluorenone, etc.), dinitrobenzene, dinitroanthracene, dinitroacridine, nitroanthraquinone, dinitroanthraquinone, succinic anhydride, maleic anhydride, dibromomaleic anhydride, etc.

As the conductive substrate to be used for the electrophotosensitive material of the present invention, various materials having a conductivity can be used, and examples thereof include metals such as aluminum, copper, tin, platinum, silver, vanadium, molybdenum, chromium, cadmium, titanium, nickel, palladium, indium, stainless steel, brass, etc.; plastic materials vapor-deposited or laminated with the above metal; glass materials coated with aluminum iodide, tin oxide, indium oxide, etc.

The conductive substrate may be made in the form of a sheet or a drum. The substrate itself may have a conductivity or only the surface of the substrate may have a conductivity. It is preferred that the conductive substrate has a sufficient mechanical strength when used.

The photosensitive layer in the electrophotosensitive material of the present invention is produced by applying a coating solution, obtained by dissolving or dispersing a resin composition containing the above respective components in a suitable solvent, on a conductive substrate, followed by drying. That is, the above electric charge generating material, electric charge transferring material and binding resin etc. may be dispersed and mixed with a suitable solvent by a known method, for example, using a roll mill, a ball mill, an atriter, a paint shaker, a supersonic dispenser, etc. to prepare a dispersion, which is applied by a known means and then allowed to dry.

As the solvent for preparing the dispersion, there can be used various organic solvents, and examples thereof include alcohols such as methanol, ethanol, isopropanol, butanol, etc.; aliphatic hydrocarbons such as n-hexane, octane, cyclohexane, etc.; aromatic hydrocarbons such as benzene, toluene, xylene, etc.; hydrocarbon halides such as dichloromethane, dichloroethane, carbon tetrachloride, chlorobenzene, etc.; ethers such as dimethyl ether, diethyl ether, tetrahydrofuran, ethylene glycol dimethyl ether, diethylene glycol dimethyl ether, etc.; ketones such as acetone, methyl ethyl ketone, cyclohexanone, etc.; esters such as ethyl acetate, methyl acetate, etc.; dimethylformaldehyde, dimethylformamide, dimethyl sulfoxide, etc. These solvents may be used alone or in combination thereof.

In order to improve a dispersibility of the electric charge transferring material and electric charge generating material as well as a smoothness of the surface of the photosensitive layer, there may be used surfactants, leveling agents, etc.

EXAMPLES

Reference Example

Synthesis of 2,6-dinitrotryptoanthrine (9-1)

Tryptoanthrine (2) (20 g, 85 mmol) was added in 200 ml of a mixed acid (concentrated sulfuric acid:concentrated nitric acid=1:1) and the mixture was reacted at 40° C. for one hour. After the completion of the reaction, a crystal deposited in ice water was filtered, washed with water, dried, and then recrystallized from acetic acid to obtain 26 g of 2,6-dinitrotryptoanthrine represented by the following formula (9-1). Yield: 94%

(9-1)

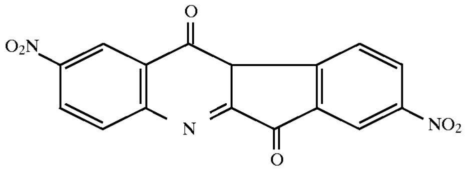

The mass spectrum m/e of the compound (9-1) was 338 ($M^+$).

Synthesis Example 1

Synthesis of N-(2'-isopropylphenyl)-2,6-dinitrotryptoanthrinimine (1-1)

2,6-Dinitrotryptoanthrine (9-1) (5 g, 15 mmol) obtained in the above Reference Example and o-isopropylaniline (2.7 g, 20 mmol) were dissolved in 50 ml of acetic acid, and the mixture was reacted under reflux for 2 hours. After the completion of the reaction, the reaction mixture was added to 400 ml of water. Then, a crystal deposited was filtered, washed with water, dried, and then purified by subjecting to silica gel chromatography (developing solvent: mixed solvent of chloroform and hexane) to obtain 4.5 g of the titled compound. Yield: 66%, Melting point: 236° C.

Figure 2:
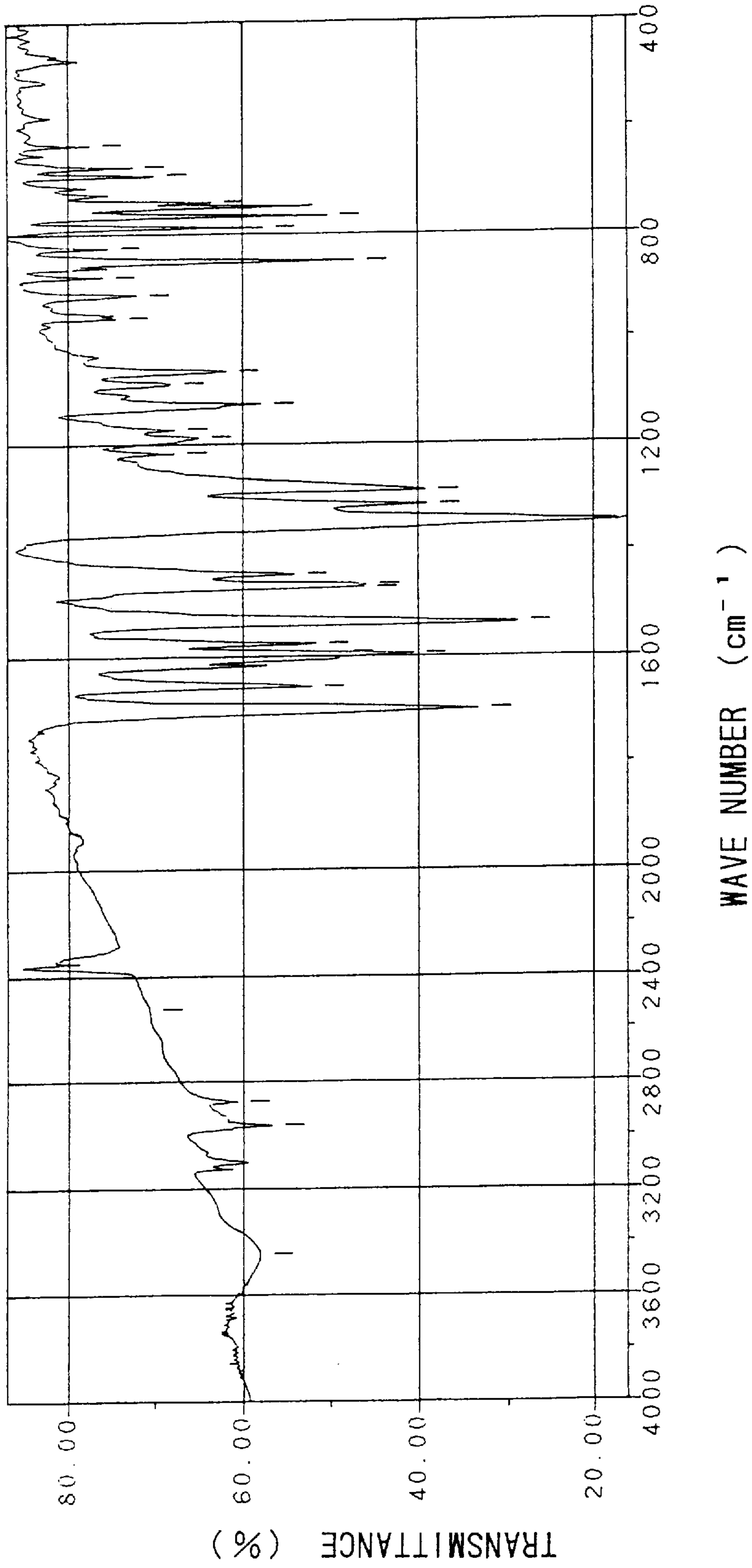
FIG. 2 to FIG. 16 are graphs showing an infrared absorption spectrum of the compound obtained in Synthetic Examples 1 to 10, 12 to 13 and 19 to 21 respectively.

The infrared absorption spectrum of the compound (1-1) is shown in FIG. 2.

Synthesis Example 2

Synthesis of N-(2-biphenylyl)-2,6-dinitrotryptoanthrinimine (1-2)

According to the same manner as that described in Synthesis Example 1 except for using 2-aminobiphenyl (3.5 g, 20 mmol) in place of o-isopropylaniline (2.7 g, 20 mmol), 4.7 g of the titled compound was obtained. Yield: 63%, Melting point: 140° C.

Figure 3:
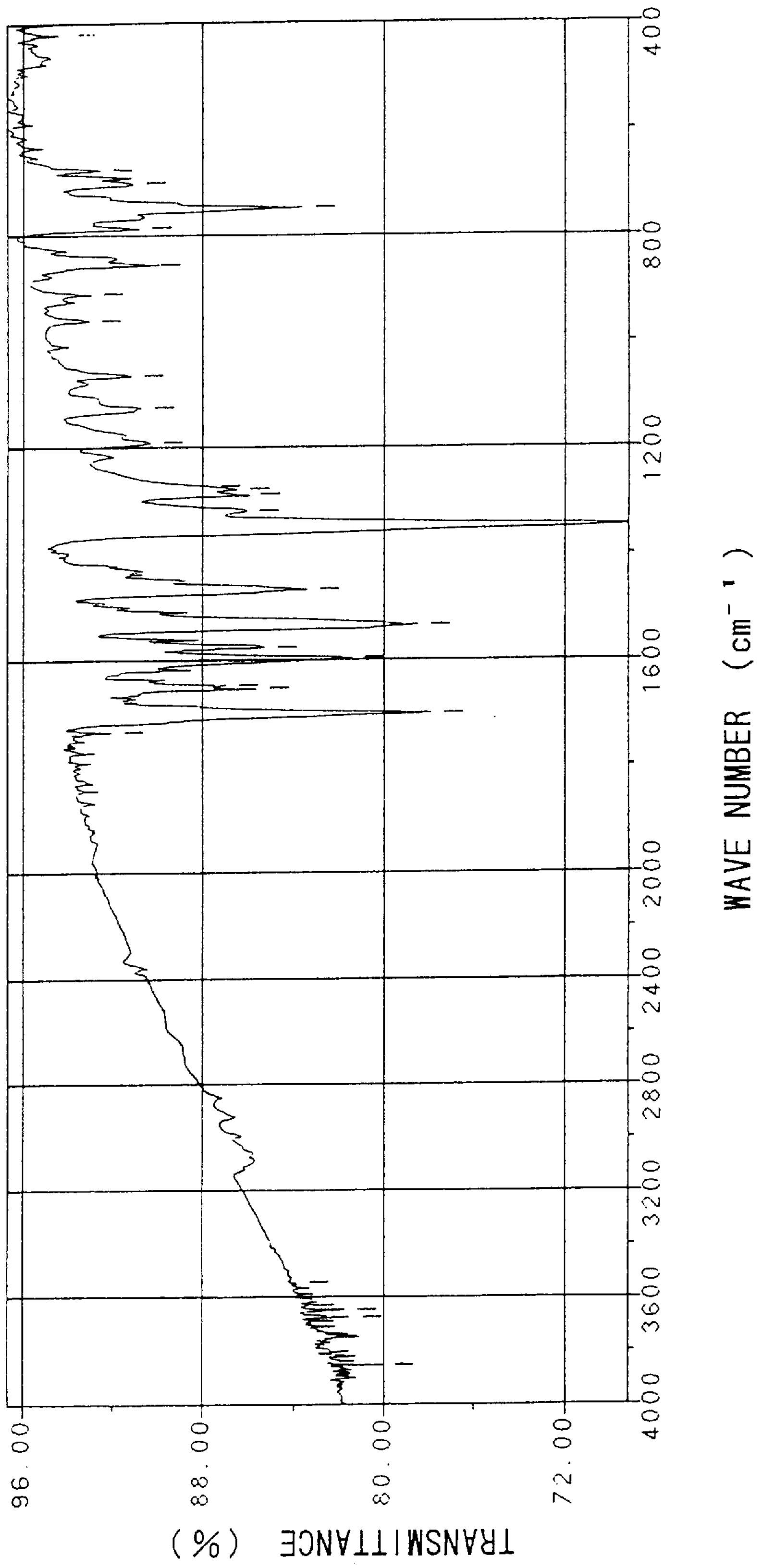

The infrared absorption spectrum of the compound (1-2) is shown in FIG. 3.

Synthesis Example 3

Synthesis of N-(2,6-dimethylphenyl)-2,6-dinitrotryptoanthrinimine (1-3)

According to the same manner as that described in Synthesis Example 1 except for using 2,6-xylidine (2.4 g, 20 mmol) in place of o-isopropylaniline (2.7 g, 20 mmol), 4.5 g of the titled compound was obtained. Yield: 68%, Melting point: 280° C. or more (decomposition)

Figure 4:
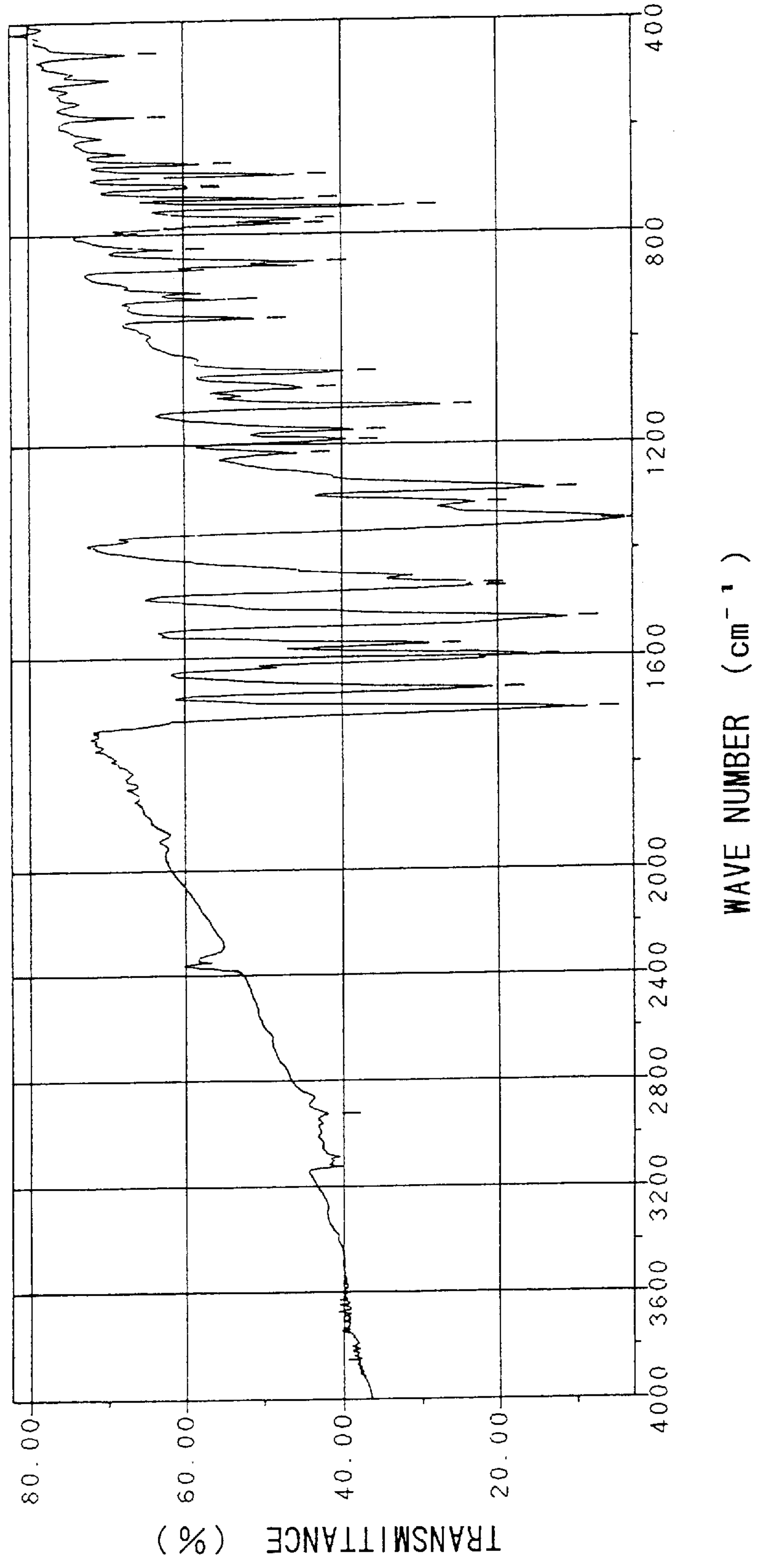

The infrared absorption spectrum of the compound (1-3) is shown in FIG. 4.

Synthesis Example 4

Synthesis of N-(2-isopropyl-6-methylphenyl)-2,6-dinitrotryptoanthrinimine (1-4)

According to the same manner as that described in Synthesis Example 1 except for using 2-isopropyl-6-methylaniline (3 g, 20 mmol) in place of o-isopropylaniline (2.7 g, 20 mmol), 4.9 g of the titled compound was obtained. Yield: 70%, Melting point: 238° C.

Figure 5:
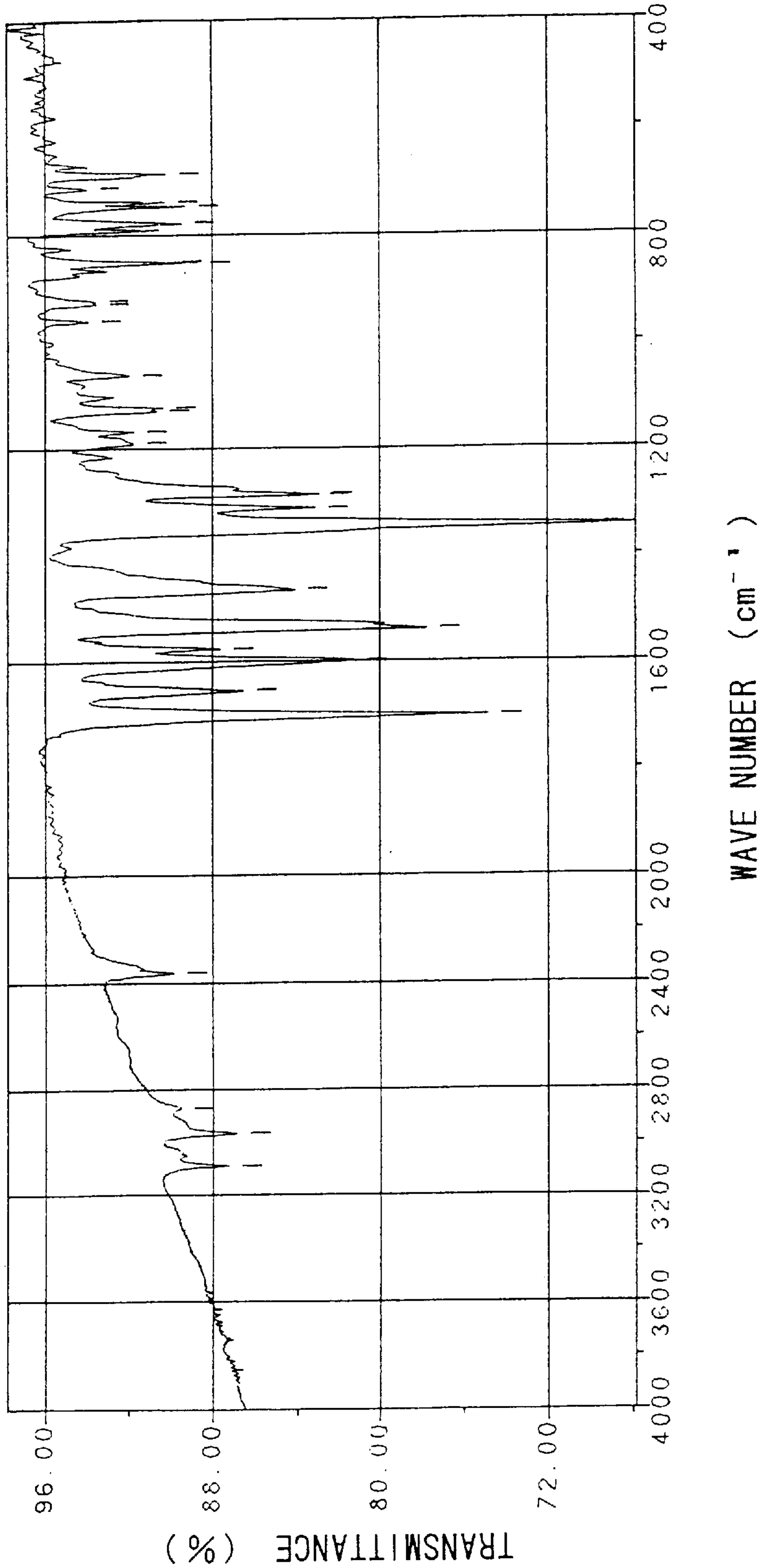

The infrared absorption spectrum of the compound (1-4) is shown in FIG. 5.

Synthesis Example 5

Synthesis of N-(2-ethyl-6-methylphenyl)-2,6-dinitrotryptoanthrinimine (1-5)

According to the same manner as that described in Synthesis Example 1 except for using 2-ethyl-6-methylaniline (2.7 g, 20 mmol) in place of o-isopropylaniline (2.7 g, 20 mmol), 5.0 g of the titled compound was obtained. Yield: 74%, Melting point: 147° C.

Figure 6:
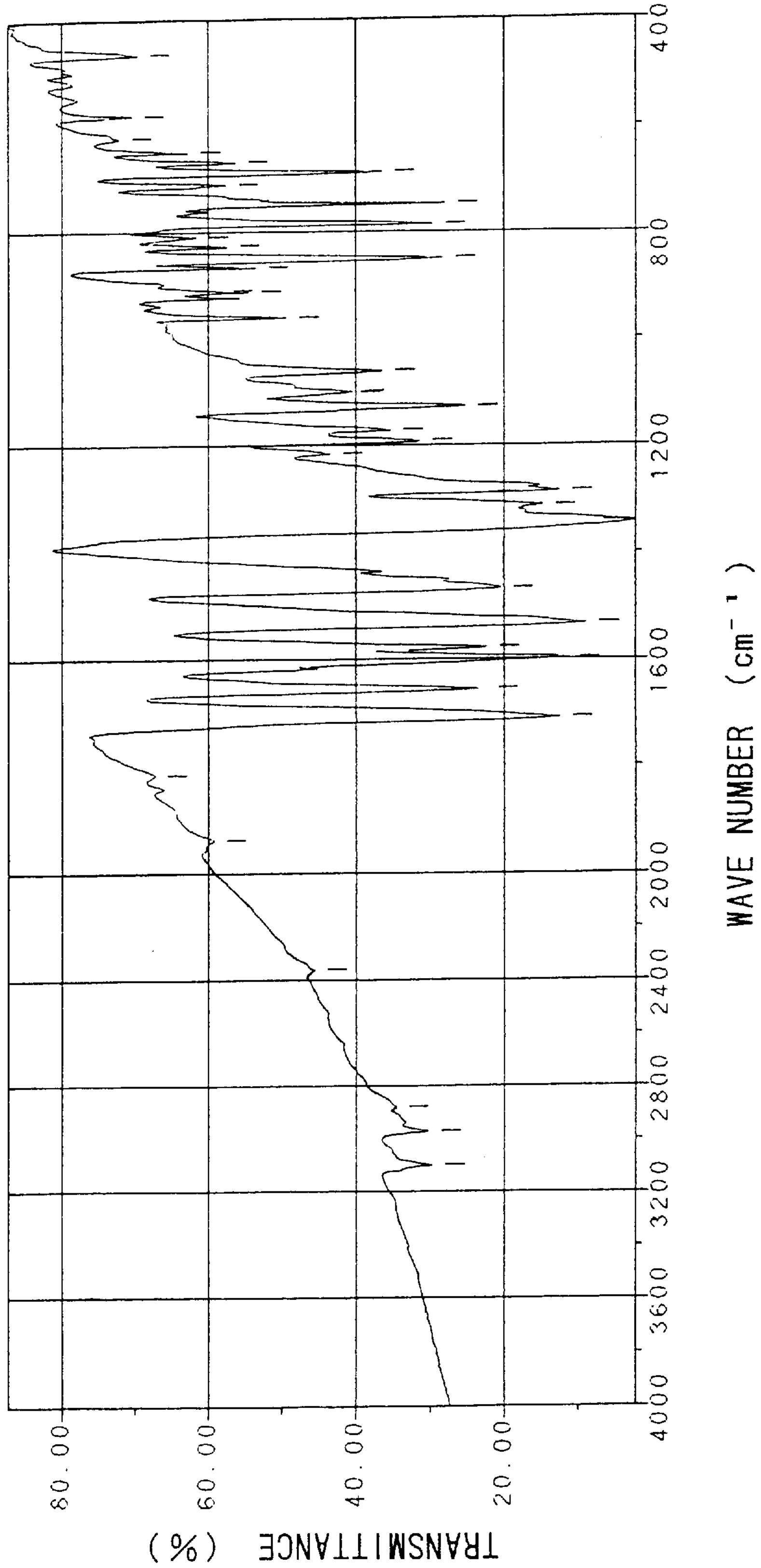

The infrared absorption spectrum of the compound (1-5) is shown in FIG. 6.

Synthesis Example 6

Synthesis of N-(2,6-diethylphenyl)-2,6-dinitrotryptoanthrinimine (1-6)

According to the same manner as that described in Synthesis Example 1 except for using 2,6-diethylaniline (3.6 g, 20 mmol) in place of o-isopropylaniline (2.7 g, 20 mmol), 4.6 g of the titled compound was obtained. Yield: 66%, Melting point: 227° C.

Figure 7:
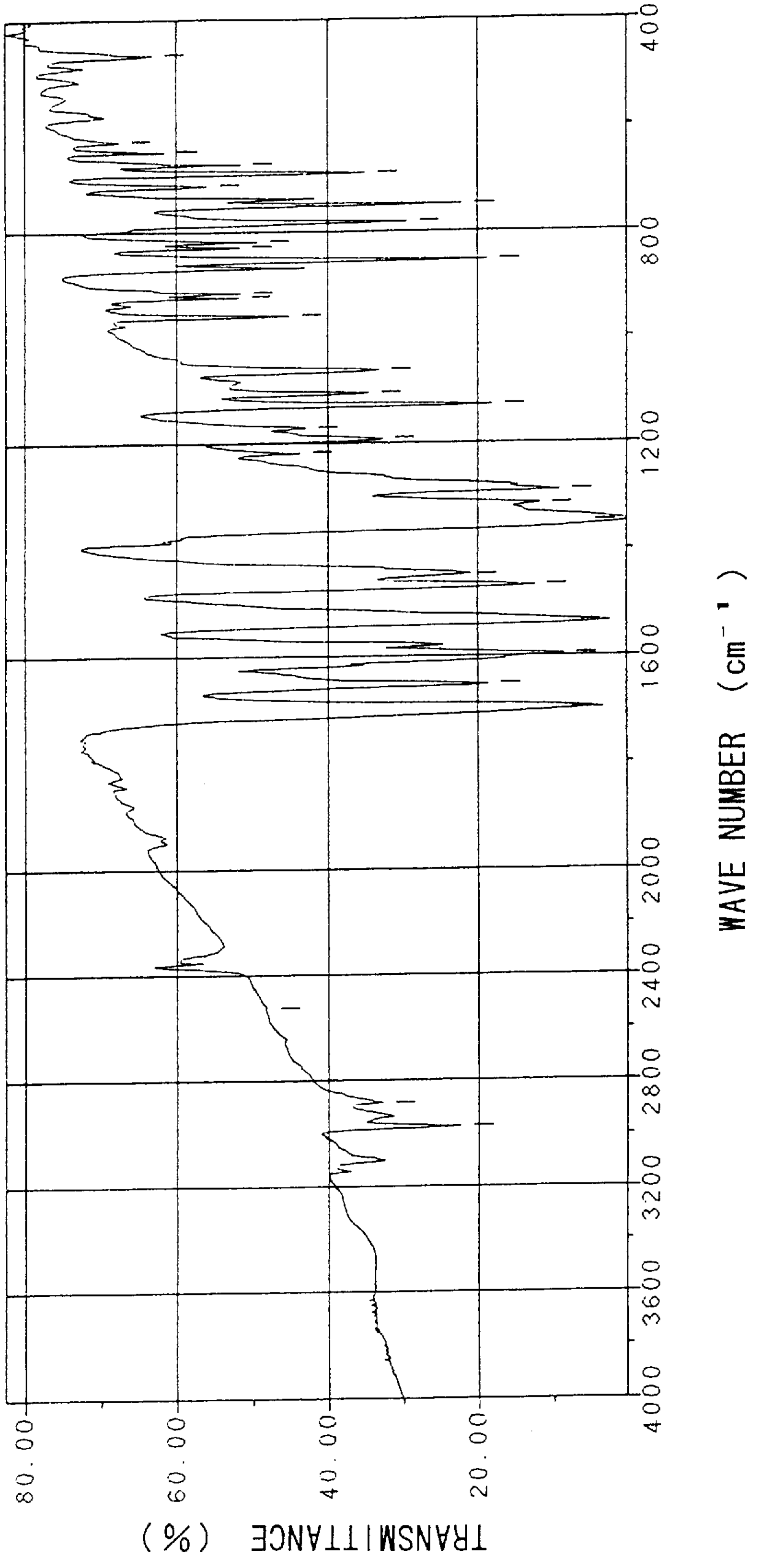

The infrared absorption spectrum of the compound (1-6) is shown in FIG. 7.

Synthesis Example 7

Synthesis of N-(2,5-di-t-butylphenyl)-2,6-dinitrotryptoanthrinimine (1-7)

According to the same manner as that described in Synthesis Example 1 except for using 2,5-di-t-butylaniline (3.6 g, 20 mmol) in place of o-isopropylaniline (2.7 g, 20 mmol), 5.3 g of the titled compound was obtained. Yield: 71%, Melting point: 250° C.

Figure 8:
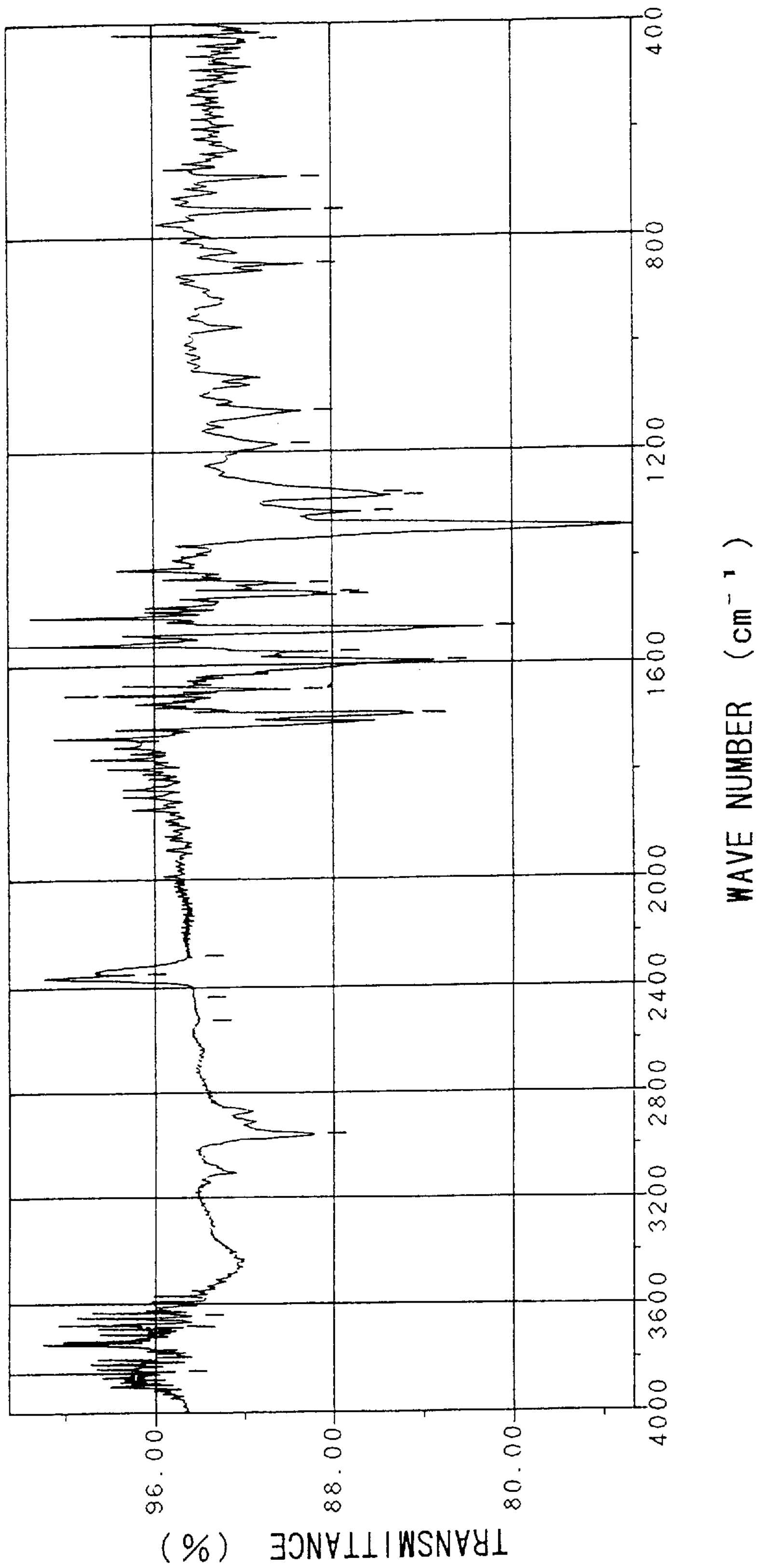

The infrared absorption spectrum of the compound (1-7) is shown in FIG. 8.

Synthesis Example 8

Synthesis of N-(o-benzylphenyl)-2,6-dinitrotryptoanthrinimine (1-8)

According to the same manner as that described in Synthesis Example 1 except for using 2-benzylaniline (3.7 g, 20 mmol) in place of o-isopropylaniline (2.7 g, 20 mmol), 4.4 g of the titled compound was obtained. Yield: 58%, Melting point: 250° C.

Figure 9:
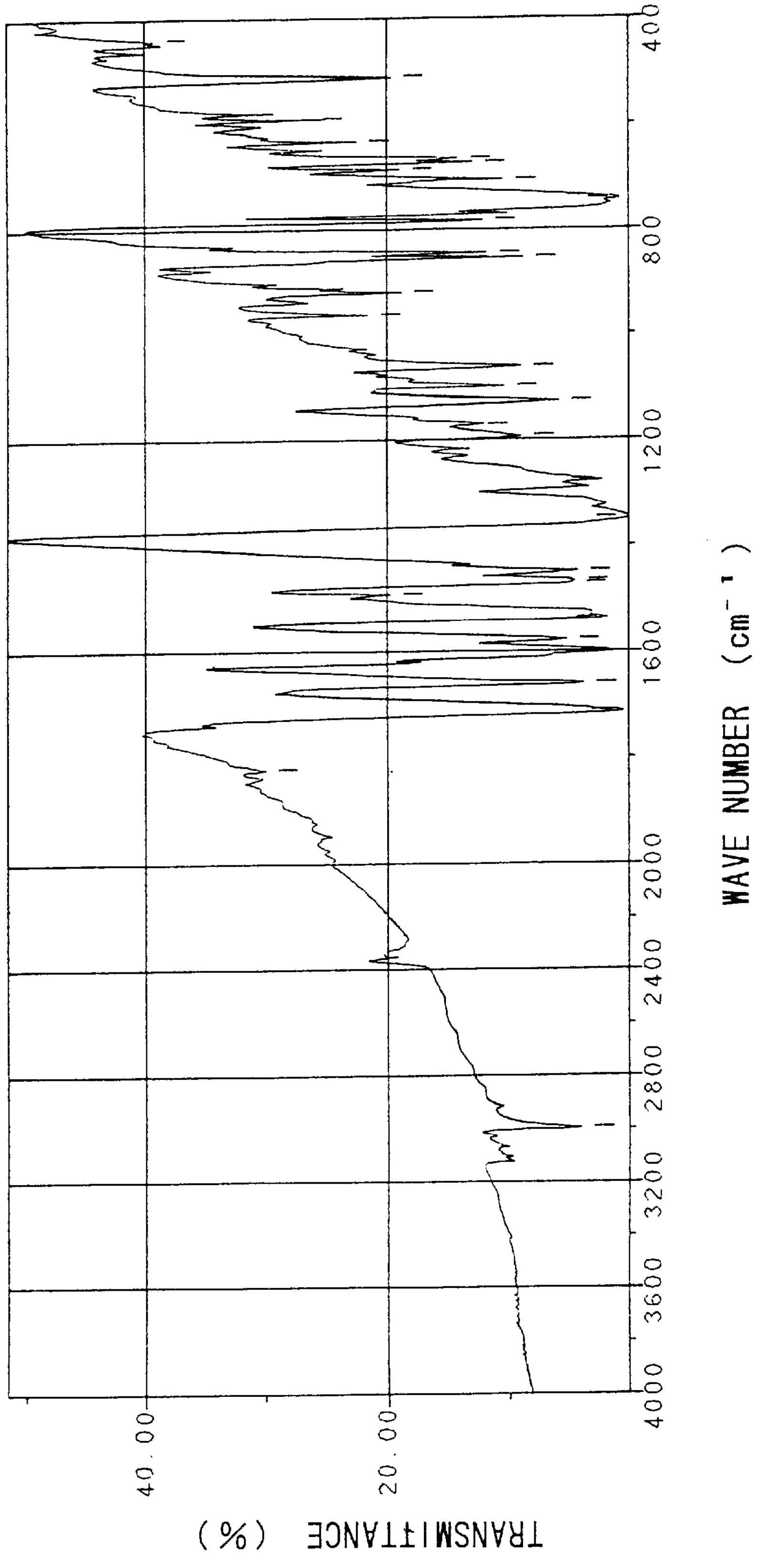

The infrared absorption spectrum of the compound (1-8) is shown in FIG. 9.

Synthesis Example 9

Synthesis of N-(2,4-dimethylphenyl)-2,6-dinitrotryptoanthrinimine (1-9)

According to the same manner as that described in Synthesis Example 1 except for using 2,4-xylidine (2.4 g, 20 mmol) in place of o-isopropylaniline (2.7 g, 20 mmol), 5.3 g of the titled compound was obtained. Yield: 81%, Melting point: 263° C.

Figure 10:
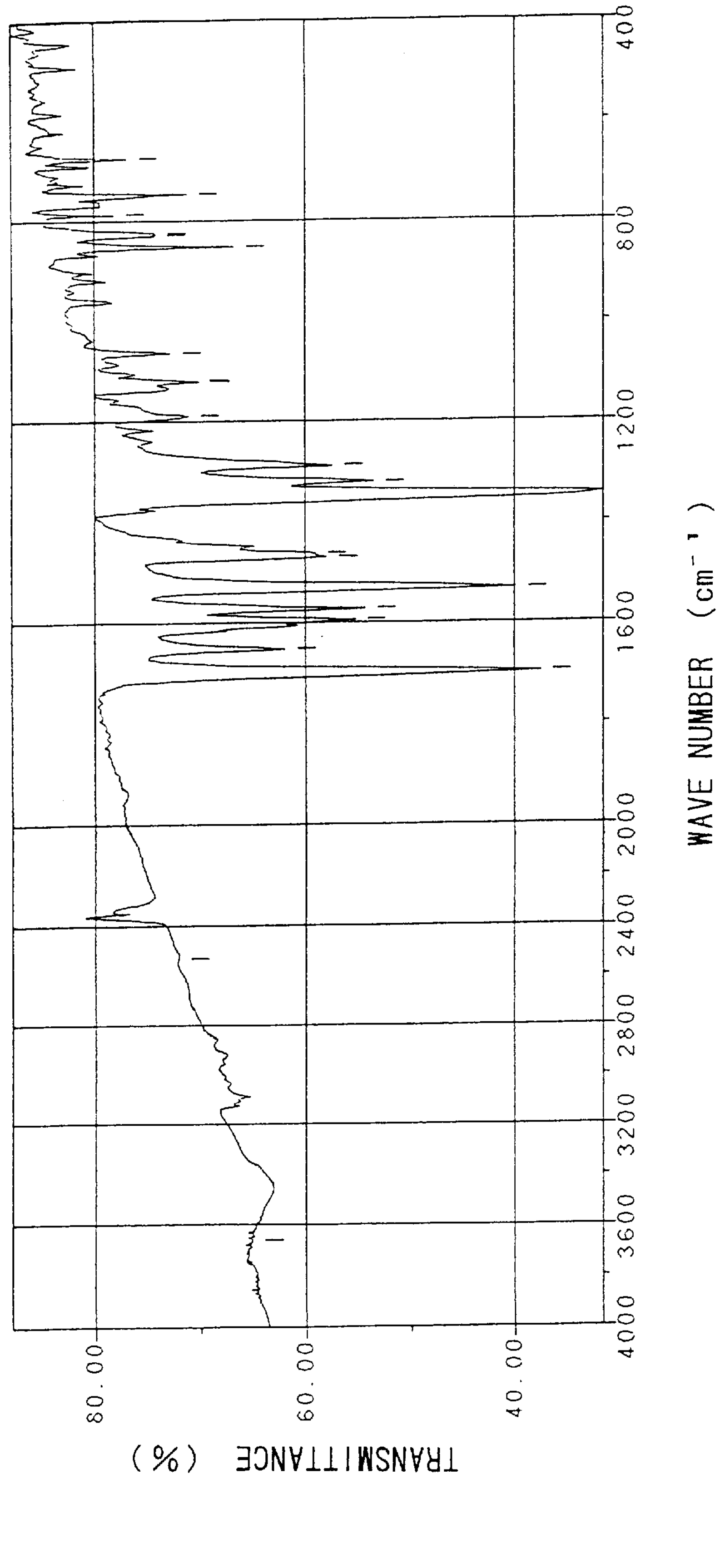

The infrared absorption spectrum of the compound (1-9) is shown in FIG. 10.

Synthesis Example 10

Synthesis of N-(2,4,6-trimethylphenyl)-2,6-dinitrotryptoanthrinimine (1-10)

According to the same manner as that described in Synthesis Example 1 except for using 2,4,6-trimethylaniline (2.7 g, 20 mmol) in place of o-isopropylaniline (2.7 g, 20 mmol), 5.3 g of the titled compound was obtained. Yield: 78%, Melting point: 280° C. or more (decomposition)

Figure 11:
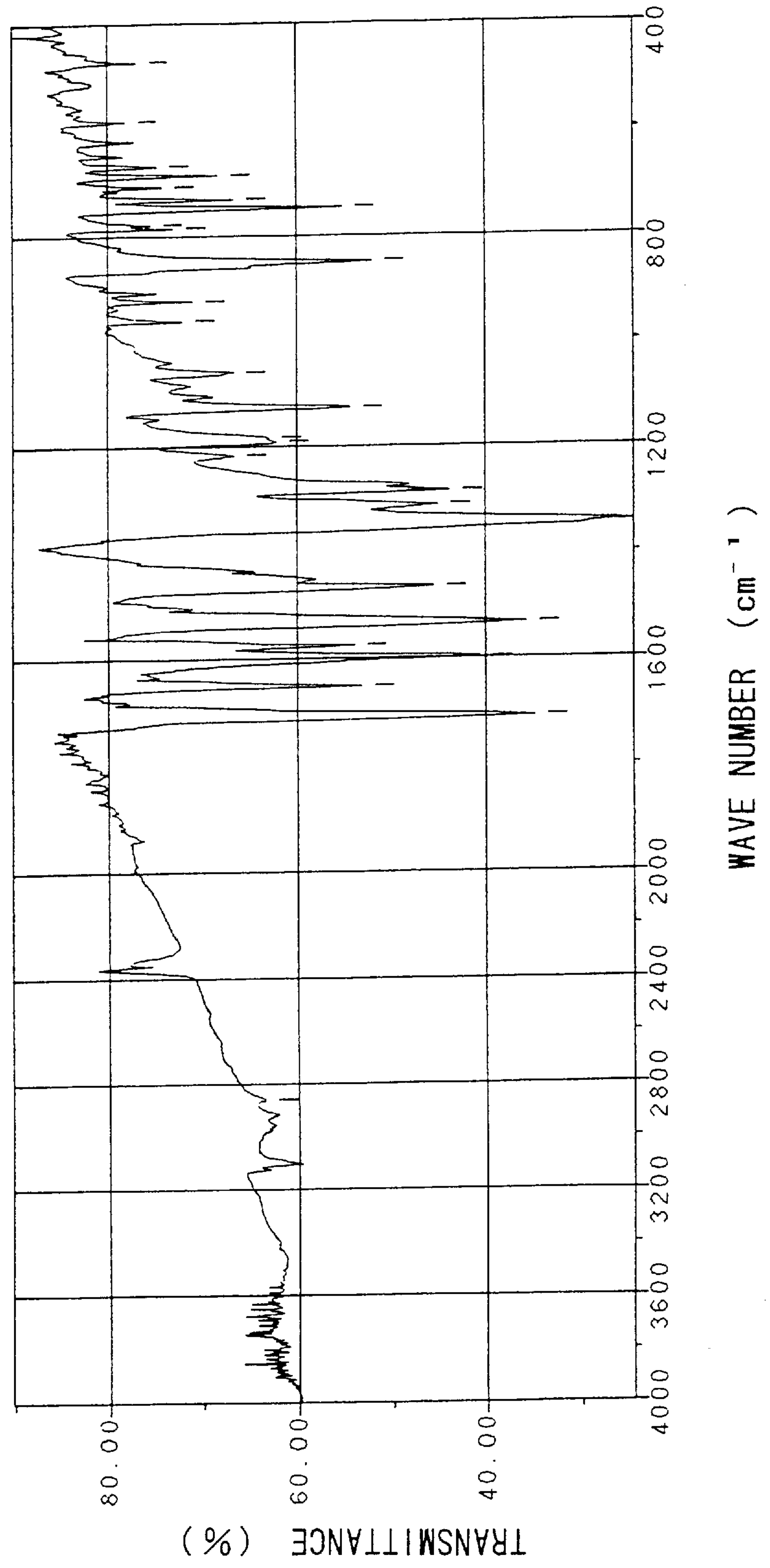

The infrared absorption spectrum of the compound (1-10) is shown in FIG. 11.

Synthesis Example 11

Synthesis of N-(4-fluoro-2-methylphenyl)-2,6-dinitrotryptoanthrinimine (1-11)

According to the same manner as that described in Synthesis Example 1 except for using 2-methylaniline (2.5 g, 20 mmol) in place of o-isopropylaniline (2.7 g, 20 mmol), 3.5 g of the titled compound was obtained. Yield: 53%, Melting point: 268° C.

Production of electrophotosensitive material

Examples 1 to 33 and Comparative Examples 1 to 5

An electric charge generating material, a hole transferring material, an electron transferring material, a binding resin and a solvent were formulated in the proportion (parts by weight) shown below, and then mixed and dispersed in a ball mill for 50 hours to prepare a coating solution for single-layer type photosensitive layer.

| (Components) | (Parts by weight) |
|---|---|
| Electric charge generating material | 5 |
| Hole transferring material | 50 |
| Electron transferring material | 30 |
| Binding resin | 100 |
| Solvent | 800 |

Then, the above coating solution was applied on an aluminum tube, followed by hot-air drying at 100° C. for 60 minutes to obtain a single-layer type electrophotosensitive material of 15 to 20 $\mu$m in film thickness, respectively.

As the above hole transferring material, N,N,N',N'-tetrakis(p-methylphenyl)-3,3'-dimethylbenzidine (ionization potential (Ip)=5.56 eV) was used. As the binding resin, polycarbonate was used. As the solvent, tetrahydrofuran was used.

As the electric charge generating material (CGM), any one of the following compounds was used.

$PcH_2$: X-type metal-free phthalocyanine (Ip=5.38 eV)

PcTiO: oxotitanyl phthalocyanine (Ip=5.32 eV)

Perylene: perylene pigment of the above formula (31) wherein $R^{130}$ to $R^{133}$ indicate a methyl group (Ip=5.50 eV)

As the electron transferring material (ETM), any one of tryptoanthrinimine derivatives represented by the above formulas (1-1) to (1-11) and a diphenoquinone derivative represented by the following formula (Q) was used.

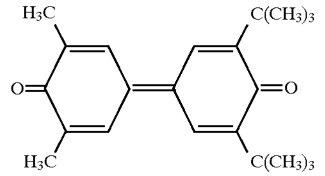

(Q)

The following tests were conducted using the resulting photosensitive materials.

Evaluation of electrophotosensitivity material

By using a drum sensitivity tester manufactured by GEN-TEC Co., a voltage was applied on the surface of the photosensitive material of the above respective Examples and Comparative Examples to charge the surface at +700 V. Then, this photosensitive material was exposed by irradiating light to measure a potential $V_L$ (V) of the surface of the photosensitive material at the time at which 330 msec. has passed since the beginning of exposure.

Further, the condition of light irradiation varies depending on the kind of the electric charge generating material (i.e. phthalocyanine pigment, perylene pigment, etc.)

(1) In case of phthalocyanine pigment

Monochromic light having a wavelength of 780 nm (half-width: 20 nm) and a light intensity of 16 $\mu W/cm^2$ from a halogen lamp through a band-pass filter was irradiated on the surface of the photosensitive material charged at +700 V for 80 msec.

(2) In case of perylene pigment

White light (light intensity: 147 $\mu W/cm^2$) of a halogen lamp was irradiated on the surface of the photosensitive material charged at +700 V for 50 msec.

The results are shown in Tables 1 to 3. In the following tables, the electric charge generating materials and electron transferring materials used in the above respective Examples and Comparative Examples are shown by the above symbols or numbers of chemical formulas.

TABLE 1

| EXAMPLE NO. | CGM | ETM | VL (V) |
|---|---|---|---|
| 1 | $PcH_2$ | 1-1 | +179 |
| 2 | $PcH_2$ | 1-2 | +189 |
| 3 | $PcH_2$ | 1-3 | +183 |
| 4 | $PcH_2$ | 1-4 | +175 |
| 5 | $PcH_2$ | 1-5 | +177 |
| 6 | $PcH_2$ | 1-6 | +177 |
| 7 | $PcH_2$ | 1-7 | +180 |
| 8 | $PcH_2$ | 1-8 | +197 |
| 9 | $PcH_2$ | 1-9 | +185 |
| 10 | $PcH_2$ | 1-10 | +179 |
| 11 | $PcH_2$ | 1-11 | +194 |
| COMP. EX. | | | |
| 1 | $PcH_2$ | Q | +220 |
| 2 | $PcH_2$ | — | +478 |

TABLE 2

| EXAMPLE NO. | CGM | ETM | VL (V) |
|---|---|---|---|
| 12 | PcTiO | 1-1 | +184 |
| 13 | PcTiO | 1-2 | +197 |
| 14 | PcTiO | 1-3 | +189 |
| 15 | PcTiO | 1-4 | +180 |
| 16 | PcTiO | 1-5 | +184 |
| 17 | PcTiO | 1-6 | +182 |
| 18 | PcTiO | 1-7 | +189 |
| 19 | PcTiO | 1-8 | +204 |
| 20 | PcTiO | 1-9 | +194 |
| 21 | PcTiO | 1-10 | +189 |
| 22 | PcTiO | 1-11 | +200 |
| COMP. EX. 3 | PcTiO | Q | +242 |

TABLE 3

| EXAMPLE NO. | CGM | ETM | VL (V) |
|---|---|---|---|
| 23 | PERYLENE | 1-1 | +210 |
| 24 | PERYLENE | 1-2 | +227 |
| 25 | PERYLENE | 1-3 | +216 |
| 26 | PERYLENE | 1-4 | +208 |
| 27 | PERYLENE | 1-5 | +209 |
| 28 | PERYLENE | 1-6 | +219 |
| 29 | PERYLENE | 1-7 | +220 |
| 30 | PERYLENE | 1-8 | +224 |
| 31 | PERYLENE | 1-9 | +222 |
| 32 | PERYLENE | 1-10 | +214 |
| 33 | PERYLENE | 1-11 | +221 |
| COMP. EX. 4 | PERYLENE | Q | +294 |
| COMP. EX. 5 | PERYLENE | — | +521 |

Examples 34 to 55 and Comparative Examples 6 to 7

100 Parts by weight of an electric charge generating material, 100 parts by weight of a binding resin (polyvinyl butyral) and 2,000 parts by weight of a solvent (tetrahydrofuran) were mixed and dispersed in a ball mill for 50 hours to prepare a coating solution for electric charge generating layer. Then, this coating solution was applied on an aluminum tube, followed by hot-air drying at 100° C. for 60 minutes to form an electric charge generating layer of 1 $\mu m$ in film thickness.

On the other hand, 100 parts by weight of an electron transferring material, 100 parts by weight of a binding resin (polycarbonate) and 800 parts by weight of a solvent (toluene) were mixed and dispersed in a ball mill for 50 hours to prepare a coating solution for electric charge transferring layer. Then, this coating solution was applied on the above electric charge generating layer, followed by hot-air drying at 100° C. for 60 minutes to form an electric charge transferring layer of 20 $\mu m$ in film thickness, thereby producing a positive charging type multi-layer type photosensitive material, respectively.

As the electric charge generating material, any one of the above X-type metal-free phthalocyanine pigment and perylene pigment was used.

As the electron transferring material, the tryptoanthrinimine derivatives represented by the above formulas (1-1) to (1-11) of the present invention and diphenoquinone derivative represented by the above formula (Q) were used.

The resulting photosensitive materials were tested according to the same manner as that described in Examples 1 to 33. The results are shown in Tables 4 to 5.

TABLE 4

| EXAMPLE NO. | CGM | ETM | VL (V) |
|---|---|---|---|
| 34 | $PcH_2$ | 1-1 | +268 |
| 35 | $PcH_2$ | 1-2 | +284 |
| 36 | $PcH_2$ | 1-3 | +275 |
| 37 | $PcH_2$ | 1-4 | +263 |
| 38 | $PcH_2$ | 1-5 | +266 |
| 39 | $PcH_2$ | 1-6 | +269 |
| 40 | $PcH_2$ | 1-7 | +272 |
| 41 | $PcH_2$ | 1-8 | +289 |
| 42 | $PcH_2$ | 1-9 | +280 |
| 43 | $PcH_2$ | 1-10 | +270 |
| 44 | $PcH_2$ | 1-11 | +290 |
| COMP. EX. 6 | $PcH_2$ | Q | +346 |

TABLE 5

| EXAMPLE NO. | CGM | ETM | VL (V) |
|---|---|---|---|
| 45 | PERYLENE | 1-1 | +302 |
| 46 | PERYLENE | 1-2 | +321 |
| 47 | PERYLENE | 1-3 | +299 |
| 48 | PERYLENE | 1-4 | +295 |
| 49 | PERYLENE | 1-5 | +297 |
| 50 | PERYLENE | 1-6 | +311 |
| 51 | PERYLENE | 1-7 | +316 |
| 52 | PERYLENE | 1-8 | +323 |
| 53 | PERYLENE | 1-9 | +319 |
| 54 | PERYLENE | 1-10 | +309 |
| 55 | PERYLENE | 1-11 | +318 |
| COMP. EX. 7 | PERYLENE | Q | +386 |

As is apparent from Tables 1 to 5, regarding all of the electrophotosensitive materials using the tryptoanthrinimine derivative of the present invention as the electron transferring material of the Examples, the potential after exposure $V_L$ is reduced in comparison with the photosensitive materials of the Comparative Examples wherein the construction of the photosensitive material excepting for the electron transferring material is the same as that of the Examples and a diphenoquinone derivative is used as the electron transferring material or no electron transferring material is used.

That is, the photosensitive materials using the compound of the present invention as the electron transferring material are improved in sensitivity in comparison with the photosensitive materials wherein that compound is not used, whether it is the single-layer type or multi-layer type.

Examples 56 to 67

According to the same manner as that described in Examples 1 to 33 except for using the following electric charge generating material, hole transferring material and electron transferring material, a single-layer type electrophotosensitive material was produced.

Electric charge generating material (CGM): $PcH_2$ described above

Hole transferring material (HTM): any one of phenylenediamine derivatives represented by the formulas (2-1) to (2-6)

Electron transferring material (ETM): any one of tryptoanthrinimine derivatives represented by the formulas (1-4) and (1-7)

The ionization potential of the hole transferring materials represented by the above formulas (2-1) to (2-6) is as follows, respectively.

(2-1)=5.62 eV, (2-2)=5.62 eV (2-3)=5.49 eV, (2-4)=5.60 eV (2-5)=5.58 eV, (2-6)=5.64 eV

The ionization potential (Ip) of the electric charge generating material and hole transferring material was measured by a photoelectric analytical apparatus under atmospheric condition (Model AC-1, manufactured by Riken Instrument Co., Ltd.).

The resulting photosensitive materials were subjected to the photosensitivity test and evaluation of the wear resistance. The photosensitivity test was conducted according to the same manner as that of the item (1) (in case of phthalocyanine pigment) among the evaluation in Examples 1 to 33.

Evaluation of wear resistance

A photosensitive material obtained in the above respective Examples and comparative Examples was fit with a photosensitive material drum of a facsimile (Model LDC-650, manufactured by Mita Industrial Co., Ltd.) and, after rotating 150,000 times without passing a paper through it, a change in thickness of the photosensitive layer was determined, respectively. The smaller the change in thickness, the better the wear resistance is.

The results are shown in Table 6. Further, the test results of Comparative Example 1 are also shown in Table 6, for comparison.

TABLE 6

| EXAMPLE NO. | CGM | HTM | ETM | $V_L$ (V) | AMOUNT OF WEAR ($\mu$m) |
|---|---|---|---|---|---|
| 56 | $PcH_2$ | 2-1 | 1-4 | 171 | 3.1 |
| 57 | $PcH_2$ | 2-2 | 1-4 | 173 | 2.8 |
| 58 | $PcH_2$ | 2-3 | 1-4 | 177 | 3.3 |
| 59 | $PcH_2$ | 2-4 | 1-4 | 173 | 3.2 |
| 60 | $PcH_2$ | 2-5 | 1-4 | 179 | 3.3 |
| 61 | $PcH_2$ | 2-6 | 1-4 | 172 | 3.0 |
| 62 | $PcH_2$ | 2-1 | 1-7 | 171 | 2.9 |
| 63 | $PcH_2$ | 2-2 | 1-7 | 175 | 2.9 |
| 64 | $PcH_2$ | 2-3 | 1-7 | 176 | 3.0 |
| 65 | $PcH_2$ | 2-4 | 1-7 | 180 | 3.1 |
| 66 | $PcH_2$ | 2-5 | 1-7 | 177 | 2.8 |
| 67 | $PcH_2$ | 2-6 | 1-7 | 171 | 3.0 |
| COMP. EX. 1 | $PcH_2$ | 6Me-4PhB | Q | 220 | 4.9 |

Examples 68 and 69

According to the same manner as that described in Examples 56 to 67 except for using oxotitanyl phthalocyanine (PcTiO, Ip=5.32 eV) as the electric charge generating material, the phenylenediamine derivative represented by the formula (2-1) as the hole transferring material and the tryptoanthrinimine derivative represented by the formula (1-4) or (1-7) as the electron transferring material, a single-layer type electrophotosensitive material was produced, respectively.

The resulting photosensitive materials were evaluated according to the same manner as that described in Examples 56 to 67. The results are shown in Table 7. Further, the test results of Comparative Example 3 are also shown in Table 7, for comparison.

TABLE 7

| EXAMPLE NO. | CGM | HTM | ETM | $V_L$ (V) | AMOUNT OF WEAR ($\mu$m) |
|---|---|---|---|---|---|
| 68 | PcTiO | 2-1 | 1-4 | 172 | 3.2 |
| 69 | PcTiO | 2-1 | 1-7 | 177 | 3.1 |
| COMP. EX. 3 | PcTiO | 6Me—4PhB | Q | 242 | 5.5 |

Examples 70 to 75

5 Parts by weight of an electric charge generating material, 50 parts by weight of a hole transferring material, 30 parts by weight of an electron transferring material, 10 parts by weight of an electron acceptive compound (EAC), 100 parts by weight of a binding resin (bisphenol A type polycarbonate) and 800 parts by weight of a solvent (tetrahydrofuran) were mixed and dispersed in a ball mill for 50 hours to prepare a coating solution for single-layer type photosensitive layer.

As the above electric charge generating material, X-type metal-free phthalocyanine ($PcH_2$) was used. As the hole transferring material, the phenylenediamine derivative represented by the formula (2-2) or (2-6) was used. As the electron transferring material, the tryptonathrinimine derivative represented by the formula (1-4) was used. In addition, as the electron acceptive compound, any one of 3,3',5,5'-tetra-t-butyl-diphenoquinone (Bu-DPQ, redox potential: −0.94 V), 3,5-dimethyl-3',5'-di-t-butyl-4,4'-diphenoquinone represented by the formula (Q) (redox potential: −0.86 eV) and 2,6-di-t-butyl-p-benzoquinone (Bu-BQ, redox potential: −1.30 V) was used.

The resulting photosensitive materials were evaluated according to the same manner as that described in Examples 56 to 67. The results are shown in Table 8.

TABLE 8

| EXAMPLE NO. | CGM | HTM | ETM | EAC | $V_L$ (V) | AMOUNT OF WEAR ($\mu$m) |
|---|---|---|---|---|---|---|
| 70 | $PcH_2$ | 2-2 | 1-4 | Bu-DPQ | 138 | 3.0 |
| 71 | $PcH_2$ | 2-2 | 1-4 | Q | 147 | 3.2 |
| 72 | $PcH_2$ | 2-2 | 1-4 | Bu-BQ | 156 | 3.2 |
| 73 | $PcH_2$ | 2-6 | 1-4 | Bu-DPQ | 136 | 3.1 |
| 74 | $PcH_2$ | 2-6 | 1-4 | Q | 146 | 3.3 |
| 75 | $PcH_2$ | 2-6 | 1-4 | Bu-BQ | 155 | 2.9 |

As is apparent from Tables 6 to 8, the photosensitive materials of Examples 56 to 75 have high sensitivity because the potential after exposure $V_L$ is reduced, and they are superior in wear resistance because of small wear amount.

Examples 76 to 81

According to the same manner as that described in Examples 1 to 33 except for using the following components as the electric charge generating material, hole transferring material and electron transferring material, a single-layer type electrophotosensitive material was produced, respectively.

Electric charge generating material: X-type metal-free phthalocyanine ($PcH_2$ Ip=5.38 eV) or oxotitanyl phthalocyanine (PcTiO, Ip=5.32 eV)

Hole transferring material: benzidine derivative represented by the formula (3-1) or (3-2)

Electron transferring material: nitrated tryptoanthrinimine derivative represented by the formula (1-4) or (1-7)

The melting point and ionization potential of the hole transferring materials represented by the formulas (3-1) and (3-2) are as follows, respectively.

(3-1): melting point=239.9° C., Ip=5.48 eV (3-2): melting point=217.8° C., Ip=5.51 eV Further, the ionization potential (Ip) of the electric charge generating material and hole transferring material was measured by a photoelectric analytical apparatus under atmospheric condition (Model AC-1, manufactured by Riken Instrument Co., Ltd.).

Regarding the resulting photosensitive materials, the photosensitivity was evaluated according to the same manner as that described in Examples 1 to 33. Furthermore, the glass transition temperature was measured and high-temperature storage characteristics were evaluated.

Measurement of glass transition temperature

About 5 mg of a photosensitive layer of the photosensitive materials obtained in the above respective Examples and Comparative Examples was peeled off and this film of the photosensitive layer was put in an aluminum pan, followed by sealing to obtain a sample. Then, this sample was measured under the following condition using a differential scanning calorimeter (Model DSC8230D, manufactured by Rigaku Denki Co., Ltd.). An extrapolated glass transition initiation temperature (Tig) was determined from the results according to JIS K 7121.

(Measuring conditions)

Environmental gas: air

Heating rate: 20° C./minutes

Evaluation of high-temperature storage characteristics

A photosensitive material obtained in the above respective Examples and Comparative Examples was fit with an imaging unit of a facsimile (Model LDC-650, manufactured by Mita Industrial Co., Ltd.) and, after standing at 50° C. for 10 days, an impression formed on the surface of the photosensitive layer was measured using a surface shape tester (Model SE-3H, manufactured by Kosaka Laboratory). The smaller the impression on the surface of the photosensitive layer, the better the high-temperature storage characteristics are.

The above imaging unit keeps a drum in contact with a cleaning blade under linear pressure of 1.5 g/mm. Accordingly, when using a photosensitive material drum having poor high-temperature storage characteristics (heat resistance), an impression is formed on the surface of the photosensitive layer after use. On the other hand, when the measured value of the impression is less than 0.3 $\mu$m, it can be said that no impression due to the above test was observed on the surface of the photosensitive layer, because the surface roughness of the photosensitive material is normally about 0.5 $\mu$m.

The test results are shown in Table 9. Further, the test results of Comparative Examples 1 and 3 are also shown in Table 9.

TABLE 9

| EXAMPLE NO. | CGM | HTM | ETM | $V_L$ (V) | $T_{ig}$ (°C.) | DENT ($\mu$m) |
|---|---|---|---|---|---|---|
| 76 | $PcH_2$ | 3-1 | 1-4 | 168 | 78.1 | <0.3 |
| 77 | $PcH_2$ | 3-2 | 1-4 | 172 | 79.3 | <0.3 |
| 78 | $PcH_2$ | 3-1 | 1-7 | 173 | 78.5 | <0.3 |
| 79 | $PcH_2$ | 3-2 | 1-7 | 171 | 78.4 | <0.3 |
| 80 | PcTiO | 3-1 | 1-4 | 174 | 79.2 | <0.3 |
| 81 | PcTiO | 3-2 | 1-4 | 173 | 78.5 | <0.3 |
| COMP. EX. 1 | $PcH_2$ | 6Me-4phB | Q | 220 | 69.0 | 1.2 |
| 3 | PcTiO | 6Me-4phB | Q | 242 | 69.1 | 1.2 |

Examples 82 to 93

According to the same manner as that described in Examples 76 to 81 except for using any one of benzidine derivatives represented by the formulas (4-1) to (4-5) as the hole transferring material, a single-layer type electrophotosensitive material was produced, respectively.

The melting point and ionization potential (Ip) of the hole transferring materials represented by the formulas (4-1) to (4-5) are as follows, respectively.

(4-1): Melting point=204.4° C., Ip=5.51 eV (4-2): Melting point=182.6° C., Ip=5.40 eV (4-3): Melting point=187.6° C., Ip=5.14 eV (4-4): Melting point=236.3° C., Ip=5.54 eV (4-5): Melting point=180.6° C., Ip=5.53 eV The above ionization potential (Ip) was measured according to the same manner as that described above.

The resulting photosensitive materials were tested according to the same manner as that described in Examples 76 to 81. The results are shown in Table 10.

TABLE 10

| EXAMPLE NO. | CGM | HTM | ETM | $V_L$ (V) | $T_{ig}$ (°C.) | DENT ($\mu$m) |
|---|---|---|---|---|---|---|
| 82 | $PcH_2$ | 4-1 | 1-4 | 169 | 77.5 | <0.3 |
| 83 | $PcH_2$ | 4-2 | 1-4 | 173 | 78.2 | <0.3 |
| 84 | $PcH_2$ | 4-3 | 1-4 | 172 | 78.5 | <0.3 |
| 85 | $PcH_2$ | 4-4 | 1-4 | 175 | 79.0 | <0.3 |
| 86 | $PcH_2$ | 4-5 | 1-4 | 170 | 78.7 | <0.3 |
| 87 | $PcH_2$ | 4-1 | 1-7 | 171 | 77.7 | <0.3 |
| 88 | $PcH_2$ | 4-2 | 1-7 | 170 | 79.1 | <0.3 |
| 89 | $PcH_2$ | 4-3 | 1-7 | 173 | 78.8 | <0.3 |
| 90 | $PcH_2$ | 4-4 | 1-7 | 167 | 77.9 | <0.3 |
| 91 | $PcH_2$ | 4-5 | 1-7 | 169 | 78.2 | <0.3 |
| 92 | PcTiO | 4-1 | 1-4 | 170 | 78.5 | <0.3 |
| 93 | PcTiO | 4-1 | 1-7 | 171 | 77.9 | <0.3 |

Examples 94 to 101

According to the same manner as that described in Examples 76 to 81 except for using any one of benzidine derivatives represented by the formulas (5-1) to (5-3) as the hole transferring material, a single-layer type electrophotosensitive material was produced, respectively.

The melting point and ionization potential (Ip) of the hole transferring materials of the formulas (5-1) to (5-3) are as follows, respectively.

(5-1): Melting point=183.0° C., Ip=5.54 eV (5-2): Melting point=270.4° C., Ip=5.55 eV (5-3): Melting point=181.6° C., Ip=5.68 eV The above ionization potential (Ip) was measured according to the same manner as that described above.

The resulting photosensitive materials were tested according to the same manner as that described in Examples 76 to 81. The results are shown in Table 11.

TABLE 11

| EXAMPLE NO. | CGM | HTM | ETM | $V_L$ (V) | $T_{ig}$ (°C.) | DENT (μm) |
|---|---|---|---|---|---|---|
| 94 | $PcH_2$ | 5-1 | 1-4 | 170 | 79.1 | <0.3 |
| 95 | $PcH_2$ | 5-2 | 1-4 | 172 | 78.2 | <0.3 |
| 96 | $PcH_2$ | 5-3 | 1-4 | 165 | 78.8 | <0.3 |
| 97 | $PcH_2$ | 5-1 | 1-7 | 168 | 77.9 | <0.3 |
| 98 | $PcH_2$ | 5-2 | 1-7 | 168 | 78.0 | <0.3 |
| 99 | $PcH_2$ | 5-3 | 1-7 | 170 | 78.1 | <0.3 |
| 100 | PcTiO | 5-1 | 1-4 | 173 | 77.9 | <0.3 |
| 101 | PcTiO | 5-1 | 1-7 | 173 | 79.0 | <0.3 |

Examples 102 to 107

5 Parts by weight of an electric charge generating material, 50 parts by weight of a hole transferring material, 30 parts by weight of an electron transferring material, 10 parts by weight of an electron acceptive compound, 100 parts by weight of a binding resin (bisphenol A type polycarbonate) and 800 parts by weight of a solvent (tetrahydrofuran) were mixed and dispersed in a ball mill for 50 hours to prepare a coating solution for photosensitive layer. Then, according to the same manner as that described in Examples 76 to 81, a single-layer type electrophotosensitive material was produced using the resulting coating solution, respectively.

As the above electric charge generating material, X-type metal-free phthalocyanine ($PcH_2$) was used. As the hole transferring material, the benzidine derivative represented by the formula (3-1) was used. As the electron transferring material, the tryptoanthrinimine derivative represented by the formula (1-4) or (1-7) was used. In addition, as the electron acceptive compound, 3,3',5,5'-tetra-t-butyl-4,4'-diphenoquinone (Bu-DPQ, redox potential=−0.94 V), 3,5-dimethyl-3',5'-di-t-butyl-4,4'-diphenoquinone (the above formula (Q), redox potential=−0.86 V) or 2,6-di-t-butyl-p-benzophenone (Bu-BQ, redox potential=−1.30 V) was used.

The resulting photosensitive materials were tested according to the same manner as that described in Examples 76 to 81. The results are shown in Table 12.

TABLE 12

| EXAMPLE NO. | CGM | HTM | ETM | EAC | $V_L$ (V) | $T_{ig}$ (°C.) | DENT (μm) |
|---|---|---|---|---|---|---|---|
| 102 | $PcH_2$ | 3-1 | 1-4 | Bu-DPQ | 134 | 76.5 | <0.3 |
| 103 | $PcH_2$ | 3-1 | 1-4 | Q | 143 | 77.1 | <0.3 |
| 104 | $PcH_2$ | 3-1 | 1-4 | Bu-BQ | 151 | 74.0 | <0.3 |
| 105 | $PcH_2$ | 3-1 | 1-7 | Bu-DPQ | 139 | 77.0 | <0.3 |
| 106 | $PcH_2$ | 3-1 | 1-7 | Q | 148 | 76.8 | <0.3 |
| 107 | $PcH_2$ | 3-1 | 1-7 | Bu-BQ | 156 | 73.9 | <0.3 |

Examples 108 to 113

According to the same manner as that described in Examples 102 to 107 except for using the benzidine derivative represented by the formula (4-1) or (4-3) as the hole transferring material and the tryptoanthrinimine derivative represented by the formula (1-4) as the electron transferring material, a single-layer type electrophotosensitive material was produced, respectively.

The resulting photosensitive material were tested according to the same manner as that described in Examples 76 to 81. The results are shown in Table 13.

TABLE 13

| EXAMPLE NO. | CGM | HTM | ETM | EAC | $V_L$ (V) | $T_{ig}$ (°C.) | DENT (μm) |
|---|---|---|---|---|---|---|---|
| 108 | $PcH_2$ | 4-1 | 1-4 | Bu-DPQ | 135 | 76.9 | <0.3 |
| 109 | $PcH_2$ | 4-1 | 1-4 | Q | 144 | 77.2 | <0.5 |
| 110 | $PcH_2$ | 4-1 | 1-4 | Bu-BQ | 152 | 76.2 | <0.3 |
| 111 | $PcH_2$ | 4-3 | 1-4 | Bu-DPQ | 138 | 78.1 | <0.3 |
| 112 | $PcH_2$ | 4-3 | 1-4 | Q | 146 | 77.8 | <0.3 |
| 113 | $PcH_2$ | 4-3 | 1-4 | Bu-BQ | 155 | 75.8 | <0.3 |

Examples 114 to 119

According to the same manner as that described in Examples 102 to 107 except for using the benzidine derivative represented by the formula (5-1) or (5-3) as the hole transferring material and the tryptoanthrinimine derivative represented by the formula (1-4) as the electron transferring material, a single-layer type electrophotosensitive material was produced, respectively.

The resulting photosensitive material were tested according to the same manner as that described in Examples 76 to 81. The results are shown in Table 14.

TABLE 14

| EXAMPLE NO. | CGM | HTM | ETM | EAC | $V_L$ (V) | $T_{ig}$ (°C.) | DENT (μm) |
|---|---|---|---|---|---|---|---|
| 114 | $PcH_2$ | 5-1 | 1-4 | Bu-DPQ | 136 | 78.8 | <0.3 |
| 115 | $PcH_2$ | 5-1 | 1-4 | Q | 145 | 78.5 | <0.3 |
| 116 | $PcH_2$ | 5-1 | 1-4 | Bu-BQ | 153 | 77.4 | <0.3 |
| 117 | $PcH_2$ | 5-3 | 1-4 | Bu-DPQ | 132 | 78.2 | <0.3 |
| 118 | $PcH_2$ | 5-3 | 1-4 | Q | 140 | 78.0 | <0.3 |
| 119 | $PcH_2$ | 5-3 | 1-4 | Bu-BQ | 149 | 77.0 | <0.3 |

As is apparent from Tables 9 to 14, the photosensitive materials of Examples 76 to 119 has high sensitivity because the potential after exposure $V_L$ is reduced, and they have high glass transition temperature (Tig) and excellent high-temperature storage characteristics.

Reference Example 2

Synthesis of 4-isopropyltryptoanthrine

8-Isopropylisatonic anhydride (10 g, 0.049 mol) and isatin (10 g, 0.068 mol) were added to 60 ml of pyridine, and the mixture was reacted under reflux for about 6 hours. After the completion of the reaction, the reaction solution was cooled to deposit a crystal. Then, the crystal was filtered, washed with methanol and dried to obtain 4.0 g of the titled compound. Yield: 28%

Reference Example 3

Synthesis of 2,6-diethyltryptoanthrine

Chloral hydrate (26 g), water (324 g) and anhydrous sodium sulfate (171 g) were charged in a 1 liter egg-plant type flask and stirred at 40° to 50° C. To the resulting solution, a mixed solution of an aqueous 10% hydrochloric acid and p-ethylaniline (14.7 g) was added and the mixture was refluxed for 30 minutes. After ice cooling, the deposited solid was filtered, washed with water, and then recrystallized from ethanol.

Then, 200 ml of concentrated sulfuric acid was charged in a 500 ml two necked flask, followed by ice cooling. Then, 5-ethylisatin (62.9 g) was added slowly, followed by stirring under ice cooling for 30 minutes. After stirring at 70° to 75° C. for 10 minutes, the reaction solution was cooled and added in ice water. The deposited solid was filtered, recrystallized from ethanol to obtain 17.8 g of 5-ethylisatin. Yield: 53.5%

5-Ethylisatin (70 g), acetic acid (200 ml) and concentrated sulfuric acid (0.8 ml) were charged in a 500 ml two-necked flask, followed by stirring at room temperature. Then, 50 ml of aqueous 30% hydrogen peroxide was added dropwise and, after stirring at 60° to 65° C. for additional one hour, the mixture was cooled. The deposited solid was filtered, washed with water and dried under vacuum to obtain 6-ethylisatoic anhydride. Crude yield: 35 g To a 200 ml flask, 5-ethylisatin (10 g), 6-ethylisatoic anhydride (10 g) and pyridine (10 ml) were added, and the mixture was heated at reflux for 2 hours. After the completion of the reflux, the reaction solution was cooled to deposit a solid. Then, the solid was filtered, dissolved in chloroform, washed with water and dried over anhydrous sodium sulfate. After the solvent was distilled off, 5.2 g of 2,6-diethyltryptoanthrine was obtained as a yellow solid.

Synthesis Example 12

Synthesis of N-(2-isopropyl-6-methylphenyl)-4-isopropyltryptoanthrinimine

4-Isopropytryptoanthrine (4.3 g, 0.015 mols) and 2-isopropyl-6-methylanilie (3 g, 0.020 mols) were dissolved in 50 ml of acetic acid, and the mixture was reacted under reflux for 2 hours. After the completion of the reaction, the reaction solution was added to 400 ml of water to deposit a crystal. Then, the crystal was filtered, washed with water, dried and purified by subjecting to silica gel column chromatography (developing solvent: mixed solvent of chloroform and hexane) to obtain 3.1 g of the titled compound (compound of the above formula (6-1), yield: 50%).

Melting point: 174° C.

Figure 12:
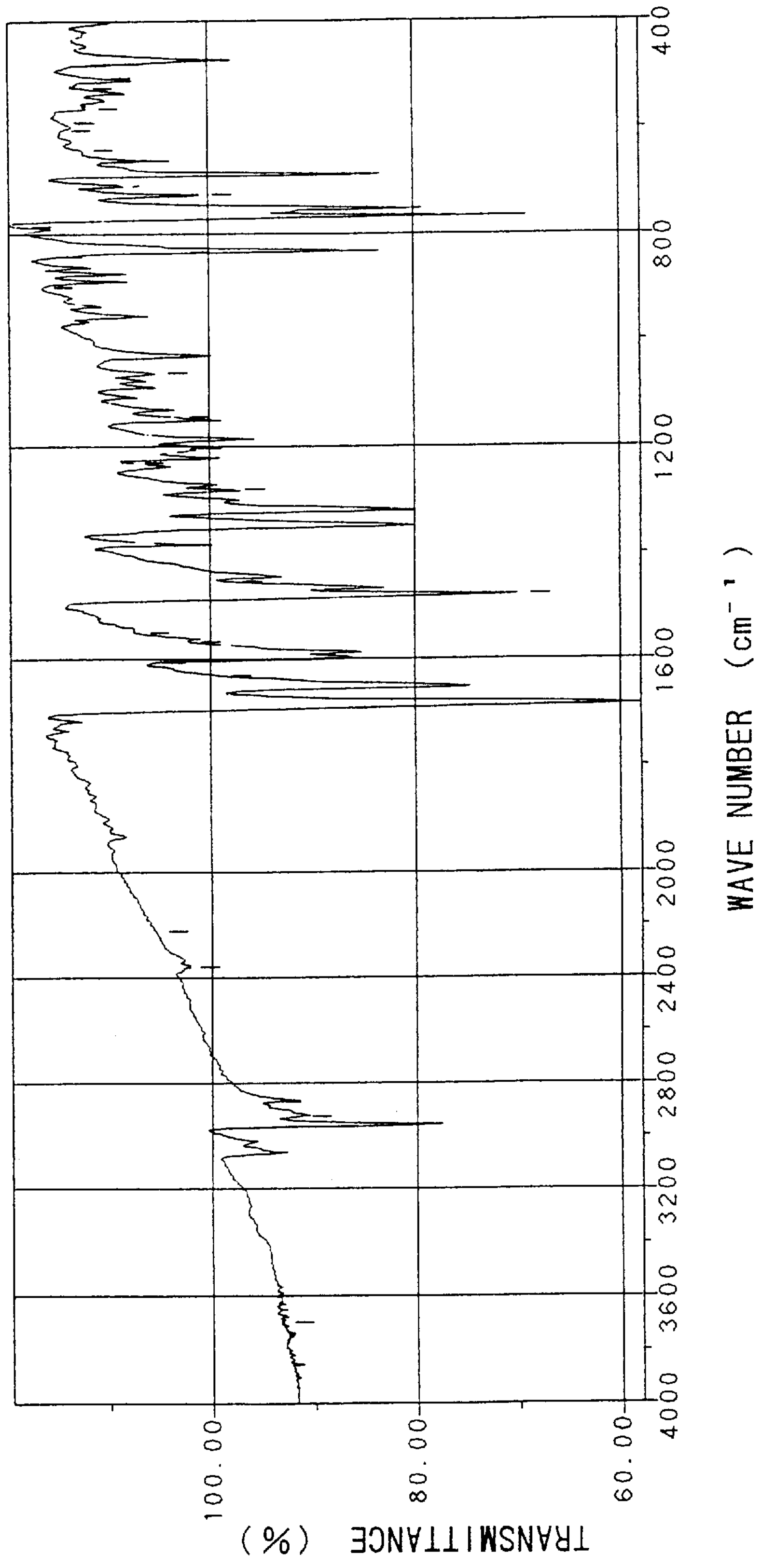

The infrared spectrum of the compound (6-1) is shown in FIG. 12.

Synthesis Example 13

Synthesis of N-(2-isopropylphenyl) tryptoanthrinimine

According to the same manner as that described in Synthesis Example 12 except for using tryptoanthrine and 2-isopropylaniline as the starting material of the reaction, the titled compound (compound of the above formula (6-2)) was obtained.

Melting point: 240° C.

Figure 13:
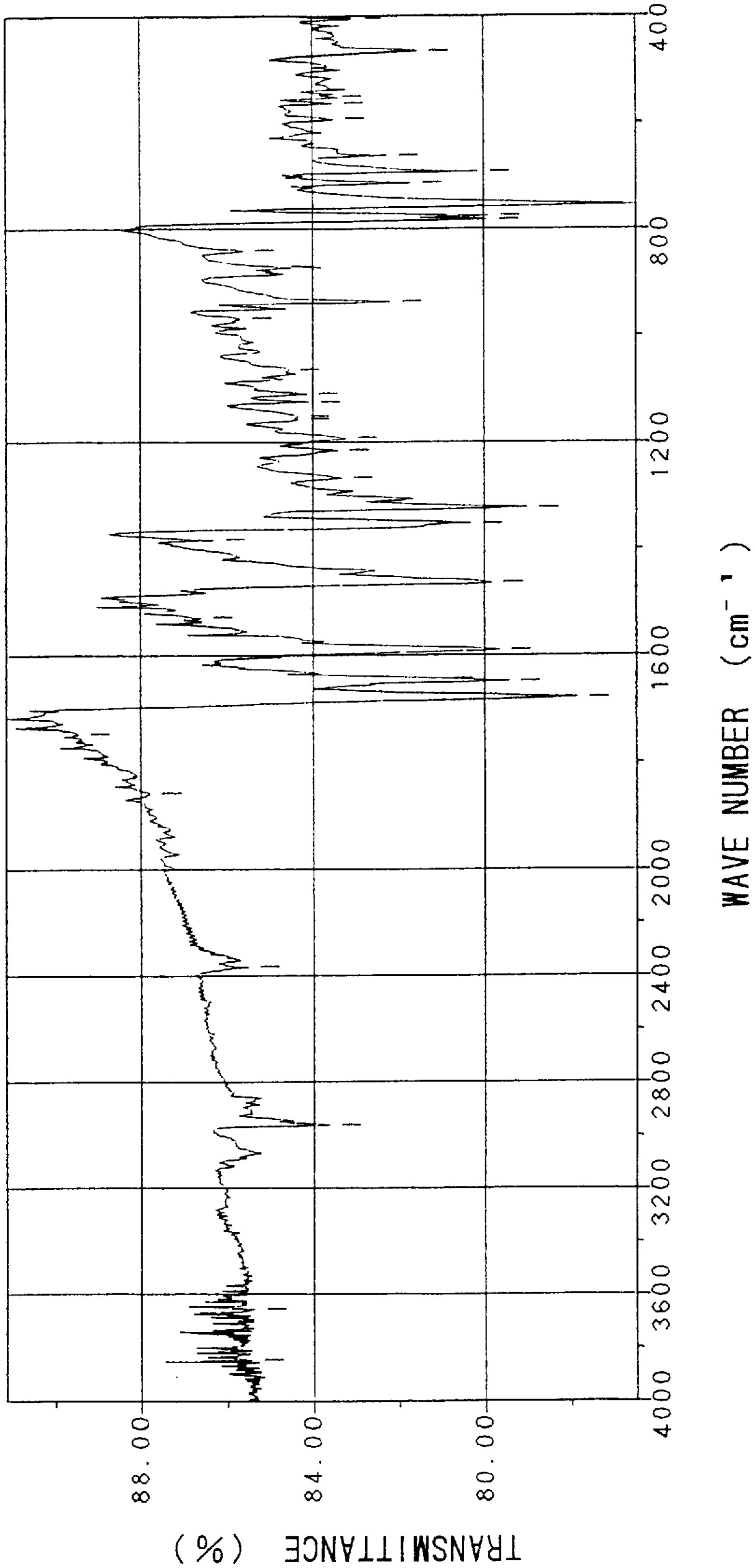

The infrared spectrum of the compound (6-2) is shown in FIG. 13.

Synthesis Example 14

Synthesis of N-(2,6-dimethylphenyl) tryptoanthrinimine

According to the same manner as that described in Synthesis Example 12 except for using tryptoanthrine and 2,6-dimethylaniline as the starting material of the reaction, the titled compound (compound of the above formula (6-3)) was obtained.

Melting point: 252° C.

Synthesis Example 15

Synthesis of N-(2-isopropyl-6-methylphenyl) tryptoanthrinimine

According to the same manner as that described in Synthesis Example 12 except for using tryptoanthrine and 2-isopropyl-6-methylaniline as the starting material of the reaction, the titled compound (compound of the above formula (6-4)) was obtained.

Melting point: 238° C.

Synthesis Example 16

Synthesis of N-(2-biphenylyl)-3,4-dimethyltryptoanthrinimine

According to the same manner as that described in Synthesis Example 12 except for using 3,4-dimethyltryptoanthrine and 2-biphenylaniline as the starting material of the reaction, the titled compound (compound of the above formula (6-5)) was obtained.

Synthesis Example 17

Synthesis of N-(2-isopropyl-6-methylphenyl)-2,6-diethyltryptoanthrinimine

To a 100 ml flask, 2,6-diethyltryptoanthrine (2.0 g) obtained in Reference Example 3, 2-isopropyl-6-methylaniline (1.0 g) and acetic acid (10 ml) were added, and the mixture was refluxed for 2 hours. After the completion of the reflux, the reaction solution was cooled and added to water. Then, the deposit was washed with water, dissolved in chloroform and washed again with water. The chloroform layer was dried over anhydrous sodium sulfate and, after the solvent was distilled off, it was purified by subjecting to silica gel column chromatography (developing solvent: mixed solvent of chloroform and hexane) to obtain 1.7 g of the titled compound (compound of the above formula (6-6)).

Synthesis Example 18

Synthesis of N-(4-fluoro-2-methylphenyl)-2,6-diethyltryptoanthrinimine

According to the same manner as that described in Synthesis Example 12 except for using 2,6-diethyltryptoanthrine obtained in Reference Example 3 and 4-fluoro-2-methylaniline as the starting material of the reaction, the titled compound (compound of the above formula (6-7)) was obtained.

Production of electrophotosensitive material

The respective components used in the following Examples and Comparative Examples are as follows.

(i) Electric charge generating material (CGM)

$PcH_2$: X-type metal-free phthalocyanine (ionization potential (Ip)=5.38 eV)

PcTiO: oxotitanyl phthalocyanine (Ip=5.32 eV)

Perylene: perylene pigment of the above general formula (31) wherein the substituents $R^{130}$ to $R^{133}$ indicate an methyl group (Ip=5.50 eV)

12-1: bisazo pigment represented by the above formula (12-1) (Ip=5.90 eV)

12-2: bisazo pigment represented by the above formula (12-2) (Ip=5.38 eV)

(ii) Hole transferring material (HTM)

16-1: benzidine derivative represented by the above formula (16-1) (Ip=5.56 eV)

16-2: benzidine derivative represented by the above formula (16-2) (Ip=5.44 eV)

16-3: benzidine derivative represented by the above formula (16-3) (Ip=5.43 eV)

17-1: phenylenediamine derivative represented by the above formula (17-1) (Ip=5.57 eV)

17-1: phenylenediamine derivative represented by the above formula (17-2) (Ip=5.64 eV)

18-1: naphthylenediamine derivative represented by the above formula (18-1) (Ip=5.59 eV)

18-2: naphthylenediamine derivative represented by the above formula (18-2) (Ip=5.64 eV)

18-3: naphthylenediamine derivative represented by the above formula (18-3) (Ip=5.61 eV)

(iii) Electron transferring material (ETM)

6-1: tryptoanthrinimine derivative represented by the above formula (6-1)

6-2: tryptoanthrinimine derivative represented by the above formula (6-2)

6-3: tryptoanthrinimine derivative represented by the above formula (6-3)

6-4: tryptoanthrinimine derivative represented by the above formula (6-4)

6-5: tryptoanthrinimine derivative represented by the above formula (6-5)

6-6: tryptoanthrinimine derivative represented by the above formula (6-6)

Q: 3,5-dimethyl-3',5'-di-t-butyl-4,4'-diphenoquinone (iv) Electron acceptive compound (EAC)

BQ: p-benzoquinone (redox potential=−0.81 V)

Bu-BQ: 2,6-di-t-butyl-p-benzoquinone (redox potential=−1.30 V)

Q: 3,5-dimethyl-3',5'-di-t-butyl-4,4'-diphenoquinone (redox potential=−0.86 eV)

Bu-DPQ: 3,3',5,5'-tetra-t-butyl-4,4'-diphenoquinone (redox potential=−0.94 V)

The above ionization potential was measured by a photoelectric analytical apparatus under atmospheric condition (Model AC-1, manufactured by Riken Instrument Co., Ltd.).

Examples 120 and 121 and Comparative Examples 8 and 9

An electric charge generating material (CGM), a hole transferring material (HTM), an electron transferring material (ETM) shown in Table 15, were blended together with a binding resin and a solvent in the proportion shown below, and then mixed and dispersed in a ball mill for 50 hours to prepare a coating solution for single-layer type photosensitive layer.

| (Components) | (Parts by weight) |
|---|---|
| Electric charge generating material | 5 |
| Hole transferring material | 50 |
| Electron transferring material | 30 |
| Binding resin (polycarbonate) | 100 |
| Solvent (tetrahydrofuran) | 800 |

Then, the above coating solution was applied on an aluminum tube, followed by hot-air drying at 100° C. for 60 minutes to obtain a single-layer type electrophotosensitive material for digital light source, which has a film thickness of 15 to 20 $\mu$m, respectively.

Examples 122 to 125

According to the same manner as that described in Examples 120 and 121 except that 5 parts by weight of an electric charge generating material, 50 parts by weight of a hole transferring material, 30 parts by weight of an electron transferring material, 100 parts by weight of a binding resin and 800 parts by weight of a solvent were added and 10 parts by weight of an electron acceptive compound (EAC) were further blended to prepare a coating solution for single-layer type photosensitive layer, a single-layer type electrophotosensitive material for digital light source was produced, respectively.

Example 126 and Comparative Example 10

According to the same manner as that described in Examples 120 and 121 and Comparative Examples 8 and 9 except for using a perylene pigment as the electric charge generating material, a single-layer type electrophotosensitive material for analog light source was produced, respectively.

Example 128 and Comparative Example 11

100 Parts by weight of an electric charge generating material ($PcH_2$), 100 parts by weight of a binding resin (polyvinyl butyral) and 2,000 parts by weight of a solvent (tetrahydrofuran) were mixed and dispersed in a ball mill for 50 hours to prepare a coating solution for electric charge generating layer. Then, this coating solution was applied on an aluminum tube as the conductive substrate by a dip coating method, followed by hot-air drying at 100° C. for 60 minutes to form an electric charge generating layer of 1 $\mu$m in film thickness.

Then, 100 parts by weight of an electron transferring material, 100 parts by weight of a binding resin (polycarbonate) and 800 parts by weight of a solvent (toluene) were mixed and dispersed in a ball mill for 50 hours to prepare a coating solution for electric charge transferring layer. Then, this coating solution was applied on the above electric charge generating layer by a dip coating method, followed by hot-air drying at 100° C. for 60 minutes to form an electric charge transferring layer of 20 $\mu$m in film thickness, thereby producing a multi-layer type electrophotosensitive material for digital light source, respectively.

Example 129 and Comparative Example 12

According to the same manner as that described in Example 128 and Comparative Example 11 except for using a perylene pigment as the electric charge generating material, a multi-layer type electrophotosensitive material for analog light source was produced, respectively.

The potential after exposure $V_L$ of the photosensitive materials obtained in Examples 120 to 129 and Comparative Examples 8 to 12 was measured according to the same manner as that described in Examples 1 to 33. The results are shown in Table 15.

TABLE 15

| EXAMPLE NO. | CGM | HTM | ETM | EAC | $V_L$ (V) |
|---|---|---|---|---|---|
| 120 | $PcH_2$ | 16-1 | 6-1 | — | 184 |
| COMP. EX. 8 | $PcH_2$ | 16-1 | Q | — | 220 |
| 121 | PcTiO | 16-1 | 6-1 | — | 193 |
| COMP. EX. 9 | PcTiO | 16-1 | Q | — | 242 |
| 122 | $PcH_2$ | 16-1 | 6-1 | BQ | 175 |
| 123 | $PcH_2$ | 16-1 | 6-1 | Bu—BQ | 167 |
| 124 | $PcH_2$ | 16-1 | 6-1 | Q | 160 |
| 125 | $PcH_2$ | 16-1 | 6-1 | Bu—DPQ | 153 |
| 126 | PERYLENE | 16-1 | 6-1 | — | 198 |
| COMP. EX. 10 | PERYLENE | 16-1 | Q | — | 294 |
| 128 | $PcH_2$ | — | 6-1 | — | 276 |
| COMP. EX. 11 | $PcH_2$ | — | Q | — | 346 |
| 129 | PERYLENE | — | 6-1 | — | 297 |
| COMP. EX. 12 | PERYLENE | — | Q | — | 386 |

Example 130 to 136

According to the same manner as that described in Example 120 to 129 except for using the compound represented by the above formula (6-2) as the electron transferring material, an electrophotosensitive material was produced, respectively.

The potential after exposure $V_L$ was measured according to the same manner as that described above, using the resulting photosensitive material. The results are shown in Table 16.

TABLE 16

| EXAMPLE NO | CGM | HTM | ETM | EAC | $V_L$ (V) |
|---|---|---|---|---|---|
| 130 | $PcH_2$ | 16-1 | 6-2 | — | 186 |
| 131 | PcTiO | 16-1 | 6-2 | — | 197 |
| 132 | $PcH_2$ | 16-1 | 6-2 | BQ | 177 |
| 133 | $PcH_2$ | 16-1 | 6-2 | Bu—DPQ | 160 |
| 134 | PERYLENE | 16-1 | 6-2 | — | 200 |
| 135 | $PcH_2$ | — | 6-2 | — | 279 |
| 136 | PERYLENE | — | 6-2 | — | 305 |

Example 137 to 143

According to the same manner as that described in Example 120 to 129 except for using the compound represented by the above formula (6-3) as the electron transferring material, an electrophotosensitive material was produced, respectively.

The potential after exposure $V_L$ was measured according to the same manner as that described above, using the resulting photosensitive material. The results are shown in Table 17.

TABLE 17

| EXAMPLE NO | CGM | HTM | ETM | EAC | $V_L$ (V) |
|---|---|---|---|---|---|
| 137 | $PcH_2$ | 16-1 | 6-3 | — | 182 |
| 138 | PcTiO | 16-1 | 6-3 | — | 189 |
| 139 | $PcH_2$ | 16-1 | 6-3 | Q | 150 |
| 140 | $PcH_2$ | 16-1 | 6-3 | Bu—DPQ | 142 |
| 141 | PERYLENE | 16-1 | 6-3 | — | 190 |
| 142 | $PcH_2$ | — | 6-3 | — | 281 |
| 143 | PERYLENE | — | 6-3 | — | 302 |

Examples 144 to 149 and Comparative Example 13

The compound represented by the above formula (12-1) was used as the electric charge generating material and, further, the hole transferring material and electron transferring material shown in Table 18 were blended together with the binding resin and solvent, and then mixed and dispersed in a ball mill for 50 hours to prepare a coating solution for single-layer type photosensitive layer.

| (Components) | (Parts by weight) |
|---|---|
| Electric charge generating material | 5 |
| Hole transferring material | 100 |
| Electron transferring material | 30 |
| Binding resin (polycarbonate) | 100 |
| Solvent (tetrahydrofuran) | 800 |

Then, the above coating solution was applied on an aluminum tube by dip coating method, followed by hot-air drying at 110° C. for 30 minutes to obtain a single-layer type photosensitive material having a single layer-type photosensitive layer of 25 μm in film thickness, respectively.

(Evaluation of characteristics of photosensitive material)

The electrophotosensitive materials obtained in the above Examples and Comparative Examples were subjected to the following electrical characteristics test, and their characteristics were evaluated.

Initial electrical characteristics test

By using the above drum sensitivity tester manufactured by GENTEC Co., a voltage was applied on the surface of an electrophotosensitive material to charge the surface at +700±20 V to measure the surface potential $V_O$ (V). Then, white light (light intensity: 10 lux) of a halogen lamp as an exposure light source was irradiated on the surface of the electrophotosensitive material for 1.5 seconds (irradiation time) and the time which is necessary for the above surface potential to be reduced to half was measured, thereby calculating a half-life exposure $E_{1/2}$ (lux·second).

The results are shown in Table 18.

TABLE 18

CGM: 12-1

| | | | INITIAL CHARACTERISTICS | | | AFTER REPEATING | |
|---|---|---|---|---|---|---|---|
| EXAMPLE NO. | HTM | ETM | $V_0$ | Vr | $E_{1/2}$ | $\Delta V_0$ | ΔVr |
| 144 | 16-1 | 6-2 | 702 | 86 | 1.31 | −26 | +15 |
| 145 | 16-1 | 6-3 | 705 | 84 | 1.30 | −23 | +13 |
| 146 | 16-1 | 6-4 | 701 | 85 | 1.30 | −24 | +14 |
| 147 | 16-1 | 6-1 | 708 | 89 | 1.33 | −25 | +15 |
| 148 | 16-1 | 6-1 | 693 | 92 | 1.35 | −25 | +13 |
| 149 | 16-1 | 6-1 | 702 | 83 | 1.29 | −22 | +10 |
| COMP. EX. 13 | 16-1 | Q | 700 | 102 | 1.62 | −42 | +22 |

Examples 150 to 157

According to the same manner as that described in Examples 144 to 149 except for using the hole transferring material and electron transferring material shown in Table 19, a single-layer type electrophotosensitive material was produced, respectively, and their electrical characteristics were evaluated. The results are shown in Table 19.

TABLE 19

CGM: 12-1

| | | | INITIAL CHARACTERISTICS | | | AFTER REPEATING | |
|---|---|---|---|---|---|---|---|
| EXAMPLE NO. | HTM | ETM | $V_0$ | Vr | $E_{1/2}$ | $\Delta V_0$ | ΔVr |
| 150 | 17-1 | 6-2 | 697 | 84 | 1.24 | −12 | +9 |
| 151 | 17-1 | 6-3 | 702 | 85 | 1.26 | −16 | +7 |
| 152 | 17-1 | 6-4 | 695 | 86 | 1.27 | −15 | +8 |
| 153 | 17-1 | 6-1 | 704 | 89 | 1.29 | −13 | +7 |
| 154 | 17-2 | 6-2 | 703 | 87 | 1.28 | −13 | +7 |
| 155 | 17-2 | 6-3 | 700 | 83 | 1.25 | −15 | +10 |
| 156 | 17-2 | 6-4 | 704 | 89 | 1.26 | −14 | +10 |
| 157 | 17-2 | 6-1 | 708 | 85 | 1.23 | −16 | +9 |

Examples 158 to 163

According to the same manner as that described in Examples 144 to 149 except for using the hole transferring material and electron transferring material shown in Table 20, a single-layer type electrophotosensitive material was produced, respectively, and their electrical characteristics were evaluated. The results are shown in Table 20.

TABLE 20

CGM: 12-1

| | | | INITIAL CHARACTERISTICS | | | AFTER REPEATING | |
|---|---|---|---|---|---|---|---|
| EXAMPLE NO. | HTM | ETM | $V_0$ | Vr | $E_{1/2}$ | $\Delta V_0$ | ΔVr |
| 158 | 18-1 | 6-2 | 703 | 85 | 1.09 | −25 | +13 |
| 159 | 18-1 | 6-3 | 705 | 88 | 1.09 | −26 | +16 |
| 160 | 18-1 | 6-4 | 701 | 87 | 1.08 | −29 | +18 |
| 161 | 18-1 | 6-1 | 700 | 85 | 1.06 | −24 | +12 |
| 162 | 18-2 | 6-2 | 703 | 88 | 1.10 | −25 | +10 |
| 163 | 18-3 | 6-2 | 703 | 82 | 1.12 | −23 | +13 |

Examples 164 to 169

According to the same manner as that described in Examples 144 to 149 except for using 100 parts by weight of two sorts of compounds (each 50 parts by weight) shown in Table 21 as the hole transferring material and the electron transferring material shown in Table 21, a single-layer type electrophotosensitive material was produced, respectively, and their electrical characteristics were evaluated. The results are shown in Table 21.

TABLE 21

| | | | INITIAL CHARACTERISTICS | | | CGM: 12-1 AFTER REPEATING | |
|---|---|---|---|---|---|---|---|
| EXAMPLE NO. | HTM | ETM | $V_0$ | Vr | $E_{1/2}$ | $\Delta V_0$ | $\Delta Vr$ |
| 164 | 17-1 18-1 | 6-3 | 705 | 62 | 0.90 | −10 | +5 |
| 165 | 17-1 18-2 | 6-3 | 701 | 68 | 0.95 | −11 | +2 |
| 166 | 17-1 18-3 | 6-3 | 695 | 66 | 0.92 | −15 | +8 |
| 167 | 17-2 18-1 | 6-4 | 702 | 60 | 0.88 | −12 | +3 |
| 168 | 17-2 18-2 | 6-4 | 703 | 63 | 0.89 | −16 | +7 |
| 169 | 17-2 18-3 | 6-4 | 706 | 68 | 0.89 | −18 | +9 |

Examples 170 to 175 and Comparative Example 14

According to the same manner as that described in Examples 144 to 149 except for using the compound represented by the above formula (12-2) as the electric charge generating material and using the hole transferring material and electron transferring material shown in Table 22, a single-layer type electrophotosensitive material was produced, respectively, and their electrical characteristics were evaluated. The results are shown in Table 22.

TABLE 22

| | | | INITIAL CHARACTERISTICS | | | CGM: 12-2 AFTER REPEATING | |
|---|---|---|---|---|---|---|---|
| EXAMPLE NO. | HTM | ETM | $V_0$ | Vr | $E_{1/2}$ | $\Delta V_0$ | $\Delta Vr$ |
| 170 | 16-1 | 6-2 | 702 | 83 | 1.27 | −30 | +16 |
| 171 | 16-1 | 6-3 | 702 | 81 | 1.26 | −29 | +13 |
| 172 | 16-1 | 6-4 | 704 | 82 | 1.25 | −35 | +19 |
| 173 | 16-1 | 6-1 | 701 | 84 | 1.26 | −38 | +20 |
| 174 | 16-1 | 6-1 | 705 | 89 | 1.29 | −30 | +15 |
| 175 | 16-1 | 6-1 | 699 | 85 | 1.27 | −33 | +13 |
| COMP. EX. 14 | 16-1 | Q | 704 | 110 | 1.69 | −50 | +30 |

Examples 176 to 183

According to the same manner as that described in Examples 170 to 175 except for using the hole transferring material and electron transferring material shown in Table 23, a single-layer type electrophotosensitive material was produced, respectively, and their electrical characteristics were evaluated. The results are shown in Table 23.

TABLE 23

| | | | INITIAL CHARACTERISTICS | | | CGM: 12-2 AFTER REPEATING | |
|---|---|---|---|---|---|---|---|
| EXAMPLE NO. | HTM | ETM | $V_0$ | Vr | $E_{1/2}$ | $\Delta V_0$ | $\Delta Vr$ |
| 176 | 17-1 | 6-2 | 694 | 92 | 1.32 | −16 | +8 |
| 177 | 17-1 | 6-3 | 697 | 95 | 1.33 | −15 | +7 |
| 178 | 17-1 | 6-4 | 702 | 94 | 1.33 | −17 | +10 |
| 179 | 17-1 | 6-1 | 708 | 92 | 1.31 | −20 | +8 |
| 180 | 17-2 | 6-2 | 707 | 85 | 1.26 | −18 | +10 |

TABLE 23-continued

| | | | INITIAL CHARACTERISTICS | | | CGM: 12-2 AFTER REPEATING | |
|---|---|---|---|---|---|---|---|
| EXAMPLE NO. | HTM | ETM | $V_0$ | Vr | $E_{1/2}$ | $\Delta V_0$ | $\Delta Vr$ |
| 181 | 17-2 | 6-3 | 706 | 83 | 1.24 | −14 | +6 |
| 182 | 17-2 | 6-4 | 700 | 88 | 1.30 | −13 | +5 |
| 183 | 17-2 | 6-1 | 700 | 86 | 1.29 | −16 | +7 |

Examples 184 to 189

According to the same manner as that described in Examples 170 to 175 except for using the hole transferring material and electron transferring material shown in Table 24, a single-layer type electrophotosensitive material was produced, respectively, and their electrical characteristics were evaluated. The results are shown in Table 24.

TABLE 24

| | | | INITIAL CHARACTERISTICS | | | CGM: 12-2 AFTER REPEATING | |
|---|---|---|---|---|---|---|---|
| EXAMPLE NO. | HTM | ETM | $V_0$ | Vr | $E_{1/2}$ | $\Delta V_0$ | $\Delta Vr$ |
| 184 | 18-1 | 6-2 | 703 | 90 | 1.12 | −26 | +15 |
| 185 | 18-1 | 6-3 | 702 | 86 | 1.09 | −22 | +13 |
| 186 | 18-1 | 6-4 | 706 | 88 | 1.10 | −25 | +18 |
| 187 | 18-1 | 6-1 | 705 | 92 | 1.15 | −25 | +17 |
| 188 | 18-2 | 6-2 | 705 | 94 | 1.15 | −24 | +16 |
| 189 | 18-3 | 6-2 | 704 | 96 | 1.15 | −21 | +15 |

Examples 190 to 195

According to the same manner as that described in Examples 170 to 175 except for using 100 parts by weight of two sorts of compounds (each 50 parts by weight) shown in Table 25 as the hole transferring material and the electron transferring material shown in Table 25, a single-layer type electrophotosensitive material was produced, respectively, and their electrical characteristics were evaluated. The results are shown in Table 25.

TABLE 25

| | | | INITIAL CHARACTERISTICS | | | CGM: 12-2 AFTER REPEATING | |
|---|---|---|---|---|---|---|---|
| EXAMPLE NO. | HTM | ETM | $V_0$ | Vr | $E_{1/2}$ | $\Delta V_0$ | $\Delta Vr$ |
| 190 | 17-1 18-1 | 6-3 | 699 | 75 | 0.92 | −15 | +10 |
| 191 | 17-1 18-2 | 6-3 | 700 | 70 | 0.90 | −16 | +9 |
| 192 | 17-1 18-3 | 6-3 | 703 | 69 | 0.90 | −15 | +10 |
| 193 | 17-2 18-1 | 6-4 | 704 | 64 | 0.88 | −10 | +5 |
| 194 | 17-2 18-2 | 6-4 | 701 | 63 | 0.85 | −12 | +6 |
| 195 | 17-2 18-3 | 6-4 | 703 | 66 | 0.89 | −8 | +3 |

Reference Example 4

Synthesis of 3,4-dimethyltryptoanthrine 7,8-Dimethylisatoic anhyrdide (10 g, 0.052 mols) and isatin (10 g, 0.068 mol) were added to 60 ml of pyridine, and the mixture was reacted under reflux for about 6 hours. After the completion of the reaction, the reaction solution was cooled to deposit a crystal. Then, the crystal was filtered, washed with methanol and dried to obtain 4.2 g of the titled compound (yield: 29%).

Reference Example 5

Synthesis of 3,4-dimethyl-2,6-dinitrotryptoanthrine 3,4-Dimethyltryptoanthrine (5 g) was added to 50 ml of a mixed acid (concentrated sulfuric acid:concentrated nitric acid=1:1), and the mixture was reacted at 40° C. for one hour. After the completion of the reaction, the reaction solution was added to ice water to deposit a crystal. Then, the crystal was filtered, washed with water, dried and recrystallized from acetic acid to obtain 3 g of the titled compound (yield: 45%).

Melting point: 275° C.

Reference Example 6

Synthesis of 7-isopropyltryptoanthrine

6-Isopropylisatin (10 g, 0.053 mol) and isatoic anhydride (10 g, 0.061 mols) were added to 60 ml of pyridine, and the mixture was reacted under reflux for about 6 hours. After the completion of the reaction, the reaction solution was cooled to deposit a crystal. Then, the crystal was filtered, washed with methanol and dried to obtain 4.8 g of the titled compound (yield: 31%).

Reference Example 7

Synthesis of 7-isopropyl-2,6-dinitrotryptoanthrine

According to the same manner as that described in Reference Example 2 except for using 7-siopropyltryptoanthrine as the starting material, the titled compound was obtained.

Melting point: 268° C.

Synthesis Example 19

Synthesis of N-(2,6-diethylphenyl)-3,4-dimethyl-2,6-dinitrotryptoanthrinimine 3,4-Dimethyl-2,6-dinitrotryptoanthrine (6 g) and 2,6-diethylaniline (2.6 g) were dissolved in 50 ml of acetic acid, and the mixture was reacted under reflux for 2 hours. After the completion of the reaction, the reaction solution was added to 400 ml of water to deposit a crystal. Then, the crystal was filtered, washed with water, dried and purified by subjecting to silica gel column chromatography (developing solvent: mixed solvent of chloroform and hexane) to obtain 4.6 g of the titled compound (compound of the above formula (7-1), yield: 56%).

Melting point: 245° C.

Figure 14:
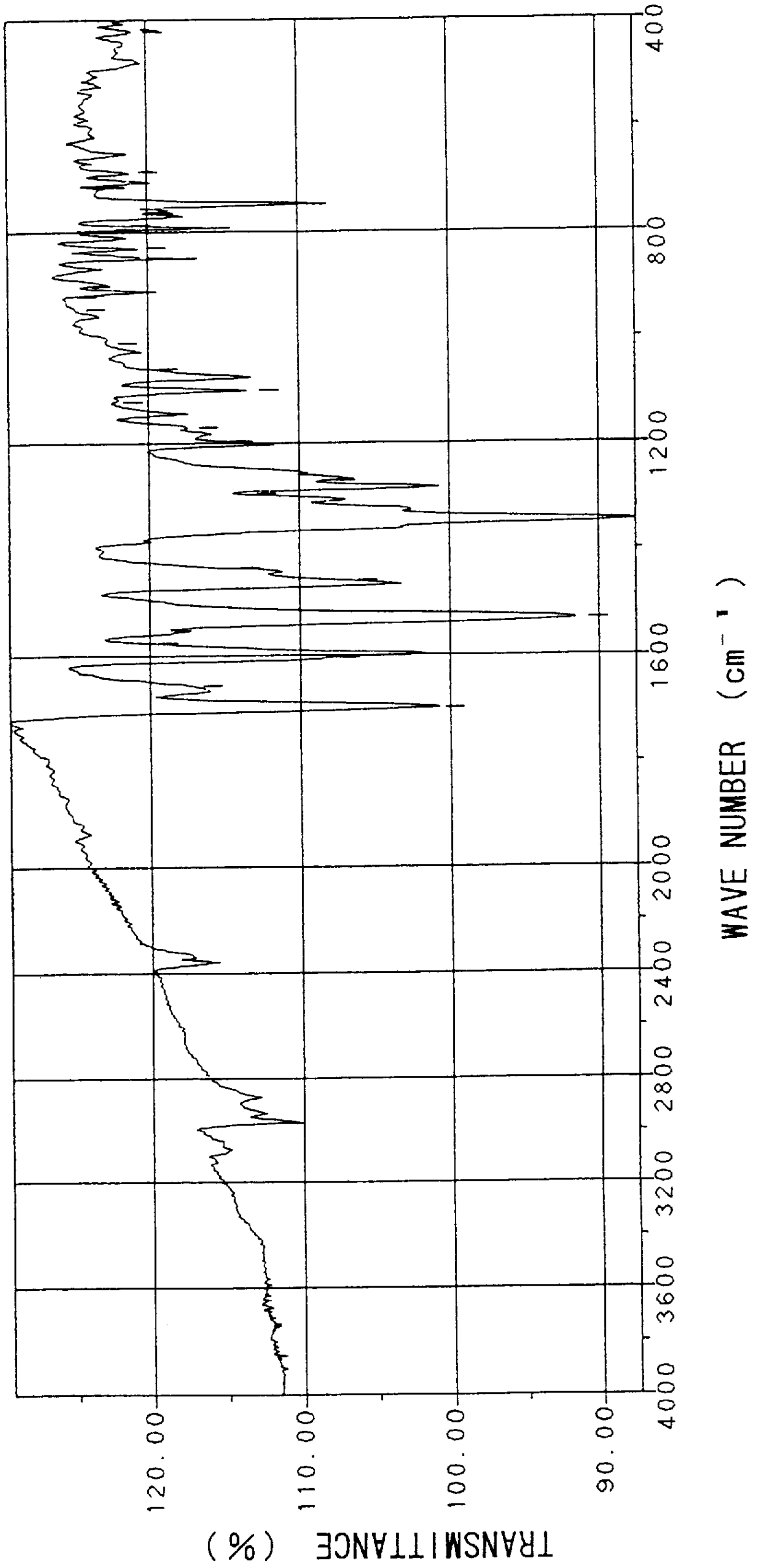

The infrared spectrum of the compound (7-1) is shown in FIG. 14.

Synthesis Example 20

Synthesis of N-(2-isopropyl-6-methylphenyl)-7-isopropyl-2,6-dinitrotryptoanthrinimine According to the same manner as that described in Synthesis Example 19 except for using 7-isopropyl-2,6-dinitrotryptoanthrine and 2-isopropyl-6-methylaniline as the starting material, 5.3 g of the titled compound (compound of the above formula (7-2)) was obtained (yield: 66%).

Melting point: 253° C.

Figure 15:
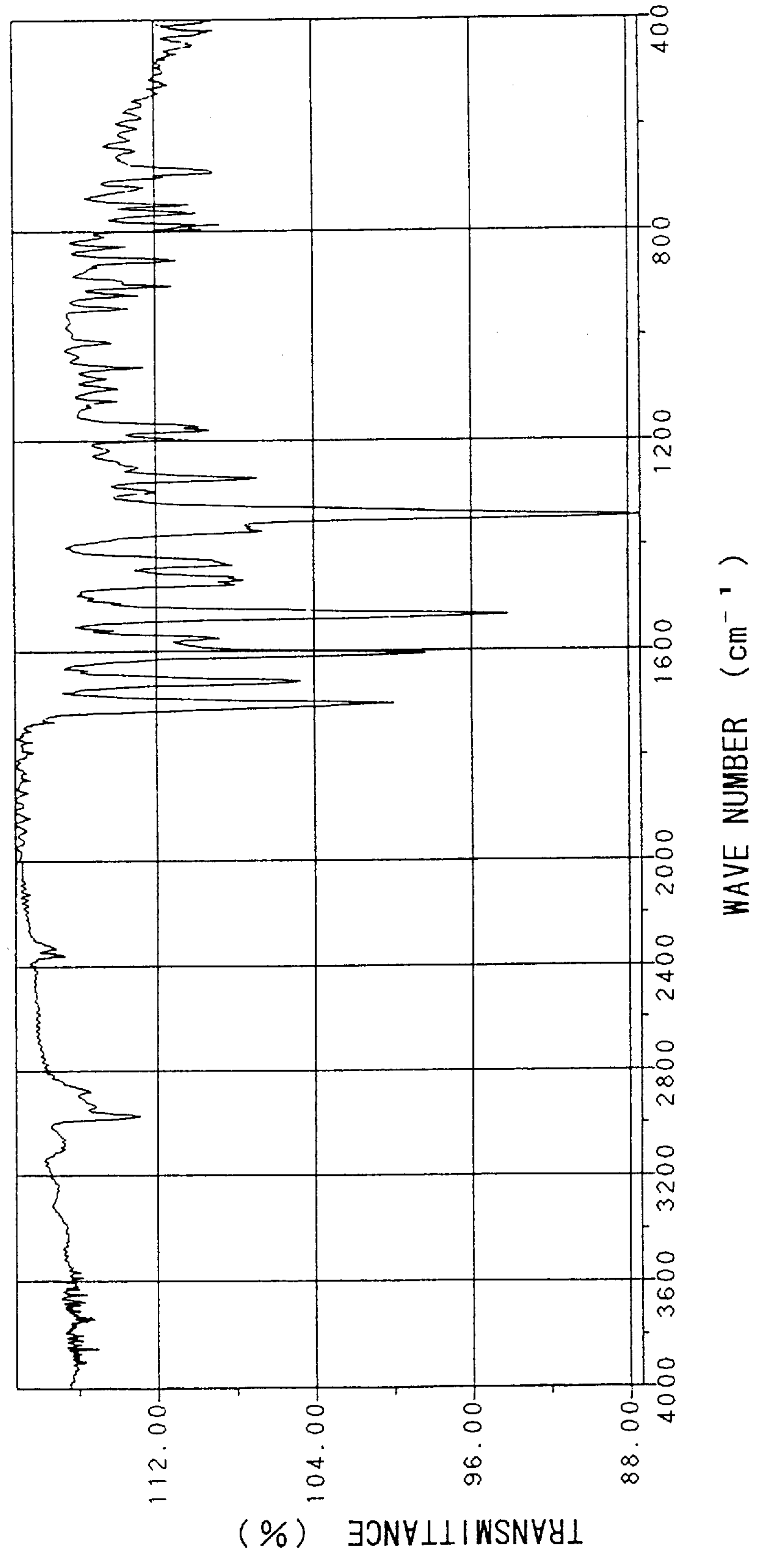

The infrared spectrum of the compound (7-2) is shown in FIG. 15.

Synthesis Example 21

Synthesis of N-(2-biphenylyl)-7-isopropyl-2,6-dinitrotryptoanthrinimine

According to the same manner as that described in Synthesis Example 20 except for using 2-aminobiphenyl in place of 2-isopropyl-6-methylaniline, the reaction was conducted to obtain the titled compound. Compound of the above formula (7-3)

Melting point: 191° C.

Figure 16:
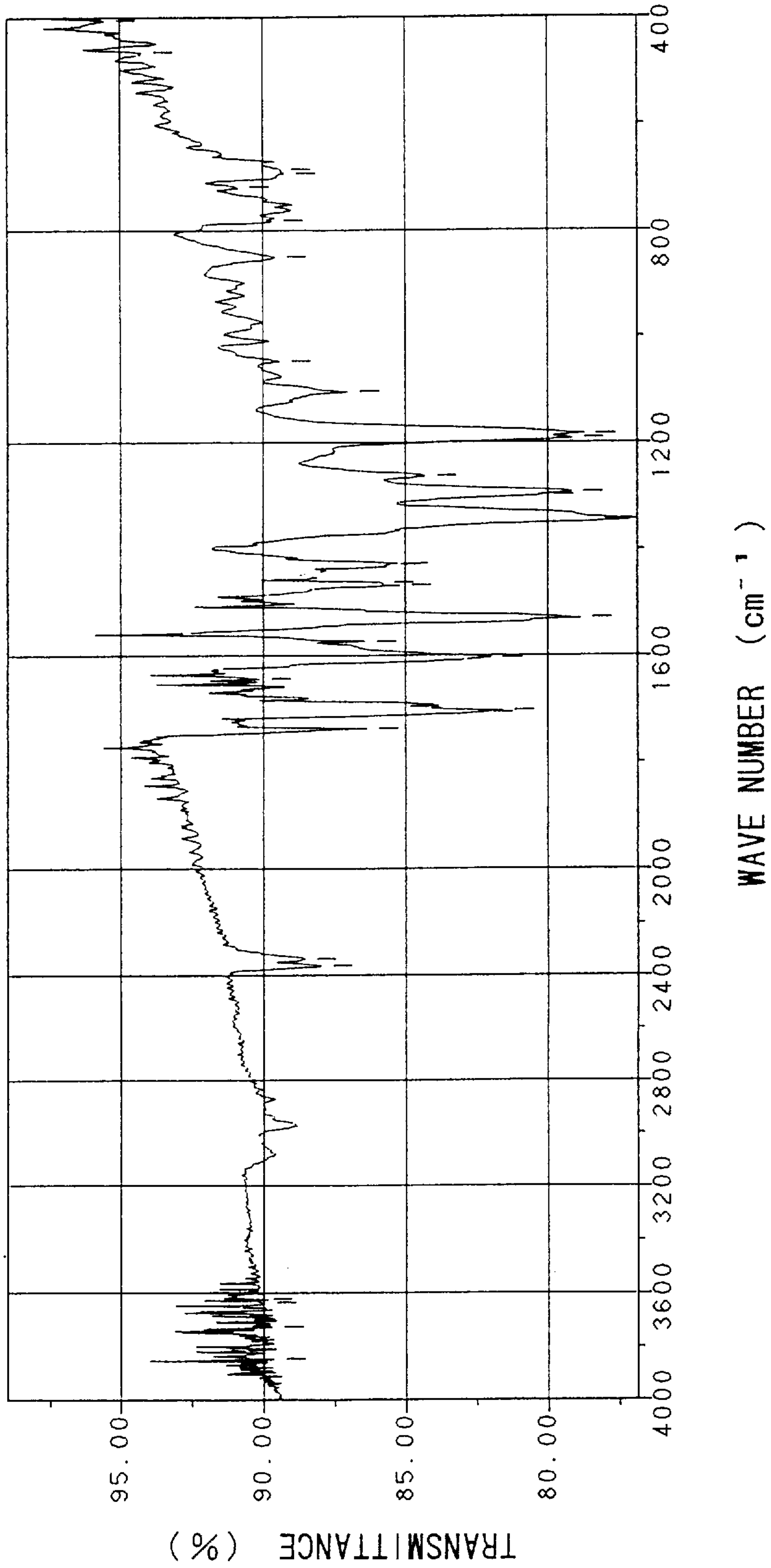

The infrared spectrum of the compound (7-3) is shown in FIG. 16.

Production of electrophotosensitive material

The respective components used in the following Examples and Comparative Examples are the same as those used in Examples 120 to 195 and Comparative Examples 8 to 14 except for the electron transferring material. Therefore, they are shown by the same symbols or numerals. The electron transferring materials used are as follows.

7-1: tryptoanthrinimine derivative represented by the above formula (7-1)

7-2: tryptoanthrinimine derivative represented by the above formula (7-2)

7-3: tryptoanthrinimine derivative represented by the above formula (7-3)

Q: 3,5-dimethyl-3',5'-di-t-butyl-4,4'-diphenoquinone

Examples 196 and 197 and Comparative Examples 15 and 16

According to the same manner as that described in Examples 120 to 129 and Comparative Examples 8 to 12 except for using the respective components shown in Table 26 as the electric charge generating material (EGM), hole transferring material (HTM) and electron transferring material (ETM), a single-layer type electrophotosensitive material for digital light source was produced, respectively.

Examples 198 to 200

According to the same manner as that described in Examples 196 and 197 and Comparative Examples 15 and 16 except that 5 parts by weight of an electric charge generating material, 50 parts by weight of a hole transferring material, 30 parts by weight of an electron transferring material, 100 parts by weight of a binding resin and 800 parts by weight of a solvent were added and 10 parts by weight of an electron acceptive compound was further blended to prepare a coating solution for single-layer type photosensitive layer, a single-layer type electrophotosensitive material for digital light source was produced, respectively.

Examples 201 and Comparative Example 17

According to the same manner as that described in Examples 196 and 197 and Comparative Examples 15 and 16 except for using a perylene pigment as the electric charge generating material, a single-layer type electrophotosensitive material for analog light source was produced, respectively.

Example 202 and Comparative Example 18

100 Parts by weight of an electric charge generating material ($PcH_2$), 100 parts by weight of a binding resin (polyvinyl butyral) and 2,000 parts by weight of a solvent (tetrahydrofuran) were mixed and dispersed in a ball mill for 50 hours to prepare a coating solution for electric charge generating layer. Then, this coating solution was applied on an aluminum tube as the conductive substrate by a dip coating method, followed by hot-air drying at 100° C. for 60 minutes to form an electric charge generating layer of 1 μm in film thickness.

Example 203 and Comparative Example 19

According to the same manner as that described in Example 202 and Comparative Example 18 except for using a perylene pigment as the electric charge generating material, a multi-layer type electrophotosensitive material for analog light source was produced, respectively.

The potential after exposure $V_L$ of the photosensitive materials obtained in Examples 196 to 203 and Comparative Examples 15 to 19 was measured according to the same manner as that described in Examples 1 to 33. The results are shown in Table 26.

TABLE 26

| EXAMPLE NO. | CGM | HTM | ETM | EAC | $V_L$ (V) |
|---|---|---|---|---|---|
| 196 | $PcH_2$ | 16-1 | 7-1 | — | 173 |
| COMP. EX. 15 | $PcH_2$ | 16-1 | Q | — | 220 |
| 197 | PcTiO | 16-1 | 7-1 | — | 182 |
| COMP. EX. 16 | PcTiO | 16-1 | Q | — | 242 |
| 198 | $PcH_2$ | 16-1 | 7-1 | BQ | 164 |
| 199 | $PcH_2$ | 16-1 | 7-1 | Q | 149 |
| 200 | $PcH_2$ | 16-1 | 7-1 | Bu—DPQ | 144 |
| 201 | PERYLENE | 16-1 | 7-1 | — | 207 |
| COMP. EX. 17 | PERYLENE | 16-1 | Q | — | 294 |
| 202 | $PcH_2$ | — | 7-1 | — | 259 |
| COMP. EX. 18 | $PcH_2$ | — | Q | — | 346 |
| 203 | PERYLENE | — | 7-1 | — | 300 |
| COMP. EX. 19 | PERYLENE | — | Q | — | 386 |

Example 204 to 210

According to the same manner as that described in Example 196 to 203 except for using the compound represented by the above formula (7-2) as the electron transferring material, an electrophotosensitive material was produced, respectively.

The potential after exposure $V_L$ of the resulting electrophotosensitive materials was measured according to the same manner as that described in Examples 1 to 33. The results are shown in Table 27.

TABLE 27

| EXAMPLE NO. | CGM | HTM | ETM | EAC | $V_L$ (V) |
|---|---|---|---|---|---|
| 204 | $PcH_2$ | 16-1 | 7-2 | — | 170 |
| 205 | PcTiO | 16-1 | 7-2 | — | 179 |
| 206 | $PcH_2$ | 16-1 | 7-2 | Bu—BQ | 154 |
| 207 | $PcH_2$ | 16-1 | 7-2 | Bu—DPQ | 142 |
| 208 | PERYLENE | 16-1 | 7-2 | — | 204 |
| 209 | $PcH_2$ | — | 7-2 | — | 255 |
| 210 | PERYLENE | — | 7-2 | — | 296 |

Example 211 to 217

According to the same manner as that described in Example 196 to 203 except for using the compound represented by the above formula (7-3) as the electron transferring material, an electrophotosensitive material was produced, respectively.

The potential after exposure $V_L$ of the resulting electrophotosensitive materials was measured according to the same manner as that described in Examples 1 to 33. The results are shown in Table 28.

TABLE 28

| EXAMPLE NO. | CGM | HTM | ETM | EAC | $V_L$ (V) |
|---|---|---|---|---|---|
| 211 | $PcH_2$ | 16-1 | 7-3 | — | 176 |
| 212 | PcTiO | 16-1 | 7-3 | — | 188 |
| 213 | $PcH_2$ | 16-1 | 7-3 | BQ | 169 |
| 214 | $PcH_2$ | 16-1 | 7-3 | Bu—DPQ | 140 |
| 215 | PERYLENE | 16-1 | 7-3 | — | 210 |
| 216 | $PcH_2$ | — | 7-3 | — | 261 |
| 217 | PERYLENE | — | 7-3 | — | 302 |

What is claimed is:

1. A tryptoanthrinimine compound represented by the formula (Y):

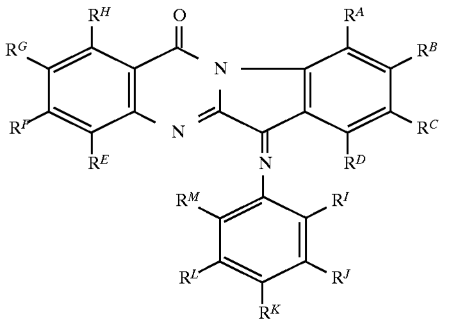

(Y)

wherein $R^A$, $R^B$, $R^C$, $R^D$, $R^E$, $R^F$, $R^G$ and $R^H$ are the same or different and indicate a hydrogen atom, an alkyl group, an alkoxy group, or a nitro group; and $R^I$, $R^J$, $R^K$, $R^L$ and $R^M$ are the same or different and indicate a hydrogen atom, an alkyl group, an aryl group which may have a substituent, an aralkyl group, an alkoxy group, a phenoxy group, an alkyl halide group or a halogen atom.

2. A tryptoanthrinimine compound according to claim 1, represented by the formula (1):

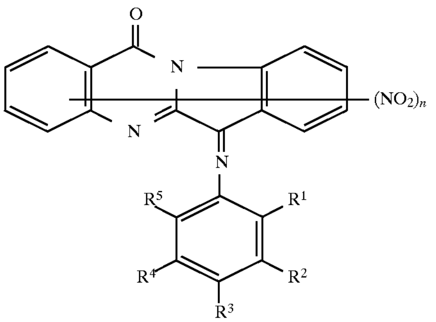

(1)

wherein $R^1$, $R^2$, $R^3$, $R^4$ and $R^5$ are the same or different and indicate a hydrogen atom, an alkyl group, an aryl group, an aralkyl group, an alkoxy group, an alkyl halide group or a halogen atom; and n is an integer of 1 to 4.

3. A tryptoanthrinimine compound according to claim 1, represented by the formula (6):

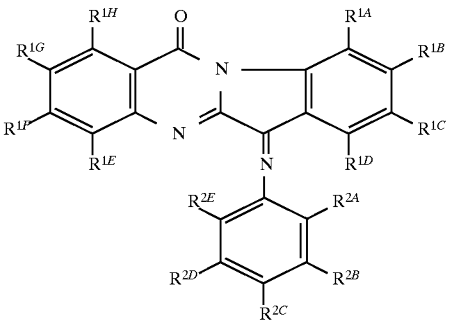

(6)

wherein $R^{1A}$, $R^{1B}$, $R^{1C}$, $R^{1D}$, $R^{1E}$, $R^{1F}$, $R^{1G}$ and $R^{1H}$ are the same or different and indicate a hydrogen atom, an alkyl group, or an alkoxy group; $R^{2A}$, $R^{2B}$, $R^{2C}$, $R^{2D}$ and $R^{2E}$ are the same or different and indicate a hydrogen atom, an alkyl group, an alkoxy group, an aryl group, an aralkyl group, a phenoxy group, or a halogen atom.

4. A tryptoanthrinimine compound according to claim 1, represented by the formula (7):

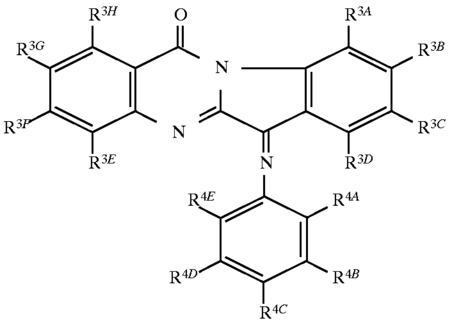

(7)

wherein, at least two substituents of $R^{3A}$, $R^{3B}$, $R^{3C}$, $R^{3D}$, $R^{3E}$, $R^{3F}$, $R^{3G}$ and $R^{3H}$ indicate a nitro group, at least one substituent indicates an alkyl group or an alkoxy group, and others indicate a hydrogen atom; $R^{4A}$, $R^{4B}$, $R^{4C}$, $R^{4D}$ and $R^{4E}$ are the same or different and indicate a hydrogen atom, an alkyl group, an alkoxy group, an aryl group, an aralkyl group, or a halogen atom.

5. A tryptoanthrinimine derivative according to claim 2, wherein the derivative is a compound represented by the following formula (1-4) or (1-7):

(1-4)

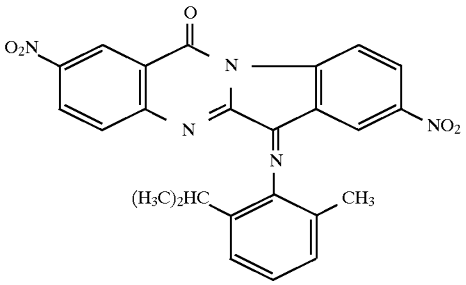

-continued (1-7)

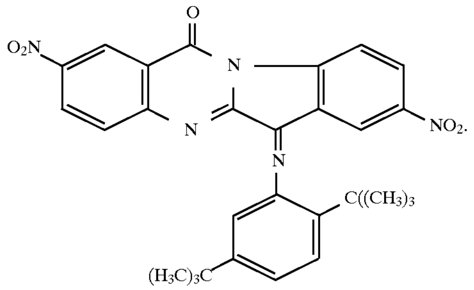

6. A tryptoanthrinimine derivative according to claim 3, wherein the derivative is a compound selected from a group consisting of the following formulas (6-1), (6-2), (6-3) or (6-4):

(6-1)

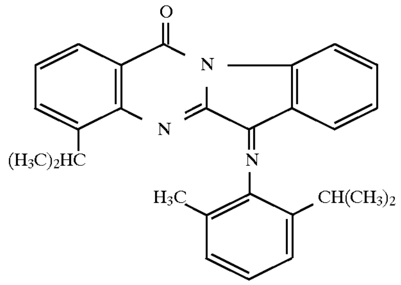

(6-2)

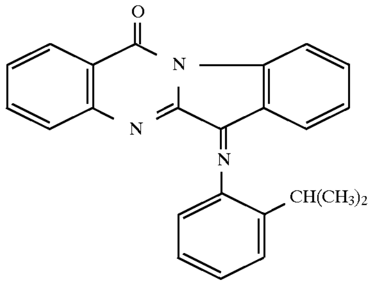

(6-3)

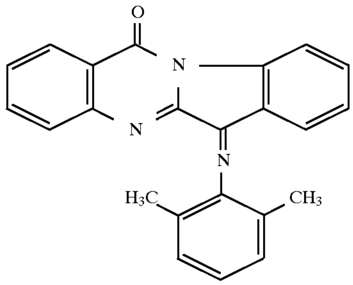

-continued
(6-4)
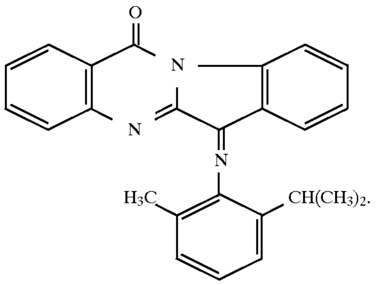
7. A tryptoanthrinimine derivative according to claim 4, wherein the derivative is a compound selected from a group consisting of the following formula (7-1), (7-2) or (7-3):
(7-1)
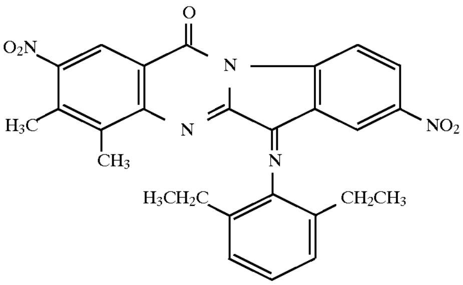
-continued
(7-2)
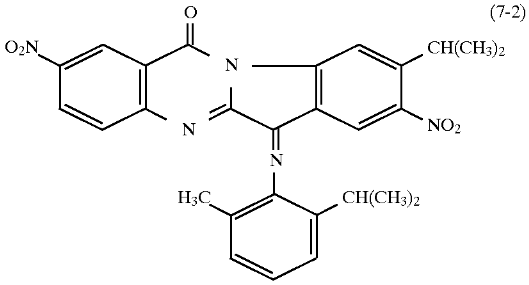
(7-3)
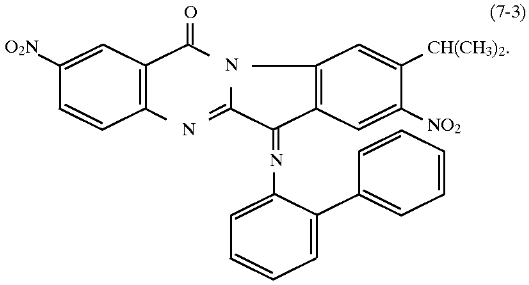
* * * * *